(12) United States Patent
Cooper

(10) Patent No.: US 9,339,479 B2
(45) Date of Patent: May 17, 2016

(54) DOSAGE FORMS AND RELATED THERAPIES

(71) Applicant: Garth James Smith Cooper, Auckland (NZ)

(72) Inventor: Garth James Smith Cooper, Auckland (NZ)

(73) Assignee: PHILERA NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 14/573,211

(22) Filed: Dec. 17, 2014

(65) Prior Publication Data

US 2015/0164826 A1 Jun. 18, 2015

Related U.S. Application Data

(63) Continuation of application No. 10/525,345, filed as application No. PCT/NZ03/00184 on Aug. 20, 2003, now abandoned.

(30) Foreign Application Priority Data

| Aug. 20, 2002 | (NZ) | ......................................... 520895 |
| Aug. 20, 2002 | (NZ) | ......................................... 520896 |
| Aug. 20, 2002 | (NZ) | ......................................... 520897 |
| Mar. 17, 2003 | (NZ) | ......................................... 524794 |
| Mar. 17, 2003 | (NZ) | ......................................... 524795 |
| Mar. 17, 2003 | (NZ) | ......................................... 524796 |

(51) Int. Cl.
*A61K 31/131* (2006.01)
*A61K 31/30* (2006.01)
*A61K 31/194* (2006.01)

(52) U.S. Cl.
CPC ............. *A61K 31/131* (2013.01); *A61K 31/194* (2013.01); *A61K 31/30* (2013.01)

(58) Field of Classification Search
CPC .................................................... A61K 31/131
See application file for complete search history.

(56) References Cited

U.S. PATENT DOCUMENTS

| 3,791,988 A | 2/1974 | Pratteln et al. |
| 4,323,558 A | 4/1982 | Nelson |
| 4,374,829 A | 2/1983 | Harris et al. |
| 4,410,541 A | 10/1983 | Kamimae et al. |
| 4,758,583 A | 7/1988 | Cerami et al. |
| 4,866,090 A | 9/1989 | Hoffman et al. |

(Continued)

FOREIGN PATENT DOCUMENTS

| DE | 3217071 A1 | 11/1983 |
| EP | 0331014 A3 | 2/1989 |

(Continued)

OTHER PUBLICATIONS

Gerhardinger, et al., "Novel Degradation Pathway of Glycated Amino Acids into Free Fructosamine by a *Pseudomonas* sp. Soil Strain Extract," J Biol Chem, 270, 1, pp. 218-224 (1995).

(Continued)

*Primary Examiner* — Benjamin Packard

(57) ABSTRACT

This invention is directed in part to novel doses, dosage formulations, and routes of administration of such doses and dose formulations, said dose and dose formulations containing one or more copper chelators, for example, one or more trientine active agents, including trientine analogs, trientine salts, trientine prodrugs, and trientine derivatives, useful in the treatment of diseases, disorders and conditions, including in indications where copper may play a role.

18 Claims, 26 Drawing Sheets

(56) References Cited

U.S. PATENT DOCUMENTS

| | | | |
|---|---|---|---|
| 4,952,568 A | 8/1990 | Sawai et al. |
| 5,077,313 A | 12/1991 | Lubec |
| 5,128,360 A | 7/1992 | Cerami et al. |
| 5,246,970 A | 9/1993 | Williamson et al. |
| 5,366,505 A | 11/1994 | Farber |
| 5,387,109 A | 2/1995 | Ishikawa et al. |
| 5,420,120 A | 5/1995 | Boltralik |
| 5,811,446 A | 9/1998 | Thomas |
| 5,824,049 A | 10/1998 | Ragheb et al. |
| 5,852,009 A | 12/1998 | Cerami et al. |
| 5,854,271 A | 12/1998 | Thomas et al. |
| 5,906,996 A | 5/1999 | Murphy |
| 5,972,985 A | 10/1999 | Thomas et al. |
| 5,980,914 A | 11/1999 | Gerolymatos |
| 6,147,070 A | 11/2000 | Facchini |
| 6,309,380 B1 | 10/2001 | Larson et al. |
| 6,329,414 B1 | 12/2001 | Thomas et al. |
| 6,348,465 B1 | 2/2002 | Baker |
| 6,576,672 B1 | 6/2003 | Murphy |
| 6,610,693 B2 | 8/2003 | Baker |
| 6,821,954 B2 | 11/2004 | Reid et al. |
| 6,855,511 B2 | 2/2005 | Baker |
| 6,884,575 B2 | 4/2005 | Cooper et al. |
| 6,897,243 B2 | 5/2005 | Baker et al. |
| 6,951,890 B2 | 10/2005 | Cooper et al. |
| 2002/0034775 A1 | 3/2002 | Baker |
| 2003/0013772 A1 | 1/2003 | Murphy et al. |
| 2003/0045506 A1 | 3/2003 | Baker |
| 2003/0050434 A1 | 3/2003 | Cooper et al. |
| 2003/0055003 A1 | 3/2003 | Bar-Or et al. |
| 2003/0055113 A1 | 3/2003 | Wang et al. |
| 2003/0139312 A1 | 7/2003 | Caswell et al. |
| 2003/0166561 A1 | 9/2003 | Cooper et al. |
| 2003/0186946 A1 | 10/2003 | Cooper et al. |
| 2003/0203973 A1 | 10/2003 | Cooper et al. |
| 2003/0232799 A1 | 12/2003 | Wang et al. |
| 2004/0019087 A1 | 1/2004 | Ternansky et al. |
| 2004/0023854 A1 | 2/2004 | Cooper et al. |
| 2004/0038861 A1 | 2/2004 | Cooper et al. |
| 2004/0076603 A1 | 4/2004 | Peled et al. |
| 2004/0142393 A1 | 7/2004 | Cooper et al. |
| 2004/0259945 A1 | 12/2004 | Brewer et al. |
| 2005/0002876 A1 | 1/2005 | Yukl et al. |
| 2005/0009760 A1 | 1/2005 | Wang et al. |
| 2005/0031651 A1 | 2/2005 | Gervais et al. |
| 2005/0047998 A1 | 3/2005 | Cooper et al. |
| 2005/0074756 A1 | 4/2005 | Cooper et al. |
| 2005/0085555 A1 | 4/2005 | Murphy et al. |
| 2005/0159364 A1 | 7/2005 | Cooper et al. |
| 2005/0159489 A1 | 7/2005 | Baker et al. |
| 2006/0009534 A1 | 1/2006 | Cooper et al. |
| 2006/0041170 A1 | 2/2006 | Jonas et al. |
| 2006/0128610 A1 | 6/2006 | Cooper |

FOREIGN PATENT DOCUMENTS

| | | |
|---|---|---|
| EP | 0426066 A2 | 5/1991 |
| EP | 0576838 A3 | 1/1994 |
| EP | 1234585 A3 | 8/2002 |
| GB | 2192789 A | 1/1988 |
| GB | 2192790 A | 1/1988 |
| JP | 7118148 | 5/1995 |
| JP | 2000204037 | 7/2000 |
| PL | P.202419 | 12/1979 |
| WO | 82/01804 A | 5/1982 |
| WO | 85/04169 A1 | 9/1985 |
| WO | 87/05505 A1 | 9/1987 |
| WO | 95/11690 A1 | 5/1995 |
| WO | 95/17900 | 7/1995 |
| WO | 96/12483 A1 | 5/1996 |
| WO | 98/40071 A1 | 9/1998 |
| WO | 99/39712 A1 | 8/1999 |
| WO | 00/18392 A1 | 4/2000 |
| WO | 00/18891 A1 | 4/2000 |
| WO | 9945907 A9 | 11/2000 |
| WO | 00/78805 A1 | 12/2000 |
| WO | 02/73722 A1 | 6/2002 |
| WO | 02/079785 A2 | 10/2002 |
| WO | 03/045424 A1 | 6/2003 |
| WO | 03/057719 A3 | 7/2003 |
| WO | 03/062275 A1 | 7/2003 |
| WO | 03/063880 A1 | 8/2003 |
| WO | 03/074559 A1 | 9/2003 |
| WO | 03/075910 A1 | 9/2003 |
| WO | 03/077901 A1 | 9/2003 |
| WO | 03/082259 A1 | 10/2003 |
| WO | 03/093311 A1 | 11/2003 |
| WO | 03/099223 A3 | 12/2003 |
| WO | 2004/012760 A1 | 2/2004 |
| WO | 2004/012761 A1 | 2/2004 |
| WO | 2004/017956 A1 | 3/2004 |
| WO | 2004/017957 A1 | 3/2004 |
| WO | 2004/056861 A3 | 7/2004 |
| WO | 2004/065614 A3 | 8/2004 |
| WO | 2004/083215 A3 | 9/2004 |
| WO | 2004/087160 A1 | 10/2004 |
| WO | 2005/000337 A1 | 1/2005 |
| WO | 2005/040205 A1 | 5/2005 |
| WO | 2005/058294 A1 | 6/2005 |
| WO | 2006/027705 A1 | 3/2006 |

OTHER PUBLICATIONS

Gillery, et al., "Glycation of proteins as a source of superoxides," Diabete Metab, vol. 14, No. I, pp. 25-30, XP001058074 (1988).

Green et al, "Stoichoimetry of O2 Metabolism and NADPH Oxidation of the Cell-free Latent Oxidase Reconstituted from Cytosol and Solubilized Membrane from Resting Human Neutrophils," J. Biol. Chem., vol. 268, No. 2, pp. 857-861, XP002192176 (1993).

Greenman, et al., "Subchronic toxicity of triethylenetetramine dihydrochloride in B6C3FI mice and F344 rats," Fundam. Appl. Toxicol., 29, 2, pp. 185-193 (1996).

Greenstock, et al, "Determination of superoxide (02-) Radical Anion Reaction Rates Using Pulse Radiolysis," Int J Radial Phys Chem, 8, pp. 367-369 (1976).

Halliwell, "An Attempt to Demonstrate a Reaction between Superoxide and Hydrogen Peroxide," FEBS Lett, 72,1, pp. 8-10 (1976).

Halliwell, et al, "Free Radicals in Biology and Medicine," Clarendon Press, Oxford, pp. 136-176 (1989).

Haslam, et al. "Treatment of Wilson's Disease with Triethylene Tetramine Dihydrochloride," Dev Pharmacal Ther, 1, 5, pp. 318-324 (1980).

Hoffken, et at., "Excretion of Zinc in Diabetics Receiving Penicillamine," Z Klin Chern Klin Biochem., 1, pp. 4-7 (1969).

Holdiness, "Clinical Pharmacokinetics of N-Acetylcysteine," Clin Pharmacokinet, 20, 2, pp. 123-124 (1991).

Horiuchi, et al "Purification and Properties of Fructosyl-amino Acid Oxidase from *Corynebacterium* sp. 2-4-1," Agric Bioi Bioi Chern, 53, 1, pp. 103-110 (1989).

Ido, et al., "Interactions between the Sorbitol Pathway, Non-enzymatic Glycation, and Diabetic Vascular Dysfunction," Nephrol Dial Transplant, 11, [Suppl5], pp. 72-75 (1996).

Iseki, et al., "Comparison of Disposition Behavior and De-Coppering Effect of Triethylenetetramine in Animal Model for Wilson's Disease (Long-Evans Cinnamon Rat) with Normal Wistar Rat," Biopharmaceutics & Drug Disposition, 13, pp. 273-283 (1992).

Jeremy, et al., "Copper Chelators Inhibit Platelet Thromboxane A2 Synthesis and Lipoxygenase Activity, In Vitro", J. Drug Dev Clin Pract, 7, pp. 119-126 (1995).

Jiang, et al. "Spirohydantoin Inhibitors of Aldose Reductase Inhibit Iron-and Copper-Catalysed Ascorbate Oxidation in Vitro," Biochemical Pharmacology, vol. 42., No. 6, pp. 1273-1278 (1991).

Karlsson, "Heparin-induced Release of Extracellular Superoxide Dismutase to Human Blood Plasma," Biochem J, 242, 55-59 (1987).

Karmazyn, et al., "Prostaglandin Concentrations Cause Cardiac Rhythm Disturbances. Effect Reversed by Low Levels of Copper or Chloroquine," Prostaglandins, vol. 15, (1978).

(56) References Cited

OTHER PUBLICATIONS

Kashihara, et al., (1992). "Selective Decreased de novo Synthesis of Glomerular roteoglycans under the Influence of Reactive Oxygen Species," Proc Natl Acad Sci USA, 89, pp. 6309-6313 (1992).

Keegan, A. et al., "Transition Metal Chelators and Anti-Oxidants Prevent the Development of Defective Endothelium-Dependent Relaxation in Aortas from Diabetic Rats," Diabetic Medicine, 13(Suppl. J), S 17 Abstract (1996).

Keegan, et al., "Effects of Chelator Treatment on Aorta and Corpus Cavernosum From Diabetic Rats," Free Radical Biology & Medicine, 27, 5-6, pp. 536-543 (1999).

Klein, et al., "Retinopathy in Young-onset Diabetic Patients," Diabetes Care, 8, 4, pp. 311-315 (1985).

Klevay, "Coronary Heart Disease: the Zinc/ Copper Hypothesis," The American Journal of Clinical Nutrition, 28, pp. 764-774 (1975).

Kodama, et al, "Metabolism of Administered Triethylene Tetramine Dihydrochloride in Humans," Life Sciences, 61, 9, pp. 899-907 (1997).

Konarkowska, et al., "Thiol reducing compounds prevent human amylin-evoked cytotoxicity," FEBS J, 272, 19, pp. 4949-4959 (2005).

Laight, et al., "Microassay of superoxide anion scavenging activity in vitro," Environmental Toxicology and Pharmacology, vol. 3, pp. 65-68, XP002192177 (1997).

Leighton, et al., "Pancreatic amylin and calcitonin gene-related peptide cause resistance to insulin in skeletal muscle in vitro," Nature, 335, 6191, pp. 632-635 (1998).

Leinonen, et al., "Susceptibility of LDL to oxidation is not associated with the presence of coronary heart disease or renal dysfunction in NIDDM patients," Clinica Chimica Acta, 275, pp. 163-174 (1998).

Love, et al., "Nerve Function and Regeneration in Diabetic and Galactosaemic Rats: Antioxidant and Metal Chelator Effects," European Journal of Pharmacology, 314, pp. 33-39 (1996).

Marklund, et al., "Superoxide Dismutase in Extracellular Fluids," Clin Chimica Acta, 126, pp. 41-51 (1982).

Mattock, et al., "Microalbuminuria and Coronary Heart Disease in NIDDM: An Incidence Study," Diabetes, 47, pp. 1786-1792 (1998).

McArdle, et al., "Effect of chelators on copper metabolism and cooper pools in mouse hepatocytes," Am. J. Physiol., 256, (Gastrointest. Liver Physiol. 19), pp. G667-G672 (1989).

McCord, et al, "Superoxide Dismutase: An Enzymic Function for Erythrocuprein (Hemocuprein)," J Bioi Chem, 244, 22, pp. 6049-6055 (1969).

McQuaid, et al., "A Comparison of the Effects of Penicillamine, Trientine, and Trithiomolybdate on [.sup.35 S]-labeled Metallothionein In Vitro; Implications for Wilson's Disease Therapy," Journal of Inorganic Biochemistry, 41, pp. 87-92 (1990).

Misra, et al, "Superoxide Dismutase: 'Positive' Spectrophotometric Assays," Anal Biochem, 79, pp. 553-560 (1977).

Misra, et al. "The Role of Superoxide Anion in the Autoxidation of Epinephrine and a Simple Assay for Superoxide Dismutae," J Bioi Chem, 247, 10, pp. 3170-3175 (1972).

Mizobuchi, et al., "Serum Superoxide Dismutase (SOD) Activity in Diabetes Mellitus," Rinsho Byori, 41, pp. 673-678 (English Abstract) (1993).

Mogensen, et al, "Predicting Diabetic Nephropathy in Insulindependent Patients," New Eng J Med, 311, 2, pp. 89-93 (1984).

Mogensen, et al., "Microalbuminuria in Non-insulin-dependent Diabetes," Clin Nephrol, 38, (suppl 1), pp. S28-S38 (1992).

Monnier, "Transition Metals Redox: Reviving an Old Plot for Diabetic Vascular Disease," The Journal of Clinical Investigation, vol. 107, No. 7, 799-801 (2001).

Morita, et al., "Wilson's disease treatment by triethylene tetramine dihydrochloride (trientine, 2HClO: long-term observations, " Dev. Pharmcacol. Ther., 19, 1, pp. 6-9 (1992).

Morpurgo, et al., "The Role of Copper in Bovine Serum Amine Oxidase," Biol Metals, 3, pp. 114-117 (1990).

Motoko, et al., "Isolation, purification, and characterization of amadorias isoenzymes (fructosyl amine-oxygen oxidoreductase EC 1.5.3) from Aspergillus sp.," Journal of Biological Chemistry, vol. 272, No. 6, pp. 3437-3443, XP002189585 ISSN: 0021-9258 (1997).

Motoko, et al., "Molecular cloning and expression of amadoriase isoenzyme (fructosyl amine:oxygen oxidoreductase, EC 1.5.3) from Aspergillus fumigatus," Journal of Biological Chemistry, vol. 272, No. 19, pp. 12505-12507, XP002189584 ISSN: 0021-9258 (1997).

Muchova, et al., "Antioxidant systems inpolymorphonuclear leucocytes of type 2 diabetes mellitus," Diabet Med. 16 (1):74-78 (1999).

Muruganandam, et al., "ELISA for In Vivo Assessment of Nonenzymatically Flycated Platelet Glutathione Peroxidase," Clin. Biochem., 27, 4, pp. 293-298 (1994).

Nitenberg et al., "Coronary Artery Response to Physiological Stimuli Are Improved by Deferoxamine but not by L-Arginine in Non-Insulin-Dependent Diabetic Patients With Angiographically Normal Coronary Arteries and No Other Risk Factors," American Heart Association, XP-002366411 (1997).

Nobuyuki, et al. "Distribution and properties of fructosyl amino acid oxidase in fungi," Applied and Environmental Microbiology, vol. 61, No. 12, pp. 4487-4489, XP000561863 ISSN: 0099-2240 (1995).

Norga, et al., "Prevention of Acute Autoimmune Encephalomyelitis and Abrogation of Relapses in Murine Models of Multiple Sclerosis by the Proteate inhibitor D-Penicillamine," Inflamm Res, vol. 44, No. 12, pp. 529-534 (1995).

Norton, et al., "Amioguanidine Prevents the Decreased Myocardial Compliance Produced by Streptozotocin-Induced Diabetes Mellitus in Rats," Circulation, 93, pp. 1905-1912 (1996).

Obach, et al., "The Pharmacokinetic Profile of Carbidopa in Dogs," J Pharm Pharmacol, 36, pp. 415-416 (1984).

Ou et al., "Erythrocyte Catalase Inactivation (H-20-2 production) by Ascorbic Acid and Glucose in the Presence of Aminotriazole: Role of Transition Metals and Relevance to Diabetes," Biochemical Journal, vol. 303, No. 3, pp. 935-940 Abstract (XP-002366430) (1994).

Ou, et al., "Activation of Aldose Reductase in Rat Lens and Metal-Ion Chelation by Aldose Reductase Inhibitors and Lipoic Acid," Free Rad. Res., vol. 25, No. 4, pp. 337-346 (1996).

Ou, et al., "Thioctic (Lipoic) Acid: A Therapeutic Metal-Chelating Antioxidant," Biochemical Pharmacology, vol. 50, No. 1, pp. 123-126 (1995).

Palcic, et al, "Spectrophotometric Detection of Topa Quinone," Meth Enzymol, 258, pp. 34-38 (1995).

Pappert et al., "The Stability of Carbidopa in Solution," Movement Disorders, 12, 4, pp. 608-623(1997).

Pasterkamp & Falk, "Atherosclerotic Plaque Rupture: an Overview," J. Clin. Basic Cardiel., 3, 81-86 (2000).

Picard, et al., "Minimally Oxidised LDL as Estimated by a New Method Increase in Plasma of Type 2 Diabetic Patients with Atherosclerosis of Nephropathy," Diabetes and Metabolism, 22, 1, pp. 25-30 (1996).

Pieper, et al., "Hydroxyl Radicals Mediate Injury to Endothelium-Dependent Relaxation in Diabetic Rat," Molecular and Cellular Biochemistry, 122, pp. 139-145 (1993).

Planas-Bohne, "Influence of Several Chelating Agents on the Excretion and Organ Concentration of Copper in the Rat," Toxicology and Applied Pharmacology, 50, pp. 337-345 (1979).

Pucheu, et al., "Effect of Iron Overload in the Isolated Ischemic and Reperfused Rat Heart," Cardiovascular Drugs and Therapy, 7, pp. 701-711 (1993).

Robbins, et al., "Pathologic Basis of Disease," 3.sup.rd ed., W. B. Saunders Company: Philadelphia, pp. 991-1061 (1984).

Rogers, et al., "Hydrazine Stress in the Diabetic: Ornithine Decarboxylase Activity," Biochemical Medicine and Metabolic Biology, 40, pp. 46-49 (1988).

Rossi, et al., "Increased Susceptibility of Copper-Deficient Neuroblastoma Cells to Oxidative Stress-Mediated Apoptosis," Free Radic Biol Med, vol. 30, No. 10, pp. 1177-1187 (2001).

Saeki, et al., "Malignant Syndrome Associated with Disseminated Intravascular Coagulation and a High Level of Amylase in Serum, Followed by Diabetic Coma in an Elderly Patient with Parkinson's Disease during L-Dopa Therapy," Nippon Ronen Igakkai Zasshi 35(2): 139-144. (English abstract) (1998).

(56) References Cited

OTHER PUBLICATIONS

Salonen, et al., "Serum Copper and the Risk of Acute Myocardial Infarction: A Prospective Population Study in Men in Eastern Finland," Am. J. Epidemiol, 134, pp. 268-76 (1991).

Saunders, "The Effects of Excess Renal Copper on Kidney Function in the Diabetic Rat," Research Communications in Chemical Pathology and Pharmacology, vol. 52, No. I, Apr. pp. 45-49 (1986).

Saxena, et al., "Purification and Characterization of a Membrane-bound Deglycating Enzyme {1-Deoxyfructosyl Alkyl Amino Acid Oxidase, EC 1.5.3) from a *Pseudomonas* sp. Soil Strain," J Biol Chem, 271, 51, pp. 32803-32809 (1996).

Shimizu et al., "Treatment and Management of Wilson's Disease," Pediatrics International, 41, pp. 419-422, (1999).

Shimizu, et al., "Age-Related Copper, Zinc, and Iron Metabolism in Long-Evans Cinnamon Rats and Copper-Eliminating Effects of S-Penicillamine and Trienthine-2HCl," The Journal of Trace Elements in Experimental Medicine, 10, pp. 49-59 (1997).

Skrha, et al., "Relationship of Oxidative Stress and Fibrinolysis in Diabetes Mellitus," Diabet. Med., 13, 9, pp. 800-805 (1996).

Smith, et al, "Trytophan and the Control of Plasma Glucose Concentrations in the Rat," Biochem J, 168, 3, pp. 495-506 (1977).

Smith, et al., "Mechanism of the Degradation of Non-Enzymatically Glycated Proteins under Physiological Conditions," Eur. J. Biochem., 210, pp. 729-739 (1992).

Somani, et al., "Elimination of superoxide dismutase interference in fructosamine assay," Clin. Biochem., 32, 3, pp. 185-188 (1999).

Sone, et al., "Inhibition of Hereditary Hepatitis and Liver Tumor Development in Long-Evans Cinnamon Rats by the Copper-Chelating Agent Trieritine Dihydrochloride," Hepatology, 23, 4, pp. 764-770 (1996).

Sone, et al., "Inhibition of Hereditary Hepatitis and Liver Tumor Development in Long-Evans Cinnamon Rats by the Copper-Chelating Agent Trientine Dihydrochloride," Hepatology, 23, 4, pp. 764-770 (1996).

Sugimoto, et al., "Advanced glycation end products-cytokine-nitric oxide sequence pathway in the development of diabetic nephraphathy: aminoguanidine ameliorates the overexpression of tumour necrosis factor-alpha and-inducible nitric oxide synthase in diabetic rat glomeruli," Diabetologia, 42, 7, pp. 878-886 (1999).

Sugimoto, et al., "Effects of Aminoguanidine on Structural Alterations of Microvessels in Peripheral Nerve of Streptozotocin Diabetic Rats", Microvascular Research 53, 105-112 (1997).

Talseth, "Kinetics of Hydralazine Elimination," Clinical Pharmacology Therapeutics, 21, 6, pp. 715-720 (1977).

Talseth, "Studies on Hydralazine," European Journal of Clinical Pharmacology, 10, 6, pp. 395-401 (1976).

Tanabe, et al., "Uptake Mechanism of Trientine by Rat Intestinal Brush-border Membrane Vesicles," J Pharm Pharmacol, 148, pp. 517-521 (1996).

Tandon, et al., "Effect of Meal Chelators Agent, Trientine, Suppresses tumor Development and Angiogenesis in the Murine Hepatocellular Carcinoma Cells," Int. J. Cancer, 94, pp. 768-773, (1984).

Tessier et al., "Effect of pH, phosphate and copper on the interaction of glucose with albumin," Glyconjugate Journal, 15, pp. 571-574 (1998).

The Diabetes Control and Complications Trial Research Group, "The Effect of Intensive Treatment of Diabetes on the Development and Progression of Long-term Complications in Insulin-dependent Diabetes Mellitus," N Eng J Med., 329, 14, pp. 977-986 (1993).

Toshihiko et al., "Subacute and Chronic Toxicity Studies of Triethylenetetramine Dihydrochloride (TJA-250) by Oral Administration to F-344 Rats," Journal of Toxicological Sciences, vol. 23, No. 4, pp. 619-642, Abstract (EP-002356395) (1998).

UKPDS Study Organisation, "Intensive Blood-glucose Control with Sulphonylureas or Insulin Compared with Conventional Treatment and Risk of Complications in Patients with Type 2 Diabetes (UKPDS 33)," Lancet, 352, pp. 837-853 (1998).

Vailly, et al., "Prevention of L-dopa of Early Renal Consequences of Diabetes Induced by Stepotozocin in Rats," Arch Mal Coeur Vaiss, 83, 8, pp. 1259-1262 (1990) (English abstract).

Vesely, et at., "New Strategies in the Prevention and Management of Diabetes and Its Complications," Online Journal, Jacksonville Medicine, downloaded from the Internet http://www.onlinejournal.com May 1997.

Walshe, "Treatment of Wilson's Disease with Trientine (Triethylene Tetramine) Dihydrochloride," Lancet, 8273 pp. 643-647 (1982).

Walshe, "Triethylene Tetramine Dihydrochloride in Wilson's Disease," Lancet, ii, pp. 1401(1969).

Walshe, et al., "Copper Chelation in Patients with Wilson's Disease: A Comparison of Penicillamine and Triethylene Tetramine Dihydrochloride," Q J Med New Series, XLII, 167, pp. 441-452 (1973).

Walter et al., "Copper, Zinc, Manganese, and Magnesium Status and Complications of Diabetes Mellitus," Diabetes Care, vol. 14, No. 11 (1991).

Wang, et al., "Adiponectin inhibits cell proliferation by interacting with several growth factors in an oligomerization-dependent manner," J Biol Chem, 280, 18, pp. 18341-18347, (Epub 2005).

Wang, et al., "Alteration in phosphorylation of P20 is associated with insulin resistance," Diabetes, 50, 8, pp. 1821-1827 (2001).

Wang, et al., "Amylin evokes phosphorylation of P20 in rat skeletal muscle," FEBS Lett, 457, 1, pp. 149-152 (1999).

Wang, et al., "Hydroxylation and glycosylation of the four conserved lysine residues in the collagenous domain of adiponectin. Potential role in the modulation of its insulin-sensitizing activity," J Biol Chem, 277, 22, pp. 19521-19529 (2002).

Wang, et al., "Phosphorylation of P20 is associated with the actions of insulin in rat skeletal and smooth muscle," Biochem J, 344 Pt, 3, pp. 971-976 (1999).

Wang, et al., "Proteomic and functional characterization of endogenous adiponectin purified from fetal bovine serum," Proteomics, 4, 12, pp. 3933-3942 (2004).

Aitken, et al., "Suppression by polycyclic compounds of the conversion of human amylin into insoluble amyloid," Biochem J, 374, Pt 3, pp. 779-784 (2003).

Allen, et al., "Tetramine Cupruretic Agents: a Comparison in Dogs," Am. J. Vet. Res., 48, 1, pp. 28-30 (1987).

American Diabetes Association, "Economic Consequences of Diabetes Mellitus in the U.S. in 1997," Diabetes Care, 21, 2, pp. 296-309 (1998).

Anaja, "Diagnostic performance of red cell sorbitol assay in a Nigerian teaching hospital," Clinica Chimica Acta, 262, 1, (1997).

Appelbaum, et al., "The Protective Role of Neocuproine Against Cardiac Damage in Isolated, Perfused Rat Hearts," Free Radical Biology & Medicine, vol. 8, pp. 133-143 (1990).

Armbruster, "Fructosamine Structure Analysis and Clinical Usefulness" Clinical Chemistry, vol. 33, No. 12, pp. 2153-2163, XP001061531 ISSN: 0009-9147 (1987).

Baker, et al, "Mechanism of fructosamine assay: evidence against role of superoxide as intermediate in nitroblue tetrazolium reduction," Clin Chem, 39, 12, pp. 2460 (1993).

Barthelmebs, et al., "Effects of Dopamine Pro-drugs and Fenoldopam on Glomerular Hyperfiltration in Streptozotocin-Induced Diabetes in Rats", Journal of Cardiovascular Pharmacology, 18, 2, pp. 243-253 (1991).

Barthelmebs, et al., "L-Dopa and Streptozotocin-Induced Diabetic Nephropathy in Rats," American Journal of Hypertension, 3, 6, Part 2, pp. 72S-74S (1990).

Barthlmebs, et al., "Pathophysiological Role of Dopamine in the Kidney: Effects in Diabetes Mellitus and after Contralateral Nephrectomey," Hypertens. Res., 18 (Suppl. I), pp. S131-S136 (1995).

Baynes, "Role of Oxidative Stress in Development of Complications in Diabetes," Diabetes, 40, pp. 405-412 (1991).

Berenshtein, et al., "Roles of Ferritin and Iron in Ischemic Preconditioning of the Heart," Molecular and Cellular Biochemistry, 234/235, pp. 283-292, Kluwer Academic Publishers, Netherlands (2002).

Beshgetoor, et al., "Clinical conditions altering cooper metabolism in humans," Am J Clio Nutr, 67 (suppl), 10, pp. 17S-21S (1998).

(56) References Cited

OTHER PUBLICATIONS

Bingham, et al., "Characterization of intracellular copper pools in rat hepatocytes using the chelator diamsar," Am. J. Physiol. , 272 (Gastrointest. Liver Physiol. 35), pp. G1400-G 1407, (1997).
Boiadzhieva, "The Effect of Dopaminergic Pharmocological Agents on the Pancreatic Islet Apparatus in Rats," Eksp Med Morfol, 29, 3, pp. 20-26 (English abstract) (1990).
Borgstrom, et al., "Pharmacokinetics of N-Acetylcysteine in Man," Eur J Clin Pharmacol, 31, pp. 217-222 ( 1986).
Borthwick, et al., "Copper Chelating Agents: A Comparison of Cupruretic Responses to Various Tetramines and D-Penicillamine," J. Lab. Clin. Med. 95(4):575-580 (1980).
Brems, "Angiogenesis and Cancer Control: From Concept to Therapeutic Trial," Cancer Control, vol. 6, No. 5, pp. 436-458 (1999).
Brownlee, et al., "Aminoguanidine Prevents Diabetes-Induced Arterial Wall Protein Cross-Linking," Science, New Series, vol. 232, No. 4758, pp. 1629-1632, (1986).
Bryszewska, et al., "Oxidative Processes in Red Blood Cells from Normal and Diabetic Individuals," Biochemistry and Molecular Biology International, vol. 37, No. 2, pp. 345-354 (1995).
Buchanan, et al., Preptin derived from proinsulin-like growth factor II (proIGF-II) is secreted from pancreatic islet beta-cells and enhances insulin secretion, Biochem J, 360(Pt 2), pp. 431-439 (2001).
Cameron, et al., "Ciliary Neurontrophic Factor Improves Nerve Conduction and Regeneration in Experimental Diabetes," Diabetologia, 38 (Suppl. I), A233 Abstract (1995).
Chan, et al., "Enzyme-catalyzed Free Radical Reactions with nicotinamide Adenine Nucleotides," J Biol Chem, 249, 4, pp. 1317-1319 (1974).
Chan, et al., "Giyceraldehyde-3-Phosphate Dehydrogenase-catalyzed Chain Oxidation of Reduced Nicotinamide Adenine Dinucleotide by Perhydroxyl Radicals," J Biol Chem, 255, 3, pp. 874-876 (1980).
Chang, et al., "Increased Collagen Cross-Linkages in Experimental Diabetes Reversal by β-Aminopropionitrile and D-Penicillamine," Diabetes, vol. 29, pp. 778-781, (1980).
Chaturvedi, et al., "Effect of Lisinopril on Progression of Retinopathy in Normotensive People with Type I Diabetes," The Lancet, 351, pp. 28-31 (1998).
Cherny, et al., "Chelation and Interaction: Complementary Properties in a Compound for the Treatment of Alzheimer's Disease," J Struct Biol, vol. 130, No. 23, pp. 209-216 (2000).
Chiara, et al, "Novel Degradation Pathway of Glycated Amino Acids into Free Fructosamine by a *Pseudomonas* sp. Soil Strain Extract," Journal of Biological Chemistry, vol. 270, No. 1, pp. 218-224, XP002189588 ISSN: 218-224 (1995).
Cohen, et al. "The Effect of Copper Chelating Drugs on Liver Iron Mobilization in the Adult Rat," Biochemical and Biophysical Research Communications, 113, 1, pp. 127-134 (1983).
Cooper, "Amylin and insulin co-replacement therapy for insulin-dependent (type I) diabetes mellitus," Med Hypotheses, 36, 3, pp. 284-288 (1991).
Cooper, "The Action of Mebanazine, a Mono Amine Oxidase Inhibitor Antidepressant Drug in Diabetes," Int. J. Neurophyschiatry, 4, pp. 342-345 (1966).
Cooper, et al., "Amylin, amyloid and age-related disease," Drugs Aging, 9, 3, pp. 202-212 (1996).
Cooper, et al., "Demonstration of a hyperglycemia-driven pathogenic abnormality of copper homeostasis in diabetes and its reversibility by selective chelation: quantitative comparisons between the biology of copper and eight other nutritionally essential elements in normal and diabetic individuals," Diabetes, 54, 5, pp. 1468-1476 (2005).
Cooper, et al., "Regeneration of the heart in diabetes by selective copper chelation," Diabetes, 53, 9, pp. 2501-2508 (2004).
Cornish, et al., "Effects of calcitonin, amyl in, and calcitonin gene-related peptide on osteoclast development," Bone, 29, 2, pp. 162-168 (2001).
Cunnane, et al., "Copper Inhibits Pressor Responses to Noradrenaline but not Potassium Interactions with Prostaglandins E1. E2, and hand Penicillamine," Can. J. Physiol. Pharmacal. vol. 57, pp. 35-40 (1979).
Dahlman, et al., "Long-term treatment of Wilson's disease with triethylene tetramine dihydrochloride (trientine)," YJM, 9=88, 9, pp. 609-616 (2000).
Deckert et al., "Prognosis of Diabetics with Diabetes Onset before the Age of Thirtyone," Diabetologia, 14, pp. 363-370 (1978).
Dubois, et al., Triethylene Teramine Dihydrochloride in Wilson's Disease, Lancet, 2, 7676, pp. 775 (1970).
Duchin, et al., "Pharmacokinetics of Captopril in Healthy Subjects and in Patients with Cardiovascular Diseases," Clin Pharmacokinetics, 14, pp. 241-259 (1988).
Duffy et al., "Iron Chelation Improves Endothelial Function in Patients with Coronary Artery Disease," Circulation, 103, pp. 2799-28204 (2001).
Dwivedi, et al., "The Effect of Triethylene Tetramine Upon the Selective Removal of Nickel (II), Iron (II), Manganese (II) and Tin (ID in Rats," Chemosphere, 11, pp. 925-932(1978).
Eizirik, et al., "1, 10 Phenanthroloine, a Metal Chelator, Protects Against Alloxan—but not Streptozotocin-Induced Diabetes," Journal of Free Radicals in Biology & Medicine, vol. 2, pp. 189-192 (1986).
Ekblom, "Potential Therapeutic Value of Drugs Inhibiting Semicarbazide-Sensitive Amine Oxidase: Vascular Cytoprotection in Diabetes Mellitus," Pharmacological Research, vol. 37, No. 2 (1998).
Elling, "Penicillamine, Captopril, and Hypoglycemia," Annals of Internal Medicine, vol. 103, No. 4 (1985).
Elstner, et al., "Inhibition of Nitrite Formation from Hydroxylammonium-chloride: A Simple Assay for Superoxide Dismutase," Anal Biochem, 70, pp. 616-620 (1976).
Encyclopedia of Toxicology, vol. 1, Philip Wexler, ed. published 1998 by Academic Press (San Diego) pp. 376-378.
Epstein, et al., "Triethylene Tetramine Dihydrochloride Toxicity in Primary Biliary Cirrhosis," Gastroenterology, 78, 6, pp. 1442-1445 (1980).
Failla et al., "Altered Tissue Content and Cytosol Distribution of Trace Metals in Experimental Diabetes," Journal of Nutrition, vol. III, No. 11, pp. 1900-1909 (1981) Abstract (XP-002366429).
Failla, et al., "Hepatic and Renal Metabolism of Copper and Zinc in the Diabetic Rat," American Journal of Physiology, vol. 244, No. 2, pp. E115-E121 (1983) Abstract (XP-002366428).
Witek, et al., "Polycondensation of polyethylenepolyamines with aliphatic dicarboxylic acids," Polymers-Large Molecule Materials, The Institute of Polymers, The Lodz Polytechnic (1976).
Witztum, "Role of Oxidised Low Density Lipoprotein in Atherogenesis," Br Heart J, 69 (Suppl), pp. S12-S18 (1993).
Wolff, "Diabetes Mellitus and Free Radicals", British Medical Bulletin, vol. 49, No. 3, pp. 642-652 (1993).
Wolff, "Protein Glycation and Oxidative Stress in Diabetes Mellitus and Ageing," Free Rad Bioi Med, 10, pp. 339-352 (1991).
Wolff, et al., "Aminoguanidine is an Isoform-Selective, Mechanism-Based Inactivator of Nitric Oxide Synthase", Archives of Biochemistry and Biophysics, vol. 316, No. 1, Jan. 10, pp. 290-301 (1995).
Wolff, et al., "Inactivation of Nitric Oxide Synthase by Substituted Aminoguanidines and Aminoisothioureas," JPET, 283, pp. 265-273, 1997.
Wynn, "The Toxicity and Pharmacodynamics of EGTA: Oral Administration to Rats and Comparisons with EDTA," Toxicol Appl Pharmacol, 16, pp. 807-817 (1970).
Xu, et al., "The fat-derived hormone adiponectin alleviates alcoholic and nonalcoholic fatty liver diseases in mice," J Clin Invest, 112, 1, pp. 91-100 (2003).
Xu, et al, "Identification of novel putative membrane proteins selectively expressed during adipose conversion of 3T3-Li cells," Biochem Biophys Res Commun, 17, 293, 4, pp. 1161-1167 (2002).
Xu, et al., "Chronic treatment with growth hormone stimulates adiponectin gene expression in 3T3-Li adipocytes," FEBS Lett, 572, 1-3, pp. 129-134 (2004).
Xu, et al., "Testosterone selectively reduces the high molecular weight form of adiponectin by inhibiting its secretion from adipocytes," J Biol Chem, 280, 18, pp. 18073-18080, (Epub 2005).

(56) References Cited

OTHER PUBLICATIONS

Yagihashi, et al., "Effect of Aminoguanidine on Functional and Structural Abnormalities in peripheral Nerve of STZ-Induced Diabetic Rats," Diabetes, vol. 41, pp. 47-52 (1992).

Yanagisawa, "Subacute and chronic toxicity studies of triethylenetetramine dihydrochloride (TJA-250) by oral administration to F-344 rats," J. Toxicol. Sci., 23 Suppl., 4, pp. 619-642.

Yoshii, et al., "The Copper-Chelating Agent, Trientine, Suppresses Tumor Development and Angiogenesis in the Murine Hepatocellular Carcinoma Cells," Int. J. Cancer, 94, pp. 768-773 (2001).

Young et at., "The Effects of Desferrioxamine and Ascorbate on Oxidative Stress in the Streptozotocin Diabetic Rat," Free Radical Biology & Medicine, vol. 18, No. 5, pp. 833-840 (1995).

Yu et al., "Aminoguanidine inhibits semicarbazide-sensitive amine oxidase activity: implications for advanced glycation and diabetic complications," Diabetologia, 40, pp. 1243-1250 (1997).

Yucel, et al., "Increased Oxidative Stress in Dilated Cardiomyopathic Heart Failure," Clin Chem, 44, 1, pp. 148-154 (1998).

Cameron, et al., "Neurovascular Dysfunction in Diabetic Rats, Potential Contribution of Autoxidation and Free Radicals Examined Using Transition Metal Chelating Agents," J. Clin. Invest 96(2): 1159-1163 (1995).

Wang, et al., Insulin and insulin antogonists evoke phosphorylation of P20 at serine 157 and serine 16 respectively in rat skeletal muscle, FEBS Lett 1999; 462(1-2):2530.

American Diabetes Association, "Report of the Expert Committee on the Diagnosis and Classification of Diabetes Mellitus," Diabetes Care 20:1183 (1997).

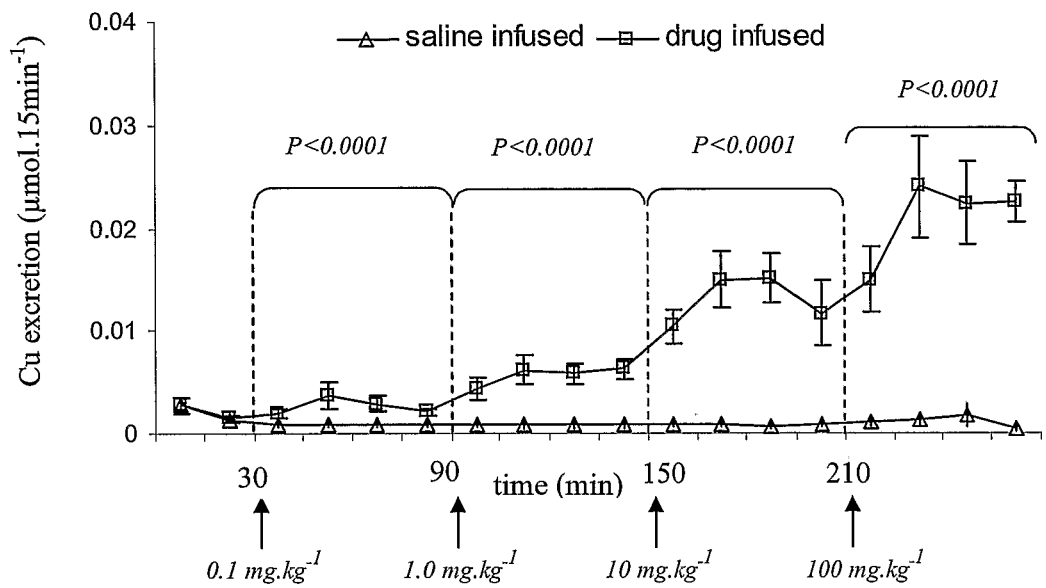
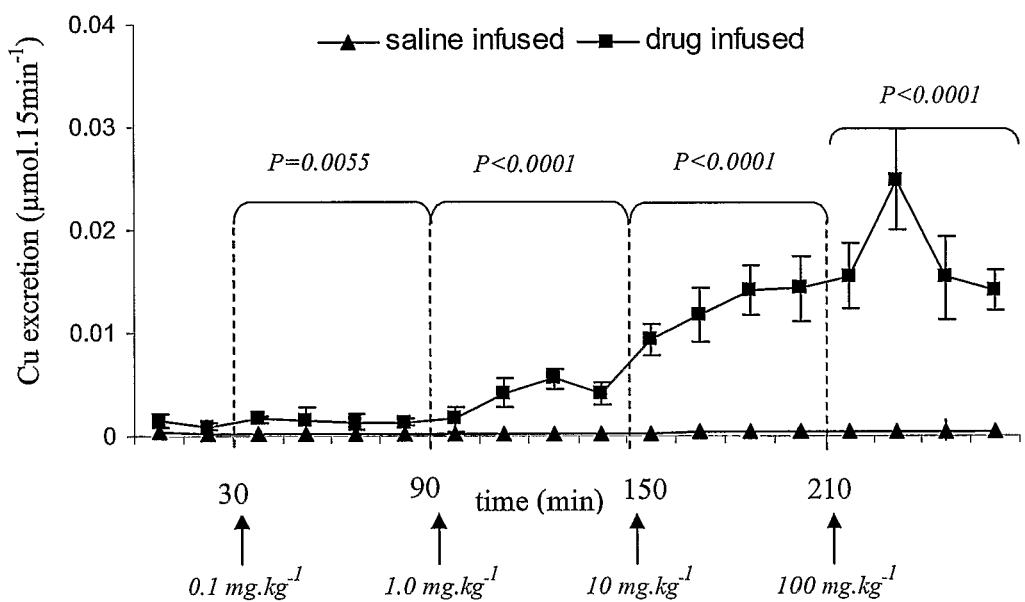
FIGURE 3

| Cu excretion | | Dose level | | |
|---|---|---|---|---|
| Mixed Model Effects | Baseline | 0.1 mg.kg$^{-1}$ | 1.0 mg.kg$^{-1}$ | 10 mg.kg$^{-1}$ | 100 mg.kg$^{-1}$ |
| Diabetes | $F_{1,24} = 18.52$ | $F_{1,24} = 19.82$ | $F_{1,24} = 21.92$ | $F_{1,24} = 9.93$ | $F_{1,24} = 17.82$ |
| (normal/diabetic rats) | $P = 0.0002$ | $P = 0.0002$ | $P < 0.0001$ | $P < 0.0001$ | $P < 0.0003$ |
| Drug | $F_{1,24} = 1.73$ | $F_{1,24} = 24.94$ | $F_{1,24} = 78.36$ | $F_{1,24} = 135.36$ | $F_{1,24} = 162.17$ |
| (drug/saline) | NS | $P < 0.0001$ | $P < 0.0001$ | $P < 0.0001$ | $P < 0.0001$ |
| Interaction | $F_{1,24} = 0.16$ | $F_{1,24} = 3.58$ | $F_{1,24} = 7.16$ | $F_{1,24} = 6.02$ | $F_{1,24} = 12.43$ |
| | NS | NS | $P < 0.0132$ | $P < 0.0218$ | $P < 0.0017$ |
| Sampling time (repeated measure) | $t_1, t_2$ | $t_1, t_2, t_3, t_4$ | $t_1, t_2, t_3, t_4$ | $t_1, t_2, t_3, t_4$ | $t_1, t_2, t_3, t_4$ |

| Fe excretion | | Dose level | | |
|---|---|---|---|---|
| Mixed Model Effects | Baseline | 0.1 mg.kg$^{-1}$ | 1.0 mg.kg$^{-1}$ | 10 mg.kg$^{-1}$ | 100 mg.kg$^{-1}$ |
| Diabetes | $F_{1,23} = 12.87$ | $F_{1,23} = 15.82$ | $F_{1,24} = 22.68$ | $F_{1,24} = 14.93$ | $F_{1,24} = 7.35$ |
| (normal/diabetic rats) | $P = 0.0016$ | $P = 0.0006$ | $P < 0.0001$ | $P = 0.0007$ | $P = 0.0122$ |
| Drug | $F_{1,23} = 8.6$ | $F_{1,23} = 7.89$ | $F_{1,24} = 12.23$ | $F_{1,24} = 10.91$ | $F_{1,24} = 2.47$ |
| (drug/saline) | $P = 0.0075$ | $P = 0.01$ | $P < 0.0019$ | $P = 0.003$ | $P = 0.1292$ |
| Interaction | $F_{1,23} = 12.10$ | $F_{1,23} = 15.06$ | $F_{1,24} = 14.07$ | $F_{1,24} = 17.72$ | $F_{1,24} = 16.76$ |
| | $P = 0.002$ | $P = 0.0008$ | $P = 0.001$ | $P = 0.0003$ | $P = 0.0004$ |
| Sampling time (repeated measure) | $t_1, t_2$ | $t_1, t_2, t_3, t_4$ | $t_1, t_2, t_3, t_4$ | $t_1, t_2, t_3, t_4$ | $t_1, t_2, t_3, t_4$ |

Figure 12 p<0.05: STZ v STZ/D7

$p<0.05$: STZ v STZ/D7, #.$p<0.05$: STZ/D7 v Sham/D7.

p<0.05: STZ v STZ/D7 p<0.05: STZ v STZ/D7, #.p<0.05: STZ/D7 v Sham/D7.

Wilcoxon p<0.05 for STZ v STZ/D7

DOSAGE FORMS AND RELATED THERAPIES

FIELD OF THE INVENTION

The subject invention pertains to doses and dosage forms of therapeutic agents and their use in methods for the treatment, reversal or amelioration of diseases, disorders and/or conditions in a mammal (hereafter "treating"). Mammals that may be treated using the described and claimed doses and dosage forms include, for example, a human being having, or at risk for developing, microvascular and/or macrovascular damage, for example, cardiovascular tissue damage and, in particular, mammals including human beings that have or are at risk for developing undesired copper levels, including copper levels that can cause or lead to tissue damage, including but not limited to vessel damage. Treatment includes but is not limited to therapies to ameliorate and/or reverse, in whole or in part, damage resulting from diseases, disorders or conditions that are characterized in any part by copper-involved or mediated damage of tissue and/or vasculature, and/or to copper-involved or mediated impairment of normal tissue stem cell responses. The invention has application inter alia, for example, to diabetes-related and non-diabetes-related heart failure, macrovascular disease or damage, microvascular disease or damage, and/or toxic (e.g., hypertensive) tissue and/or organ disease or damage (including such ailments as may, for example, be characterized by heart failure, cardiomyopathy, myocardial infarction, and related arterial and organ diseases) by administration of an active copper-chelating compound such as, for example, one or more of trientine, salts of trientine, prodrugs of trientine and salts of such prodrugs, analogs of trientine and salts and prodrugs of such analogs, and/or active metabolites of trientine and salts and prodrugs of such metabolites, including but not limited to N-acetyl trientine and salts and prodrugs of N-acetyl trientine.

BACKGROUND

The following description includes information that may be useful in understanding the present invention. It is not an admission that any of the information provided herein is prior art, or relevant, to the presently described or claimed inventions, or that any publication or document that is specifically or implicitly referenced is prior art or a reference that may be used in evaluating patentability of the described or claimed inventions.

Diabetes mellitus is a chronic condition characterized by the presence of fasting hyperglycemia and the development of widespread premature atherosclerosis. Patients with diabetes have increased morbidity and mortality due to cardiovascular diseases, especially coronary artery disease. Vascular complications in diabetes may be classified as microvascular, affecting the retina, kidney and nerves and macrovascular, predominantly affecting for example coronary, cerebrovascular and peripheral arterial circulation.

The chronic hyperglycemia of diabetes is associated with long-term damage, dysfunction, and failure of various organs, especially the eyes, kidneys, nerves, heart, and blood vessels and long-term complications of diabetes include retinopathy with potential loss of vision; nephropathy leading to renal failure; peripheral neuropathy with risk of foot ulcers, amputation, and Charcot joints; and autonomic neuropathy causing gastrointestinal, genitourinary, and cardiovascular symptoms and sexual dysfunction.

Glycation of tissue proteins and other macromolecules and excess production of polyol compounds from glucose are among the mechanisms thought to produce tissue damage from chronic hyperglycemia. Diabetic patients have an increased incidence of atherosclerotic cardiovascular, peripheral vascular, and cerebrovascular disease. Hypertension, abnormalities of lipoprotein metabolism, and periodontal disease are also found in people with diabetes.

Hyperglycemia induces a large number of alterations in vascular tissue that potentially promote accelerated atherosclerosis. Currently, in addition to the nonenzymatic glycosylation of proteins and lipids, two other major mechanisms have emerged that encompass most of the pathologic alterations observed in the vasculature of diabetic animals and humans, namely, oxidative stress and protein kinase C (PKC) activation. These mechanisms are not independent. For example, hyperglycemia-induced oxidative stress promotes the formation of AGEs and PKC activation, and both type 1 and type 2 diabetes are independent risk factors for coronary artery disease (CAD), stroke, and peripheral arterial disease. Schwartz C. J., et al., "Pathogenesis of the atherosclerotic lesion. Implications for diabetes mellitus," *Diabetes Care* 15:1156-1167 (1992); Stamler J., et al., "Diabetes, other risk factors, and 12-yr cardiovascular mortality for men screened in the Multiple Risk Factor Intervention Trial." *Diabetes Care* 16:434-444 (1993). Atherosclerosis accounts for virtually 80% of all deaths among North American diabetic patients, compared with one-third of all deaths in the general North American population, and more than 75% of all hospitalizations for diabetic complications are attributable to cardiovascular disease. American Diabetes Association, "Consensus statement: role of cardiovascular risk factors in prevention and treatment of macrovascular disease in diabetes," *Diabetes Care* 16:72-78 (1993).

The decline in heart disease mortality in the general U.S. population has been attributed to the reduction in cardiovascular risk factors and improvement in treatment of heart disease. However, patients with diabetes have not experienced the reduction in age-adjusted heart disease mortality that has been observed in nondiabetics, and an increase in age-adjusted heart disease mortality has been reported in diabetic women. Gu K, et al., "Diabetes and decline in heart disease mortality in U.S. adults," *JAMA* 281:1291-1297 (1999). It has also been reported that diabetic subjects have more extensive atherosclerosis of both coronary and cerebral vessels than age- and sex-matched nondiabetic controls. Robertson W. B., & Strong J. P., "Atherosclerosis in persons with hypertension and diabetes mellitus,"*Lab Invest* 18:538-551 (1968). Additionally, it has been reported that diabetics have a greater number of involved coronary vessels and more diffuse distribution of atherosclerotic lesions. Waller B. F., et al., "Status of the coronary arteries at necropsy in diabetes mellitus with onset after age 30 years. Analysis of 229 diabetic patients with and without clinical evidence of coronary heart disease and comparison to 183 control subjects," *Am J Med* 69:498-506 (1980).

Following large studies comparing diabetics with matched controls, it has also been reported that diabetic patients with established CAD undergoing cardiac catheterization for acute myocardial infarction, angioplasty, or coronary bypass have significantly more severe proximal and distal CAD. Granger C. B., et al., "Outcome of patients with diabetes mellitus and acute myocardial infarction treated with thrombolytic agents. The Thrombolysis and Angioplasty in Myocardial Infarction (TAMI) Study Group," *J Am Coll Cardiol* 21:920-925 (1993); Stein B., et al., "Influence of diabetes mellitus on early and late outcome after percutaneous transluminal coronary angioplasty," *Circulation* 91:979-989 (1995); Barzilay J. I., et al., "Coronary artery disease and coronary artery bypass grafting in diabetic patients aged> or =65 years [from the Coronary Artery Surgery Study (CASS) Registry]," *Am J Cardiol* 74:334-339(1994)). Postmortem and angioscopic evidence also shows a significant increase in plaque ulceration and thrombosis in diabetic patients. Davies M. J., et al., "Factors influencing the presence or absence of acute coronary artery thrombi in sudden ischemic death," *Eur Heart J* 10; 203-208 (1989); Silva J. A., et al. "Unstable angina. A comparison of angioscopic findings between diabetic and nondiabetic patients," *Circulation* 92:1731-1736 (1995).

CAD is the leading cause of death in people with type 2 diabetes, regardless of duration of diabetes. Stamler I., et al., "Diabetes, other risk factors, and 12-yr cardiovascular mortality for men screened in the Multiple Risk Factor Intervention Trial," *Diabetes Care* 16:434-444 (1993); Donahue R. P., & Orchard T. J., "Diabetes mellitus and macrovascular complications. An epidemiological perspective," *Diabetes Care* 15:1141-1155 (1992). The increased cardiovascular risk is said to be particularly striking in women. Barrett Connor E. L., et al., "Why is diabetes mellitus a stronger risk factor for fatal ischemic heart disease in women than in men? The Rancho Bernardo Study," *JAMA* 265:627-631 (1991). CAD is not confined to particular forms of diabetes, however, and is prevalent in both type 1 and type 2 diabetes. In type 1 diabetes, an excess of cardiovascular mortality is generally observed after the age of 30. Krolewski A. S., et al., "Magnitude and determinants of coronary artery disease in juvenile-onset, insulin-dependent diabetes mellitus," *Am J Cardiol* 59:750-75 5 (1987). CAD risk was reported in this study to increase rapidly after age 40, and by age 55, 35% of men and women with type 1 diabetes die of CAD, a rate of CAD mortality that far exceeded that observed in an age-matched nondiabetic cohort. Id.

Diabetic nephropathy in type 1 diabetics also increases the prevalence of CAD. Nephropathy leads to accelerated accumulation of AGEs in the circulation and tissue and parallels the severity of renal functional impairment. Makita Z., et al., "Advanced glycosylation end products in patients with diabetic nephropathy," *N Engl J Med* 325:836-842 (1991). In diabetic patients reaching end-stage renal disease, overall mortality has been reported to be greater than in nondiabetic patients with end-stage renal disease. The relative risk for age-specific death rate from myocardial infarction among all diabetic patients during the first year of dialysis is reportedly 89-fold higher than that of the general population. Geerlings W., et al., "Combined report on regular dialysis and transplantation in Europe, XXI," *Nephrol Dial Transplant* 6 41:5-29 (1991). It has also been reported that the most common cause of death in diabetic patients who have undergone renal transplantation is CAD, accounting for 40% of deaths in these patients. Lemmers M. J., & Barry J. M., "Major role for arterial disease in morbidity and mortality after kidney transplantation in diabetic recipients," *Diabetes Care* 14:295-301 (1991).

It has been demonstrated that the degree and duration of hyperglycemia are the principal risk factors for microvascular complications in type 2 diabetes. The Diabetes Control and Complications Trial Research Group, "The effect of intensive treatment of diabetes on the development and progression of long-term complications in insulin-dependent diabetes mellitus," *N Eng J Med* 329:977-986 (1993). However, it has also been said that there is no clear association between the extent or severity of macrovascular complications and the duration or severity of the diabetes, and an increased prevalence of CAD is apparent in newly diagnosed type 2 diabetes subjects has been reported. Uusitupa M., et al., "Prevalence of coronary heart disease, left ventricular failure and hypertension in middle-aged, newly diagnosed type 2 (non-insulin dependent) diabetic subjects," *Diabetologia* 28:22-27 (1985). It has also been reported that even impaired glucose tolerance carries an increased cardiovascular risk despite minimal hyperglycemia. Fuller J. H., et al., "Coronary-heart-disease risk and impaired glucose tolerance. The Whitehall study," *Lancet* 1:1373-1376 (1980).

There is also a worldwide trend towards an increasing prevalence of diabetes. The number of cases of type 2 diabetes is projected to increase from 135 million in 2000 to more than 300 million in 2025. This increase is related to an ageing of the population, increasing obesity, and low socio-economic status. See, WHO. The World Health Report 1997. As a consequence, mortality from diabetes has increased over the last decade whereas mortality from cardiovascular disease, stroke, and malignant diseases has remained static or declined. See, U.S. Center for Health Studies. The causes of premature mortality in type 2 diabetes comprise cardiovascular disease, 58%; cerebrovascular disease, 12%; nephropathy, 3%; diabetic coma, 1%; and malignancy, 11%.

Diabetic heart disease is further characterized by more severe CAD at a younger age, a 4-fold increase in frequency of heart failure, post-acute myocardial infarction and a disproportionate increase in left ventricular hypertrophy. See Struthers A. D., & Morris A. D., *Lancet* 359:1430-2 (2002). Subjects with type 2 diabetes also manifest a disproportionate increase in mortality within the first 24-hours post-acute myocardial infarction. Acute intervention can ameliorate this risk. See, Malmberg K., *Br Med J* 314:1512-5 (1997).

PCT Application No. PCT/NZ99/00161 (published as WO00/18392 on 6 Apr. 2000) relates to methods of treating a mammalian subject predisposed to and/or suffering from diabetes mellitus with a view to minimizing the consequences of macrovascular and microvascular damage to the patent which comprises, in addition to any treatment in order to control blood glucose levels, at least periodically controlling copper, for example, in the subject. An assay method is disclosed in PCT Application No. PCT/NZ99/00160 (published as WO00/18891 on 6 Apr. 2000). A range of different treatment agents are disclosed in PCT/NZ99/00161. These included copper chelating agents.

Metals are present naturally in the body and many are essential for cells (e.g., Cu, Fe, Mn, Ni, Zn). However, all metals are toxic at high concentrations. One reason metals may become toxic relates to their ability to cause oxidative stress, particularly redox active transition metals, which can take up or give off an electron (e.g., $Fe2+/3+$, $Cu+/2\pm$) that can give rise to free radicals that cause damage (Jones et al., "Evidence for the generation of hydroxyl radicals from a chromium (V) intermediate isolated from the reaction of chromate with glutathione," *Biochim. Biophys. Acta* 286:652-655 (1991); Li, Y. & Trush, M. A., DNA damage resulting from the oxidation of hydroquinone by copper: role for a Cu(II)/Cu(I) redox cycle and reactive oxygen generation," *Carcinogenes* 7:1303-1311 (1993)). Metals can replace other essential metals or enzymes, disrupting the function of these molecules, and can be toxic for this reason as well. Some metal ions (e.g., $Hg+$ and $Cu+$) are very reactive to thiol groups and may interfere with protein structure and function.

As noted herein, humans subject to type 2 diabetes or abnormalities of glucose mechanism are particularly at risk to the precursors of heart failure, heart failure itself, and other diseases of the arterial tree. It has been reported that more than 50% of patients with type 2 diabetes in Western countries die from the effects of cardiovascular disease. See, Stamler, et al., *Diabetes Care* 16:434-44 (1993). It has also been reported that even lesser degrees of glucose intolerance defined by a glucose tolerance test (impaired glucose tolerance, or "IGT") still carry an increased risk of sudden death. See, Balkau, et al., *Lancet* 354:1968-9 (1999). For a long time, it was assumed that this reflected an increased incidence of coronary atherosclerosis and myocardial infarction in diabetic subjects. However, evidence is mounting that diabetes can cause a specific heart failure or cardiomyopathy in the absence of atherosclerotic coronary artery disease.

Cardiac function is commonly assessed by measuring the ejection fraction. A normal left ventricle ejects at least 50% of its end-diastolic volume each beat. A patient with systolic heart failure commonly has a left ventricular ejection fraction less than 30% with a compensatory increase in end-diastolic volume. Hemodynamic studies conducted on diabetic subjects without overt congestive heart failure have observed normal left ventricular systolic function (LV ejection fraction) but abnormal diastolic function suggesting impaired left ventricular relaxation or filling. See Regan, et al., *J. Gun. Invest.* 60:885-99 (1977). In a recent study, 60% of men with type 2 diabetes without clinically detectable heart disease were reported to have abnormalities of diastolic filling as assessed by echocardiography. See Poirier, et al., *Diabetes Care* 24:5-10 (2001). Diagnosis maybe made, for example, by non-invasive measurements. In the absence of mitral stenosis, mitral diastolic blood flow measured by Doppler echocardiography is a direct measure of left ventricular filling. The most commonly used measurement is the AlE ratio. Normal early diastolic filling is rapid and is characterized by an E-wave velocity of around 1 m/sec. Late diastolic filling due to atrial contraction is only a minor component, and the A-wave velocity is perhaps around 0.5 m/sec. This gives a normal AIE ratio of approximately 0.5. With diastolic dysfunction, early diastolic filling is impaired, atrial contraction increases to compensate, and the AlE ratio increases to more than 2.0.

Treatment, let alone reversal or amelioration, of diabetic cardiomyopathy is difficult and the options are limited. Tight control of blood glucose levels might prevent or reverse myocardial failure, although this may be true only in the early stages of ventricular failure. Angiotensin converting enzyme inhibitors such as captopril improve survival in heart failure particularly in patients with severe systolic heart failure and the lowest ejection fractions. There are, however, various therapies that are not recommended for diabetic cardiomyopathy. For example, inotropic drugs are designed to improve the contraction of the failing heart. However, a heart with pure diastolic dysfunction is already contracting normally and it is believed that inotropic drugs will increase the risk of arrhythmias. Additionally, there appears to be no basis for the use vasodilator drugs that reduce after-load and improve the emptying of the ventricle because ejection fraction and end-diastolic volume are already normal. After-load reduction may even worsen cardiac function by creating a degree of outflow obstruction.

Diuretics are the mainstay of therapy for heart failure by controlling salt and water retention and reducing filling pressures. However, they are contraindicated in diastolic dysfunction where compromised cardiac pump function is dependent on high filling pressures to maintain cardiac output. Venodilator drugs such as the nitrates, which are very effective in the management of systolic heart failure by reducing pre-load and filling pressures, are understood to be poorly tolerated by patients with diastolic heart failure. Ejection fraction and end-systolic volume are often normal and any reduction in pre-load leads to a marked fall in cardiac output. Finally, there is concern about the use of beta-blockers in heart failure because of their potential to worsen pump function. There is also concern regarding the administration of beta-blockers to patients with diabetes who are treated with sulphonylurea drugs and insulin due to a heightened risk of severe hypoglycaemia.

Thus, it will be understood that the mechanisms underlying various disorders of the heart, the macrovasculature, the microvasculature, and the long-term complications of diabetes, including associated heart diseases and conditions and long-term complications, are complex and have long been studied without the discovery of clear, safe and effective therapeutic interventions. There is a need for such therapies, which are described and claimed herein.

It is also understood there is a continuing need for pharmaceutical compositions capable of addressing damage arising from disease states, disorders or conditions of the cardiovascular tree (including the heart) and dependent organs (e.g., retina, kidney, nerves, etc.) that involve, concern or relate to, for example, elevated or undesired copper levels such as elevated non-intracellular free copper values levels. The described and claimed therapies also provide low dose controlled release and/or low dose extended release compositions useful for the reversal and/or amelioration of structural damage in a subject whether diabetic or not, having copper levels capable of diminishment in order to treat, for example, the heart, the macrovasculature, the microvasculature, and/or long-term complications of diabetes, including cardiac structure damage. Cardiac structure damage includes, but is not limited to, for example, atrophy, loss of myocytes, expansion of the extracellular space and increased deposition of extracellular matrix (and its consequences) and/or coronary artery structure damage selected from at least media damage (the muscle layer) and intima damage (the endothelial layer) (and its consequences), systolic function, diastolic function, contractility, recoil characteristics and ejection fraction.

Diseases, disorders and conditions relating to the cardiovascular tree and/or dependent organs that may be treated by the methods and compositions of the present invention include, for example, any one or more of (1) disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; (2) atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; (3) toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, (4) plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

SUMMARY OF THE INVENTION

The present invention is based, in part, on new doses and dosage forms for treatments aimed at reduction in available free copper that are useful, for example, in treating and preventing macrovascular, microvascular and/or toxic/metabolic diseases of the kind referenced herein and in tissue repair processes. This is irrespective of the glucose metabolism of the subject and irrespective of whether or not fructosamine oxidase is involved in any such disease. The invention also relates to doses and dosage forms of treatments relating to the cardiovascular accumulation of redox-active transition metal ions in diabetes.

Under physiological conditions, injury to a target organ is sensed by distant stem cells that migrate to the site of damage and undergo alternate stem cell differentiation to assist in structural and functional repair. The doses and dosage forms of treatments described herein will also alleviate the accumulation of redox-active transition metals, particularly copper, in cardiac or vascular tissues in subjects with diabetes that is believed, without wishing to be bound by any particular theory or mechanism, to be accompanied by a suppression of the normal tissue regeneration effected by the migration of stem cells. Elevated tissue levels of copper that suppress the normal biological behaviors of such undifferentiated cells exist irrespective of diabetic status, although the condition may be more prevalent in mammals, including humans, with diabetes.

Conditions occurring in the context of diabetes and/or impaired glucose tolerance in which the suppression of normal stem cell responses can cause impairment of normal tissue responses, and that would be improved with therapy to lower copper values using the doses and dosage forms of treatments described herein, include the following:

1. Heart failure. A significant regeneration of cardiac tissues can occur within a few days of cardiac transplantation. The likely mechanism is migration of stem cells from extra-cardiac sites to the heart, with subsequent differentiation of such cells into various specialized cardiac cells, including myocardial, endothelial and coronary vascular cells. We have determined that copper accumulation in cardiac tissues is likely to severely impair these regenerative responses and that, for example, there is a role for acute intravenous therapy with a copper chelator in the treatment of heart failure, including but not limited to, diabetic heart failure.

2. Acute Myocardial infarction (AMI). AMI is accompanied by proliferation of cells in the ventricular myocardium when, for example, AMI occurs in the context of diabetes. The presence of elevated tissue levels of redox-active transition metals suppresses normal stem cell responses, resulting in impaired structural and functional repair of damaged tissues. The mechanism of the impairment of cardiac function in, for example, diabetes, is believed to be a toxic effect of accumulated transition metals on tissue dynamics, resulting in impaired tissue regeneration caused in turn by suppression of normal stem cell responses, which mediate physiological tissue regeneration by migration to damaged tissue from external sites. Treatment of AMI, for example, in the context of diabetes, will be improved by acute (if necessary, parenteral) as well as by subsequent chronic administration of a copper chelator as described herein.

3. Wound healing and ulceration. The processes of normal tissue repair require intervention of mobilizing stem cells, which effect repair of the various layers of blood vessels, for example. An accumulation of transition metals (particularly copper) in vascular tissues causes the impaired tissue behavior characteristic of diabetes, including impaired wound repair following surgery or trauma, and the exaggerated tendency to ulceration and poor healing of established ulcers. Treatment of diabetics with copper chelators before they undergo surgery, or in the context of traumatic tissue damage, may also be beneficially carried out using the doses and dosage forms of treatments described herein. Surgery in diabetics would have a better outcome if excess transition metals were removed from blood vessels prior to surgery. This may be accomplished on either an acute basis (with parenteral therapy) or on a more chronic basis (with oral therapy) prior to actual surgery or both.

4. Tissue damage resulting from infection. Processes of normal tissue repair following infection require intervention of mobilized stem cells that migrate to sites of tissue damage to effect tissue regeneration and repair of, for example, the various layers of blood vessels. Such tissue damage repair will be impaired by suppressed stem cell responses, such as those caused by the build up of redox-active transition metals (particularly copper) in tissues, for examples the walls of blood vessels. Tissue damage repair, including repair following infection, will be improved, for example, in people with diabetes by use of the doses and dosage forms of treatments described herein.

5. Diabetic kidney damage. Treatment of diabetics and others having kidney failure by administration of a copper chelator according to the doses and dosage forms of treatments described herein will improve organ regeneration by restoring normal tissue healing by allowing stem cells to migrate and differentiate normally.

However, even in the non-diabetic mammal and even in a mammal without a glucose mechanism abnormality, a reduction in extra-cellular copper values is advantageous in that such lower levels will lead to either a reduction in copper mediated tissue damage and/or to improvement in tissue repair by restoration of normal tissue stem cell responses.

In the studies described herein using streptozocin-diabetic (STZ) rat model, a high frequency of tissue damage in both heart and coronary artery tissues in severely diabetic animals has been found, which reflects what is found in man. In one aspect, this invention features a method of diminishment of available free copper values in any at risk subject, whether diabetic or not, and particularly a subject not suffering from Wilson's Disease and who has copper levels capable of diminishment by the administration of an effective amount of an agent capable of lowering copper levels in a subject.

A preferred copper chelator is trientine, including trientine acid addition salts and active metabolites including, for example, N-acetyl trientine, and analogs, derivatives, and prodrugs thereof. Alternative names for trientine include N,N'-Bis(2-aminoethyl)-1,2-ethanedi-amine; triethylenetetramine ("TETA"); 1,8-diamino-3,6-diazaoctane; 3,6-diazaoctane-1,8-diamine; 1,4,7,10-tetraazadecane; trien; TECZA; and, triene. In one embodiment, the trientine is rendered less basic (e.g., as a acid addition salt).

In another embodiment, trientine is modified, i.e., it may be as an analogue or derivative of trientine (or an analogue or derivative of a copper-chelating metabolite of trientine, for example, N-acetyl trientine). Derivatives of trientine or trientine salts or analogues include those modified with polyethylene glycol (PEG). The structure of PEG is $HO+CH_2-CH_2-O-)_n-H$. It is a linear or branched, neutral polyether available in a variety of molecular weights. Analogues of trientine include, for example, compounds in which one or more sulfur molecules is substituted for one or more of the NH groups in trientine. Other analogues include, for example, compounds in which trientine has been modified to include one or more additional —$CH_2$ groups. The chemical formula of trientine is $NH_2-CH_2-CH_2-NH-CH_2-CH_2-NH-CH_2-CH_2-NH_2$. The empirical formula is $C_6N_4H_{18}$. Analogues of trientine include, for example:

1. SH—$CH_2$—$CH_2$—NH—$CH_2$—$CH_2$—NH—$CH_2$—$CH_2$—$NH_2$,
2. SH—$CH_2$—$CH_2$—S—$CH_2$—$CH_2$—NH—$CH_2$—$CH_2$—$NH_2$,
3. NH2-CH2-CH2-NH—CH2-CH2-S—CH2-CH2-SH,
4. $NH_2$—$CH_2$—$CH_2$—S—$CH_2$—$CH_2$—S—$CH_2$—$CH_2$—SH,

5. SH—CH$_2$—CH$_2$—S—CH$_2$—CH$_2$—S—CH$_2$—CH$_2$—SH,
6. NH$_2$—CH$_2$—CH$_2$—NH—CH$_2$—CH$_2$—CH$_2$—NH—CH$_2$—CH$_2$—NH$_2$,
7. SH—CH$_2$—CH$_2$—NH—CH$_2$—CH$_2$—CH$_2$—NH—CH$_2$—CH$_2$—NH$_2$,
8. SH—CH$_2$—CH$_2$—S—CH$_2$—CH$_2$—CH$_2$—NH—CH$_2$—CH$_2$—NH$_2$,
9. NH$_2$—CH$_2$—CH$_2$—NH—CH$_2$—CH$_2$—CH$_2$—S—CH$_2$—CH$_2$—SH,
10. NH$_2$—CH$_2$—CH$_2$—S—CH$_2$—CH$_2$—CH$_2$—S—CH$_2$—CH$_2$—SH,
11. SH—CH$_2$—CH$_2$—S—CH$_2$—CH$_2$—CH$_2$—S—CH$_2$—CH$_2$—SH,
12. and so on.

One or more hydroxyl groups may also be substituted for one or more amine groups to create an analogue of trientine (with or without the substitution of one or more sulfurs for one or more nitrogens). Additional analogues, including acyclic and cyclic analogues, are provided below in reference to Formula I and Formula II.

In another embodiment, trientine is delivered as a prodrug of trientine or a copper chelating metabolite of trientine.

Salts of trientine (which optionally can be salts of a prodrug of trientine or a copper chelating metabolite of trientine) include, in one embodiment, acid addition salts such as, for example, those of suitable mineral or organic acids. Salts of trientine (such as acid addition salts, e.g., trientine dihydrochloride) act as copper-chelating agents that aid in the elimination of copper from the body by forming a stable soluble complex that is readily excreted by the kidney.

In another aspect the present invention consists in a method of (1) improvement or reversal, in whole or in part, of at least one or more of cardiac structure damage in the subject (for example, atrophy, loss of myocytes, expansion of the extracellular space, and/or increased deposition of extracellular matrix (and its consequences), and/or, (2) improvement, in whole or in part, of any one or more of systolic function, diastolic function, contractility, recoil characteristics, and ejection fraction (as determined, for example, by ultrasound, MRI or other imaging), and/or (3) improvement or reversal, in whole or in part, of any damage from disorders of the heart muscle, macrovascular disease, microvascular disease, and/or plaque rupture of athereomatous lesions of major blood vessels (and the consequences thereof), and/or (4) Improvement or reversal, in whole or in part, of damage resulting from diabetic kidney disease, diabetic nephropathy, copper accumulation in the kidney, and/or damage to the renal arteries. This method may comprise:

(i) Diagnosing the mammal as being at risk and at least likely to be subject to some damage capable of being ameliorated and/or reversed, and
(ii) Providing to the mammal, for example, a trientine active agent composition as described herein.

In one embodiment the composition is provided to the subject in a dosage form(s) capable of providing a lower effective dose, and a less pulsile exposure to trientine than has hitherto been the case with "QID" Wilson's disease regimens.

In another aspect the present invention consists in a method of ameliorating or reversing, in whole or in part, in (I) a diabetic human being or other diabetic mammal or (II) a human being or other mammal with copper levels capable of diminishment ("the subject") one or more of atrophy, loss of myocytes, expansion of the extracellular space, and/or increased deposition of extracellular matrix (and its consequences) and/or coronary artery structure damage, including media damage (the muscle layer) and intima damage (the endothelial layer) (and its consequences). The method comprises or includes the step of administration and/or self administration to the subject a slow or sustained release dosage form sufficient to provide effective chelation of copper for an overall diminishment thereof in the subject, said dosage form having as the or an active agent trientine, at least one salt of trientine, at least one trientine prodrug or a salt of such a prodrug, at least one trientine analog or a salt or prodrug of such an analog, and/or at least one active metabolite of trientine or a salt or prodrug of such a metabolite, including but not limited to N-acetyl trientine and salts and prodrugs of N-acetyl trientine ("trientine active agents").

In one embodiment the subject has been identified prior to treatment as being at risk.

In another aspect the present invention consists in a method of ameliorating or reversing, in whole or in part, any one or more of systolic dysfunction, diastolic dysfunction, contractility, lack of desired recoil characteristics and/or desired ejection fraction function (as determined, for example, by ultrasound, MRI or other imaging), disorders of the heart muscle, macrovascular disease, microvascular disease and plaque rupture of athereomatous lesions of major blood vessels (and consequences thereof), in a subject at risk who is either (I) a diabetic subject or (II) a subject with copper levels capable of diminishment, said method comprising the step of administration and/or self administration of a low, slow, and/or controlled release dosage form sufficient to provide effective treatment, for example, by chelation of copper, for an overall diminishment thereof in the subject, said dosage form having one or more copper chelators, for example, one or more trientine active agents.

Diseases, disorders and conditions that are usefully be targeted by the compositions and procedures of the present invention include, but are not limited to, any one or more of the following: diabetic cardiomyopathy, diabetic acute coronary syndrome (e.g.; myocardial infarction (MI), diabetic hypertensive cardiomyopathy, acute coronary syndrome associated with impaired glucose tolerance (IGT), acute coronary syndrome associated with impaired fasting glucose (IFG), hypertensive cardiomyopathy associated with IGT, hypertensive cardiomyopathy associated with IFG, ischemic cardiomyopathy associated with IGT, ischemic cardiomyopathy associated with IFG, ischemic cardiomyopathy associated with coronary heart disease (CHD), acute coronary syndrome not associated with any abnormality of the glucose metabolism, hypertensive cardiomyopathy not associated with any abnormality of the glucose metabolism, ischemic cardiomyopathy not associated with any abnormality of the glucose metabolism (irrespective of whether or not such ischemic cardiomyopathy is associated with coronary heart disease or not), and any one or more disease of the vascular tree including, by way of example, disease states of the aorta, carotid, cerebrovascular, coronary, renal, retinal, vasa nervorum, iliac, femoral, popliteal, arteriolar tree and capillary bed.

In a further aspect the present invention consists in the use of at least one trientine active agent together with other material(s) appropriate for the dosage form, in the manufacture of a sustained release dosage form useful for ameliorating or reversing, in whole or in part, in a subject who is either (I) a diabetic subject or (II) a subject with copper levels capable of diminishment, damage associated with, or irregularity of, any one or more of systolic function, diastolic function, contractility, recoil characteristics and ejection fraction (e.g., as determined clinically, by ultrasound, MRI or other imaging), and/or any one or more of at least some of any damage arising from diabetic kidney disease, diabetic nephropathy and/or copper accumulation in the kidney and/or at least some of any damage to the renal arteries, and/or cardiac structure damage selected from one or more of atrophy, loss of myocytes, expansion of the extracellular space and increased deposition of extracellular matrix (and its consequences), and/or coronary artery structure damage selected from at least media damage (the muscle layer) and intima damage (the endothelial layer) (and its consequences).

The present invention in another aspect provides a method for treating a subject having, for example, any one or more of the indications as defined herein comprising the parenteral administration of a composition having a therapeutically effective amount of a copper chelator wherein said therapeutically effective amount administered is from about 5 mg to about 1100 mg per does and/or per day.

In one embodiment the copper chelator is a trientine active agent. Trientine active agents include, for example, salt(s) of trientine, a trientine prodrug or a salt of such a prodrug, a trientine analogue or a salt or prodrug of such an analog, and/or at least one active metabolite of trientine or a salt or prodrug of such a metabolite, including but not limited to N-acetyl trientine and salts and prodrugs of N-acetyl trientine. Trientine active agents also include the analogues of Formulae I and II.

In one embodiment other therapeutically effective dose ranges of trientine active agents, including but not limited to trientine, trientine salts, trientine analogues of formulae I and II, and so on, for example, include from 10 mg to 1100 mg, 10 mg to 1000 mg, 10 mg to 900 mg, 20 mg to 800 mg, 30 mg to 700 mg, 40 mg to 600 mg, 50 mg to 500 mg, 50 mg to 450 mg, from 50-100 mg to about 400 mg, 50-100 mg to about 300 mg, 110 to 290 mg, 120 to 280 mg, 130 to 270 mg, 140 to 260 mg, 150 to 250 mg, 160 to 240 mg, 170 to 230 mg, 180 to 220 mg, 190 to 210 mg, and/or any other amount within the ranges as set forth.

The composition may include, depending on the rate of parenteral administration, for example, solutions, suspensions, emulsions that can be administered by subcutaneous, intravenous, intramuscular, intradermal, intrasternal injection or infusion techniques.

The formulation can further include, for example, any one or more of the following a buffer, for example, an acetate, phosphate, citrate or glutamate buffer to obtain a pH of the final formulation from approximately 5.0 to 9.5, a carbohydrate or polyhydric alcohol tonicifier, an antimicrobial preservative that may be selected from the group of, for example, m-cresol, benzyl alcohol, methyl, ethyl, propyl and butyl parabens and phenol and a stabilizer.

A sufficient amount of water for injection is used to obtain the desired concentration of solution. Sodium chloride, as well as other excipients, may also be present, if desired. Such excipients, however, must maintain the overall stability of the trientine active form.

The formulation of the invention should be substantially isotonic. An isotonic solution may be defined as a solution that has a concentration of electrolytes, non-electrolytes, or a combination of the two that will exert an equivalent osmotic pressure as that into which it is being introduced, in this case, mammalian tissue. By "substantially isotonic" is meant within ±20% of isotonicity, preferably within ±10%. The formulated product may be included within a container, typically, for example, a vial, cartridge, prefilled syringe or disposable pen.

In another aspect the present invention provides a parenteral composition comprising a therapeutically effective amount of a copper chelator to be administered to a subject having any one or more of the indications as defined herein.

The indications include, for example, diabetic cardiomyopathy, diabetic acute coronary syndrome (e.g.; myocardial infarction—MI), diabetic hypertensive cardiomyopathy, acute coronary syndrome associated with impaired glucose tolerance (IGT), acute coronary syndrome associated with impaired fasting glucose (IFG), hypertensive cardiomyopathy associated with IGT, hypertensive cardiomyopathy associated with IFG, ischemic cardiomyopathy associated with IGT, ischemic cardiomyopathy associated with IFG, ischemic cardiomyopathy associated with coronary heart disease (CHD), disorders of the heart muscle (cardiomyopathy or myocarditis) that include, for example, idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy, acute coronary syndrome not associated with any abnormality of glucose metabolism, hypertensive cardiomyopathy not associated with any abnormality of glucose metabolism, ischemic cardiomyopathy not associated with any abnormality of glucose metabolism (irrespective of whether or not such ischemic cardiomyopathy is associated with coronary heart disease or not), and any one or more diseases of the vascular tree including, by way of example, disease states of the aorta, carotid, and of the arteries including cerebrovascular, coronary, renal, retinal, iliac, femoral, popliteal, vasa nervorum, arteriolar tree and capillary bed, atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries, cardiac structure damage which includes, but is not limited to, for example, atrophy, loss of myocytes, expansion of the extracellular space and increased deposition of extracellular matrix (and its consequences) and/or coronary artery structure damage selected from at least media (the muscle layer) and/or intima (the endothelial layer) damage (and its consequences), plaque rupture of atheromatous lesions of major blood vessels such as the aorta, the coronary arteries, the carotid arteries, the cerebrovascular arteries, the renal arteries, the iliac arteries, the femoral arteries and the popliteal arteries, systolic dysfunction, diastolic dysfunction, aberrant contractility, recoil characteristics and ejection fraction, toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems.

In one embodiment the copper chelator is a trientine active agent. Trientine active agents include, for example, salt(s) of trientine, a trientine prodrug or a salt of such a prodrug, a trientine analog or a salt or prodrug of such an analog, and/or at least one active metabolite of trientine or a salt or prodrug of such a metabolite, including but not limited to N-acetyl trientine and salts and prodrugs of N-acetyl trientine.

A therapeutically effective amount of a copper chelator, for example, one or more trientine active agents, including but not limited to trientine, trientine salts, trientine analogues of formulae I and II, and so on, is from about 5 mg to 1200 mg per day. Other therapeutically effective dose ranges, for example, include from 10 mg to 1100 mg, 10 mg to 1000 mg, 10 mg to 900 mg, 20 mg to 800 mg, 30 mg to 700 mg, 40 mg to 600 mg, 50 mg to 500 mg, 50 mg to 450 mg, from 50-100 mg to about 400 mg, 50-100 mg to about 300 mg, 110 to 290 mg, 120 to 280 mg, 130 to 270 mg, 140 to 260 mg, 150 to 250 mg, 160 to 240 mg, 170 to 230 mg, 180 to 220 mg, 190 to 210 mg, and/or any other amount within the ranges as set forth.

The composition may include, depending on the rate of parenteral administration, for example, solutions, suspensions, emulsions that can be administered by subcutaneous, intravenous, intramuscular, intradermal, intrasternal injection or infusion techniques.

The formulation can further include, for example, any one or more of the following a buffer, for example, an acetate, phosphate, citrate or glutamate buffer to obtain a pH of the final formulation from approximately 5.0 to 9.5, a carbohydrate or polyhydric alcohol tonicifier, an antimicrobial preservative that may be selected from the group of, for example, m-cresol, benzyl alcohol, methyl, ethyl, propyl and butyl parabens and phenol and a stabilizer.

A sufficient amount of water for injection is used to obtain the desired concentration of solution. Sodium chloride, as well as other excipients, may also be present, if desired. Such excipients, however, must maintain the overall stability of the trientine active form.

The formulation of the invention should be substantially isotonic. An isotonic solution may be defined as a solution that has a concentration of electrolytes, non-electrolytes, or a combination of the two that will exert an equivalent osmotic pressure as that into which it is being introduced, in this case, mammalian tissue. By "substantially isotonic" is meant within ±20% of isotonicity, preferably within ±10%. The formulated product may be included within a container, typically, for example, a vial, cartridge, prefilled syringe or disposable pen.

In a further aspect the present invention provides the use of a therapeutically effective amount of a copper chelator in the manufacture of a medicament for the treatment of a subject having any one or more of the following indications: diabetic cardiomyopathy, diabetic acute coronary syndrome (e.g.; myocardial infarction—MI), diabetic hypertensive cardiomyopathy, acute coronary syndrome associated with impaired glucose tolerance (IGT), acute coronary syndrome associated with impaired fasting glucose (IFG), hypertensive cardiomyopathy associated with IGT, hypertensive cardiomyopathy associated with IFG, ischemic cardiomyopathy associated with IGT, ischemic cardiomyopathy associated with IFG, ischemic cardiomyopathy associated with coronary heart disease (CHD), disorders of the heart muscle (cardiomyopathy or myocarditis) that include, for example, idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy, acute coronary syndrome not associated with any abnormality of glucose metabolism, hypertensive cardiomyopathy not associated with any abnormality of glucose metabolism, ischemic cardiomyopathy not associated with any abnormality of glucose metabolism (irrespective of whether or not such ischemic cardiomyopathy is associated with coronary heart disease or not), and any one or more diseases of the vascular tree including, by way of example, disease states of the aorta, carotid, and of the arteries including cerebrovascular, coronary, renal, retinal, iliac, femoral, popliteal, vasa nervorum, arteriolar tree and capillary bed, atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries, cardiac structure damage which includes, but is not limited to, for example, atrophy, loss of myocytes, expansion of the extracellular space and increased deposition of extracellular matrix (and its consequences) and/or coronary artery structure damage selected from at least media (the muscle layer) and/or intima (the endothelial layer) damage (and its consequences), plaque rupture of atheromatous lesions of major blood vessels such as the aorta, the coronary arteries, the carotid arteries, the cerebrovascular arteries, the renal arteries, the iliac arteries, the femoral arteries and the popliteal arteries, systolic dysfunction, diastolic dysfunction, aberrant contractility, recoil characteristics and ejection fraction, toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems.

In one embodiment, the copper chelator is a trientine active agent. Trientine active agents include, for example, salt(s) of trientine, a trientine prodrug or a salt of such a prodrug, a trientine analog or a salt or prodrug of such an analog, and/or at least one active metabolite of trientine or a salt or prodrug of such a metabolite, including but not limited to N-acetyl trientine and salts and prodrugs of N-acetyl trientine.

The therapeutically effective amount of a copper chelator, for example, a trientine active agents, including but not limited to trientine, trientine salts, trientine analogues of formulae I and II, and so on, is from about 5 mg to 1200 mg per day. Other therapeutically effective dose ranges, for example, include from 10 mg to 1100 mg, 10 mg to 1000 mg, 10 mg to 900 mg, 20 mg to 800 mg, 30 mg to 700 mg, 40 mg to 600 mg, 50 mg to 500 mg, 50 mg to 450 mg, from 50-100 mg to about 400 mg, 50-100 mg to about 300 mg, 110 to 290 mg, 120 to 280 mg, 130 to 270 mg, 140 to 260 mg, 150 to 250 mg, 160 to 240 mg, 170 to 230 mg, 180 to 220 mg, 190 to 210 mg, and/or any other amount within the ranges as set forth.

The composition may include, depending on the rate of parenteral administration, for example, solutions, suspensions, emulsions that can be administered by subcutaneous, intravenous, intramuscular, intradermal, intrasternal injection or infusion techniques.

The formulation can further include, for example, any one or more of the following a buffer, for example, an acetate, phosphate, citrate or glutamate buffer to obtain a pH of the final formulation from approximately 5.0 to 9.5, a carbohydrate or polyhydric alcohol tonicifier, an antimicrobial preservative that may be selected from the group of, for example, in-cresol, benzyl alcohol, methyl, ethyl, propyl and butyl parabens and phenol and a stabilizer.

A sufficient amount of water for injection is used to obtain the desired concentration of solution. Sodium chloride, as well as other excipients, may also be present, if desired. Such excipients, however, must maintain the overall stability of the trientine active form.

The formulation of the invention should be substantially isotonic. An isotonic solution may be defined as a solution that has a concentration of electrolytes, non-electrolytes, or a combination of the two that will exert an equivalent osmotic pressure as that into which it is being introduced, in this case, mammalian tissue. By "substantially isotonic" is meant within ±20% of isotonicity, preferably within ±10%. The formulated product may be included within a container, typically, for example, a vial, cartridge, prefilled syringe or disposable pen.

As used herein, parenteral administration, includes, but is not limited, to any one or more of the following administration routes; subcutaneous, intravenous, intramuscular, intraperitoneal, intrasternal, intraarticular or intrasternal injection or infusion techniques (e.g., as sterile injectable aqueous or non-aqueous solutions or suspensions); nasally such as by inhalation spray; topically, such as in the form of a cream or ointment; or vaginally.

Therapy may be monitored with a 24-hour urinary copper analysis periodically. Urine must be collected in copper-free glassware. It is expected that the patient probably will be in the desired state of negative copper balance if 0.5 to 1.0 milligram of copper is present in a 24-hour collection of urine.

The present invention in one aspect provides a method for treating a subject having, for example, any one or more of the indications as defined herein comprising the parenteral administration of a composition having a therapeutically effective amount of a copper chelator wherein said therapeutically effective amount administered parenterally per dose rate is in the range of about 0.1 mg/kg to about 40 mg/kg based on the body weight of the subject.

In another embodiment the therapeutically effective amount of copper chelator, for example, one or more trientine active agents, including but not limited to trientine, trientine salts, trientine analogues of formulae I and II, and so on, is from about 5 mg to 1200 mg per day. Other therapeutically effective dose ranges, for example, include from 10 mg to 1100 mg, 10 mg to 1000 mg, 10 mg to 900 mg, 20 mg to 800 mg, 30 mg to 700 mg, 40 mg to 600 mg, 50 mg to 500 mg, 50 mg to 450 mg, from 50-100 mg to about 400 mg, 50-100 mg to about 300 mg, 110 to 290 mg, 120 to 280 mg, 130 to 270 mg, 140 to 260 mg, 150 to 250 mg, 160 to 240 mg, 170 to 230 mg, 180 to 220 mg, 190 to 210 mg, and/or any other amount within the ranges as set forth.

The composition may include, depending on the rate of parenteral administration, for example, solutions, suspensions, emulsions that can be administered by subcutaneous, intravenous, intramuscular, intradermal, intrasternal injection or infusion techniques.

The formulation can further include, for example, any one or more of the following a buffer, for example, an acetate, phosphate, citrate or glutamate buffer to obtain a pH of the final formulation from approximately 5.0 to 9.5, a carbohydrate or polyhydric alcohol tonicifier, an antimicrobial preservative that may be selected from the group of, for example, m-cresol, benzyl alcohol, methyl, ethyl, propyl and butyl parabens and phenol and a stabilizer.

A sufficient amount of water for injection is used to obtain the desired concentration of solution. Sodium chloride, as well as other excipients, may also be present, if desired. Such excipients, however, must maintain the overall stability of the trientine active form.

The formulation of the invention should be substantially isotonic. An isotonic solution may be defined as a solution that has a concentration of electrolytes, non-electrolytes, or a combination of the two that will exert an equivalent osmotic pressure as that into which it is being introduced, in this case, mammalian tissue. By "substantially isotonic" is meant within ±20% of isotonicity, preferably within ±10%. The formulated product may be included within a container, typically, for example, a vial, cartridge, prefilled syringe or disposable pen.

In a further aspect the present invention consists in a transdermal patch, pad, wrap or bandage ("patch") capable of being adhered or otherwise associated with the skin of a subject, said patch being capable of delivering an effective amount of one or more trientine active agents when so applied to a subject who is either (I) a diabetic subject or (II) a subject with copper levels capable of diminishment to ameliorate or reverse, in whole or in part, any one or more of systolic dysfunction, diastolic dysfunction, contractility dysfunction, recoil dysfunction and ejection fraction dysfunction (as determined, for example, by ultrasound, MRI or other imaging) and/or any one or more of at least some of any damage arising from diabetic kidney disease, diabetic nephropathy and/or copper accumulation in the kidney and/or at least some of any damage to the renal arteries and/or cardiac structure damage selected from one or more of atrophy, loss of myocytes, expansion of the extracellular space and increased deposition of extracellular matrix (and its consequences), and/or coronary artery structure damage selected from at least media damage (the muscle layer) and intima damage (the endothelial layer) (and its consequences).

In another aspect the present invention consists in an article of manufacturing comprising a vessel containing as a CR, SR and/or ER dosage form or one or more active agents, or containing in CR, SR and/or ER dosage forms one or more pharmaceutically copper chelators, including but not limited to one or more acceptable trientine active agents; and instructions for use for ameliorating and/or reversing, in whole or in part, in subject who is either (I) a diabetic subject or (II) a subject with copper levels capable of diminishment any one or more of the above-listed indications.

In another aspect the present invention consists in an article of manufacture comprising packaging material; and contained within the packaging material one or more pharmaceutically acceptable trientine active agents in a CR, SR and/or ER dosage form, wherein the packaging material has a label that indicates that the dosage form can be used for ameliorating, reversing and/or improving in a subject who is either (I) a diabetic subject or (II) a subject with copper levels capable of diminishment, any one or more of the above-listed indications.

In one embodiment the dosage form, effective amount and/or dosage regimen as herein referred to is able to provide an effective daily dosage to the subject of a trientine active agent (when expressed, for example, as the dihydrochloride salt of trientine, irrespective of whether or not the dosage unit includes that salt) of 4 g per day or below although if given orally the dosage is from 1 mg to 4 g per day.

In another embodiment the oral dose delivery (cumulative or otherwise) is in the range of from 200 mg to 4 g per day if given orally. In a further embodiment the daily dosage is such as to deliver 1.2 g per day or below.

In another aspect the dosage delivery is to provide, for example, when expressed as trientine dihydrochloride or other compound herein, a delivery into the subject (irrespective of the dosage included in the dosage unit or units) being, administered of from 1 mg to 1.2 g per day. If orally administered the dosage is from 200 mg to 1.2 g per day.

In a further embodiment the dosage is such as to deliver, for example, the trientine active agent in a dosage unit that administers the trientine active agent at a pH of from 7.2 to 7.6 (preferably a pH of 7.4±0.1).

In another embodiment the dosage of, for example, the trientine active agent, for example, trientine dihydrochloride in sustained release is such that there is always less of the active ingredient in a subject's body than results from the 250 mg plus oral dosage forms for Wilson's disease.

In another embodiment a sustained release dosage form or forms of, for example, the trientine active agent, for example, trientine dihydrochloride is provided that are suitable for once daily administration and that provide sustained or controlled and long-lasting in vivo release. The form may deliver, for example, not more than 10% trientine dihydrochloride in about 5 hours at an acid pH of about <4.5 and delivers greater than 50% of trientine dihydrochloride in 12 hrs at a pH of about <6.5 in a controlled manner during in vivo and in vitro dissolution.

In yet a further aspect the present invention provides a method of administering an effective amount of, for example, one or more trientine active agents formulated in a delayed release preparation (DR), a slow release preparation (SR), an extended release preparation (ER), a controlled release preparation (CR) and/or in a repeat action preparation (RA). In one embodiment the formulations of DR, SR, ER, RA, or CR are suitable for use in the treatment of any of the indications listed herein, including but not limited to, heart failure, diabetic heart disease, acute coronary syndrome, hypertensive heart disease, ischemic heart disease, coronary artery disease, peripheral arterial disease, Wilson's disease, or any form of cancer. Formulations of DR, SR, ER, RA, or CR may contain an effective dosage unit for delivery to the subject of from about 1 mg to abut 600 mg per unit of at least one trientine active agent, although in a further embodiment the total daily dose rate is from between 5 grams to 1 mg and may work to maintain a desired blood plasma concentration of the trientine active agent for a desired period of time, preferably at least about from between 18 to 24 hours.

In another aspect the present invention consists in a formulation of, for example, at least one trientine active agent that maintains constant plasma concentrations of the trientine active agent for extended periods and is effective in removing copper from the body of subjects with any one or more of the indications listed herein, including but not limited to, heart failure, diabetic heart disease, acute coronary syndrome, hypertensive heart disease, ischemic heart disease, coronary artery disease, peripheral arterial disease, Wilson's disease, or any form of cancer.

In another aspect of the present invention consists in a device containing, for example, one or more trientine active agents in a monolithic matrix device and employed for the treatment of any one or more of the indications listed herein, including but not limited to, heart failure, diabetic heart disease, acute coronary syndrome, hypertensive heart disease, ischemic heart disease, coronary artery disease, peripheral arterial disease, Wilson's disease, or any form of cancer.

In one embodiment the monolithic matrix device contains said one or more trientine active agents in a dispersed soluble matrix, in which said one or more trientine active agents becomes increasingly available as the matrix dissolves or swells. The monolithic matrix device, may include but is not limited to one or more of the following excipients: hydroxypropylcellulose (BP) or hydroxypropyl cellulose (USP); hydroxypropyl methylcellulose (BP, USP); methylcellulose (BP, USP); calcium carboxymethylcellulose (BP, USP); acrylic acid polymer or carboxy polymethylene (Carbopol) or Carbomer (BP, USP); or linear glycuronan polymers such as alginic acid (BP, USP), for example those formulated into microparticles from alginic acid (alginate)-gelatin hydrocolloid coacervate systems, or those in which liposomes have been encapsulated by coatings of alginic acid with poly-L-lysine membranes. Alternatively, said monolithic matrix includes one or more trientine active agents dissolved in an insoluble matrix, from which said one or more trientine active agents becomes available as an aqueous solvent enters the matrix through micro-channels and dissolves the trientine particles.

In a further embodiment the monolithic matrix contains, for example, said one or more trientine active agents particles in a lipid matrix or insoluble polymer matrix, including but not limited to preparations formed from Carnauba wax (BP; USP); medium-chain triglyceride such as fractionated coconut oil (BP) or triglycerida saturata media (PhEur); or cellulose ethyl ether or ethylcellulose (BP, USP). The lipids can be present in said monolithic matrix from between 20-40% hydrophobic solids w/w. The lipids may remain intact during the release process.

In another embodiment the device contains in addition to, for example, said one or more trientine active agents, one or more of the following, for example: a channeling agent, such as sodium chloride or one or more sugars, which leaches from the formulation, forming aqueous micro-channels (capillaries) through which solvent enters, and through which drug is released.

Alternatively the device is any hydrophilic polymer matrix, in which said one or more, for example, trientine active agents is/are compressed as a mixture with any water-swellable hydrophilic polymer.

The trientine active agent(s), for example, contained in the hydrophilic polymer matrix may be between 20-80% (w/w).

In one embodiment the hydrophilic polymer matrix contains in addition to said one or more, for example, trientine active agents any one or more of the following, for example: a gel modifier such as one or more of a sugar, counter ions, a pH buffer, a surfactant, a lubricant such as a magnesium stearate and/or a glidant such as colloidal silicon dioxide.

In another aspect the present invention consists in any device containing an effective amount of, for example, said one or more tritentine active agents comprising or including a rate-controlling membrane surrounding a drug reservoir and containing lactulose mixed with microcrystalline cellulose. The ratio of lactulose to microcrystalline cellulose may be, for example, about 60:40.

Clinical trials referred to hereinafter revealed that a divided dose of 1.2 g/day of trientine is effective for and yet (insofar as an instantaneous body level is concerned) in excess of dosage levels to be required chronically in practice for the purpose of amelioration and/or reversal of cardiac structure damage and/or coronary artery structure damage. Such a dose rate of 1.2 g per day is capable of being provided by the use of capsules of 300 mg trientine hydrochloride given half an hour before meals two being given in the morning and two being given at night.

A measurement of free copper [which equals total plasma copper minus ceruloplasmin-bound copper] can be made using the procedure disclosed in the Merck & Co Inc datasheet (www.Merck.com) for SYPRINE® (trientine dihydrochloride) capsules: It states, "The most reliable index for monitoring treatment is the determination of free cooper in the serum, which equals the difference between quantitatively determined total copper and ceruloplasmin-copper. Adequately treated subjects will usually have less than 10 mcg free copper/dL of serum. Therapy may be monitored with a 24-hour urinary copper analysis periodically. Urine must be collected in copper-free glassware. Since a low copper diet should keep copper absorption down to less than one milligram a day, the subject probably will be in the desired state of negative copper balance if 0.5 to 1.0 milligram of copper is present in a 24-hour collection of urine".

BRIEF DESCRIPTION OF THE DRAWINGS

We have conducted studies reliant on trientine dihydrochloride in the STZ rat model as well in humans and wish to describe the invention further by reference to the accompanying drawings in which:

FIG. 3 shows copper excretion in the urine of diabetic and non-diabetic animals receiving increasing doses of trientine or an equivalent volume of saline, wherein copper excretion in urine of diabetic (top) and nondiabetic (bottom) rats receiving increasing doses of trientine (0.1, 1.0, 10, 100 mg·kg$^{-1}$ in 75 μl saline followed by 125 μl saline flush injected at time shown by arrow) or an equivalent volume of saline, and each point represents a 15 min urine collection period (see Example 2 Methods for details); error bars show SEM and P values are stated if significant (P<0.05).

FIG. 12 is a table comparing the copper and iron excretion in the animals receiving trientine or saline, which is a statistical analysis using a mixed linear model.

DETAILED DESCRIPTION OF THE INVENTION

Figure 1:
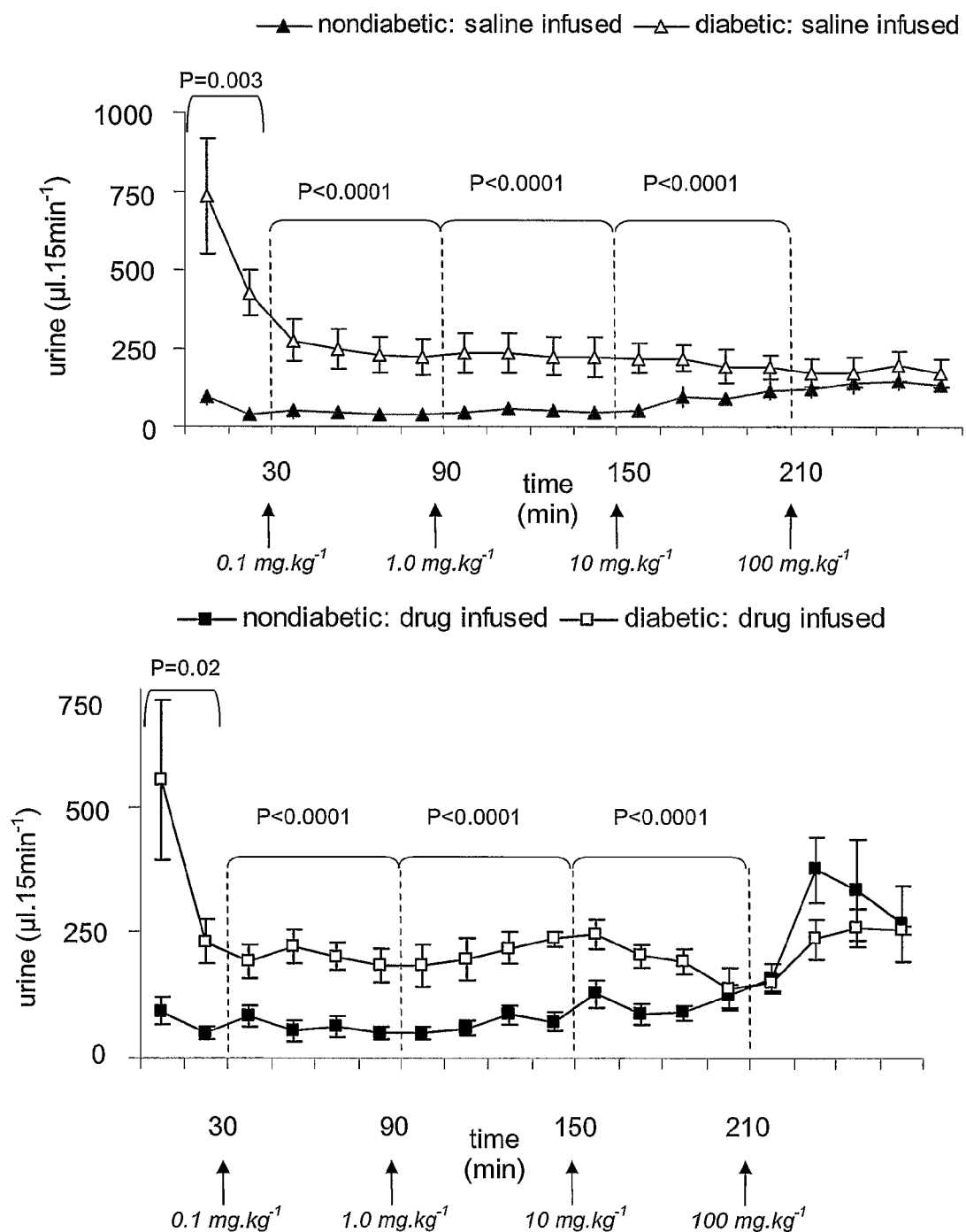
FIG. 1 shows the urine excretion in diabetic and non-diabetic animals in response to increasing doses of trientine or equivalent volume of saline, wherein urine excretion in diabetic and nondiabetic animals in response to increasing doses of trientine (bottom; 0.1, 1.0, 10, 100 mg·kg$^{-1}$ in 75 μl saline followed by 125 μl saline flush injected at time shown by arrow) or an equivalent volume of saline (top), and each point represents a 15 min urine collection period (see Example 2 Methods for details); error bars show SEM and P values are stated if significant (P<0.05).
Figure 2:
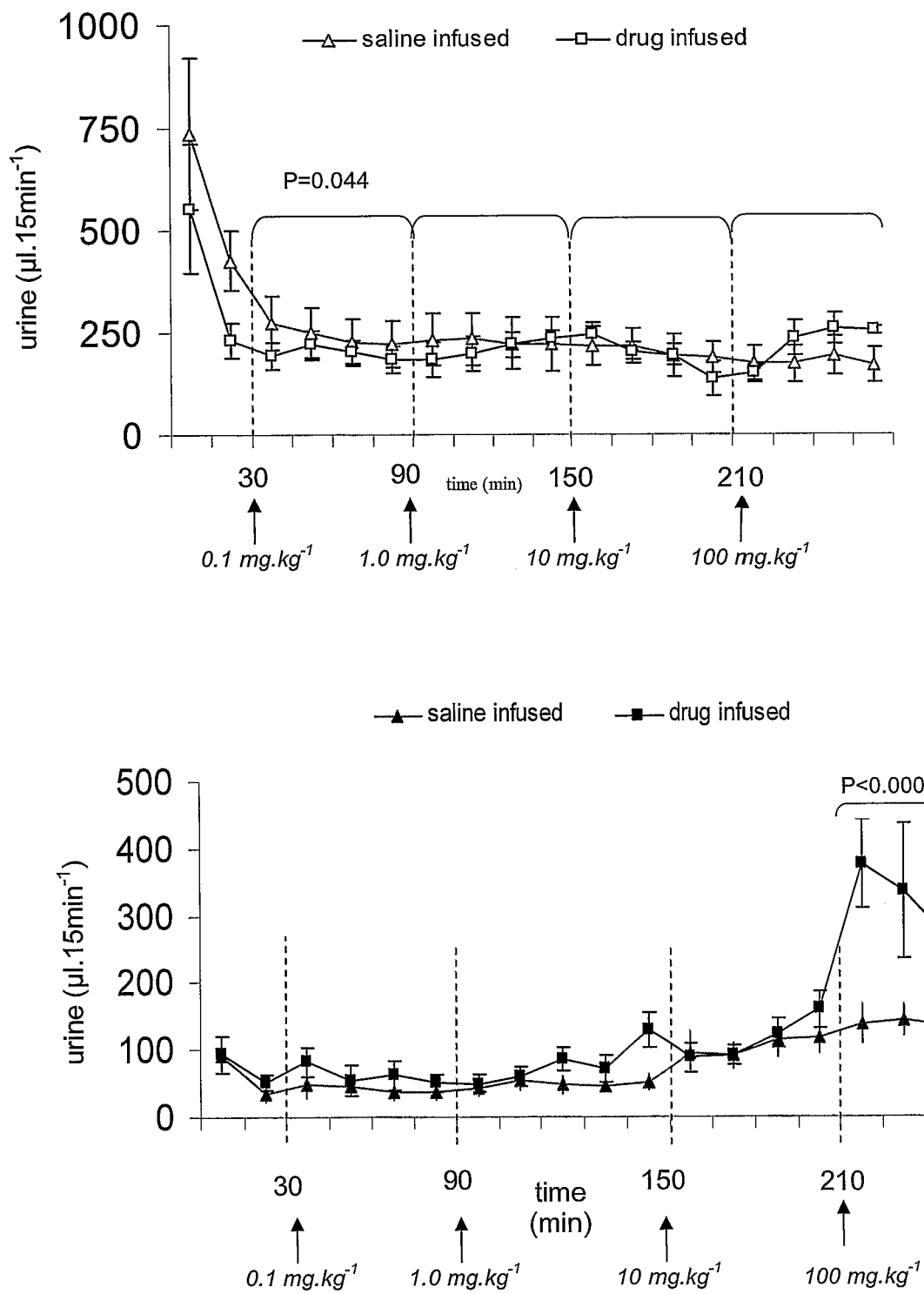
FIG. 2 shows urine excretion in non-diabetic and diabetic animals receiving increasing doses of trientine or an equivalent volume of saline, wherein urine excretion in diabetic (top) and nondiabetic (bottom) rats receiving increasing doses of trientine (0.1, 1.0, 10, 100 mg·kg$^{-1}$ in 75 μl saline followed by 125 μl saline flush injected at time shown by arrow) or an equivalent volume of saline, and each point represents a 15 min urine collection period (see Example 2 Methods for details); error bars show SEM and P values are stated if significant (P<0.05).

We have now shown in the STZ rat model for both diabetic and non-diabetic humans a diminishment in available free copper has an affect in ameliorating or reversing, in whole or in part, for example, cardiac structure damage. This includes damage resulting from, for example, atrophy, loss of myocytes, expansion of the extra cellular space and increased deposition of extra cellular matrix (and its consequences), and coronary artery structure injury (and its consequences). In demonstrating reversal of damage in the STZ rat, as further described herein, dose relativity for man has been discovered insofar as copper scavenging into the urine is concerned. Additionally, under physiological conditions injury to the cardiac structure is sensed by distant stem cells, which migrate to the site of damage then undergo alternate stem cell differentiation, i.e., these events promote structural and functional repair. However, it has been determined that the accumulation of redox-active transition metals, particularly copper in cardiac tissues and coronary arteries in subjects with diabetes, is accompanied by a suppression of the normal tissue regeneration effected by the migration of stem cells. In other words, elevated tissue levels of copper suppress these normal biological behaviors of such undifferentiated cells. Even in the non-diabetic mammal (e.g., without type 2 diabetes mellitus) and even in a mammal without a glucose mechanism abnormality (e.g., without IGT or without IFG), a reduction in extra-cellular copper values will be advantageous in providing a reduction in and/or a reversal of copper-associated damage, for example, in whole or in part, as well as improved tissue repair by restoration of normal tissue stem cell responses.

A proof of principle Phase 2 study has shown positive results. However, the dosage regimen was sub-optimal when compared with its pharmacokinetic profile and the recently discovered site-of-action profile. The bioavailability of the active species of, for example, trientine dihydrochloride after oral administration is low (<10%) due to poor absorption and marked first-pass metabolism. Trientine dihydrochloride and its transformed metabolite, N-acetyl-trientine hydrochloride, are both capable of binding copper, although the chelating activity of the analogue N-acetyl-trientine hydrochloride is reportedly significantly lower than trientine dihydrochloride. See, Kodama H., et al., *Life Sciences* 61:899-907 (1997). Additionally, food, mineral supplements and other drugs adversely affect absorption of trientine dihydrochloride. The half-life of various copper chelators, for example, trientine, indicated for the treatment and reversal of heart failure and coronary heart disease, is relatively short—being approximately 2 hours. Ideally trientine should be taken in addition to current therapies, at a maximum tolerated dose, utilizing a dose regimen that fits its pharmacokinetic and site of action profiles. Regarding the plasma concentration of trientine after oral administration to a patient, see Miyazaki, K., et al., "Determination of trientine in plasma of subjects with high-performance liquid chromatography," *Chem Pharm Bull* 38:1035-38 (1998). Subjects with heart failure and/or coronary artery disease are frequently on multiple drug regimens. Improved copper chelator doses, dose preparation, and/or routes of administration for said doses and dose preparations is needed for this reason as well.

The invention is related to and provides novel doses and dose formulations, and routes of administration of various doses and dose formulations, of copper chelators such as, for example, trientine active agents. Trientine active agents include, for example, trientine, salts of trientine, prodrugs of trientine and salts of such prodrugs, analogs of trientine and salts and prodrugs of such analogs, and/or active metabolites of trientine and salts and prodrugs of such metabolites, including but not limited to N-acetyl trientine and salts and prodrugs of N-acetyl trientine. It is believed, without wishing to be bound by any particular mechanism or theory of operation or effectiveness, that the dose and dose formulations, and routes of administration, provide unexpected benefits in the amelioration and reversal, in whole or in part, of disorders, diseases, and conditions as set forth or referenced or suggested herein, and in which copper is believed to play a role.

Wilson's disease is due to an inherited defect in copper excretion into the bile by the liver. The resulting copper accumulation and copper toxicity results in liver disease, and in some patients, brain damage. Patients present, generally between the ages of 10 and 40 years, with liver disease, neurological disease of a movement disorder type, or behavioral abnormalities, and often with a combination of these. Wilson's disease is effectively treated with orally administered copper chelators. It has been demonstrated that chelated copper in patients with Wilson's disease is excreted primarily through the feces, either by the effective chelation of copper in the gut (or inhibition of absorption), or by partial restoration of mechanisms that allow for excretion of excess copper via urine or into the bile, or a combination of the two. See Siegemund R, et al., "Mode of action of triethylenetetramine dihydrochloride on copper metabolism in Wilson's disease," *Acta Neurol Scand.* 83(6):364-6 (June 1991).

In contrast, experiments described herein unexpectedly revealed that administration of the copper chelator trientine dihydrochloride, for example, to non-Wilson's disease patients does not result in increased excretion of copper in the feces. See Example 9 and Table 11. Rather, excretion of excess copper in non-Wilson's disease patients treated with copper chelators occurs primarily, if not virtually exclusively, through the urine rather than the feces. See Example 8 and FIG. 12. These data support the idea that systemic (parenteral) administration of doses of copper chelators that are lower than those given orally, or controlled release administration of doses of copper chelators that are lower than those given orally, or oral administration of lower dose forms that avoid undesired first pass clearance such that more active ingredient is available for its intended purpose outside the gut, will be of significant benefit in the indications described herein, for example. This includes administration of doses and dose forms that provide for metered release directly into the circulatory system (including intramuscular, intraperitoneal, subcutaneous and intravenous administration) rather than indirectly through the gut. Thus, the compounds may also be formulated for parenteral injection (including, for example, by bolus injection or continuous infusion) and may be presented in unit dose form in ampules, pre-filled syringes, small bolus infusion containers, or in multi-does containers with an added preservative.

According to the invention, doses and dose formulations of copper chelators, including for example, trientine, that maintain desired blood and tissue levels may be prepared that are highly effective in causing removal of systemic copper from the body via the urine and at lower doses than required for oral administration given that gut copper need not be excreted, and will be more effective in the treatment of any condition in which pathologically increased or undesired tissue copper plays a role in disease initiation or progression. Such diseases include any of the indications identified herein, including but not limited to the following: heart failure, diabetic heart disease, acute coronary syndrome, hypertensive heart disease, ischemic heart disease, coronary artery disease, peripheral arterial disease, and forms of cancer amenable to treatment by copper chelation.

Trientine is a strongly basic moiety with multiple nitrogens that can be converted into a large number of suitable associated acid addition salts using an acid, for example, by reaction of stoichiometrically equivalent amounts of trientine and of the acid in an inert solvent such as ethanol or water and subsequent evaporation if the dosage form is best formulated from a dry salt. Possible acids for this reaction are in particular those that yield physiologically acceptable salts. Nitrogen-containing copper chelators, for example, trientine active agents such as, for example, trientine, that can be delivered as a salt(s) (such as acid addition salts, e.g., trientine dihydrochloride) act as copper-chelating agents, which aids the elimination of copper from the body by forming a stable soluble complex that is readily excreted by the kidney. Thus inorganic acids can be used, e.g., sulfuric acid, nitric acid, hydrohalic acids such as hydrochloric acid or hydrobromic acid, phosphoric acids such as orthophosphoric acid, sulfamic acid. This is not an exhaustive list. Other organic acids can be used to prepare suitable salt forms, in particular aliphatic, alicyclic, araliphatic, aromatic or heterocyclic mono- or polybasic carboxylic, sulfonic or sulfuric acids, (e.g., formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono-and-disulfonic acids, and laurylsulfuric acid). Those in the art will be able to prepare other suitable salt forms. Nitrogen-containing copper chelators, for example, trientine active agents such as, for example, trientine, can also be in the form of quaternary ammonium salts in which the nitrogen atom carries a suitable organic group such as an alkyl, alkenyl, alkynyl or aralkyl moiety. In one embodiment such nitrogen-containing copper chelators are in the form of a compound or buffered in solution and/or suspension to a near neutral pH much lower than the pH 14 of a solution of trientine itself.

Other trientine active agents include derivative trientine active agents, for example, trientine in combination with picolinic acid (2-pyridinecarboxylic acid). These derivatives include, for example, trientine picolinate and salts of trientine picolinate, for example, trientine picolinate HCl. These also include, for example, trientine di-picolinate and salts of trientine di-picolinate, for example, trientine di-picolinate HCl. Picolinic acid moieties may be attached to trientine, for example one or more of the $CH_2$ moieties, using chemical techniques known in the art. Those in the art will be able to prepare other suitable derivatives, for example, trientine-PEG derivatives, which may be useful for particular dosage forms including oral dosage forms having increased bioavailability.

Other trientine active agents include trientine analogue active agents. Such analogues include cyclic and acyclic analogues according to the following formulae, for example:

FORMULA I

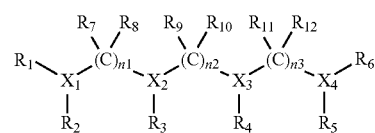

Acyclic analogs of trientine are provided as follows based on the above Formula I for tetra-heteroatom acyclic analogues, where X1, X2, X3, and X4 are independently chosen from the atoms N, S or O such that, (a) for a four-nitrogen series, i.e., when X1, X2, X3, and X4 are N then: R1, R2, R3, R4, R5, and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and, R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R3, R4, R5, or R6 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(b) for a first three-nitrogen series, i.e., when X1, X2, X3, are N and X4 is S or O then: R6 does not exist; R1, R2, R3, R4, R5, and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and, R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R3, R4, or R5 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(c) for a second three-nitrogen series, i.e., when X1, X2, and X4 are N and X3 is O or S then: R4 does not exist and R1, R2, R3, R5, and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and, R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R3, R5, or R6 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(d) for a first two-nitrogen series, i.e., when X2, and X3 are N and X1 and X4 are O or S then: R1 and R6 do not exist; R2, R3, R4, and R5 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R2, R3, R4, or R5 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(e) for a second two-nitrogen series, i.e., when X1, and X3 are N and X2 and X4 are 0 or S then: R3 and R6 do not exist; R1, R2, R4, and R5 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R4, or R5 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(f) for a third three-nitrogen series, i.e., when X1, and X2 are N and X3 and X4 are O or S then: R4 and R6 do not exist; R1, R2, R3, and R5 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R3, or R5 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(g) for a fourth three-nitrogen series, i.e., when X1, and X4 are N and X2 and X3 are O or S then: R3 and R4 do not exist; R1, R2, R5 and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R5, or R6 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

Second, for a tetra-heteroatom cyclic series of analogues, R1 and R6 are joined together by a bridging group in the form of $(CR13R14)n4$, and X1, X2, X3, and X4 are independently chosen from the atoms N, S or O such that, (a) for a four-nitrogen series, i.e., when X1, X2, X3, and X4 are N then: R2, R3, R4, and R5 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, n3, and n4 are independently chosen to be 2 or 3; and R7, R8, R9, R10, R11, R12, R13 and R14 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R2, R3, R4, or R5 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, C1-C10 alkyl-S-protein. Furthermore one or several of R7, R8, R9, R10, R11, R12, R13 or R14 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(b) for a three-nitrogen series, i.e., when X1, X2, X3, are N and X4 is S or O then: R5 does nor exist; R2, R3, and R4 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, n3, and n4 are independently chosen to be 2 or 3; and R7, R8, R9, R10, R11, R12, R13 and R14 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R2, R3 or R4 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, R12, R13 or R14 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(c) for a first two-nitrogen series, i.e., when X2, and X3 are N and X1 and X4 are O or S then: R2 and R5 do not exist; R3 and R4 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, n3, and n4 are independently chosen to be 2 or 3; and R7, R8, R9, R10, R11, R12, R13 and R14 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or both of R3, or R4 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, R12, R13 or R14 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(d) for a second two-nitrogen series, i.e., when X1, and X3 are N and X2 and X4 are 0 or S then: R3 and R5 do not exist; R2 and R4 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, n3, and n4 are independently chosen to be 2 or 3; and R7, R8, R9, R10, R11, R12, R13 and R14 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or both of R2, or R4 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, R12, R13 or R14 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(e) for a one-nitrogen series, i.e., when X1 is N and X2, X3 and X4 are O or S then: R3, R4 and R5 do not exist; R2 is independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, n3, and n4 are independently chosen to be 2 or 3; and R7, R8, R9, R10, R11, R12, R13 and R14 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, R2 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, R12, R13 or R14 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

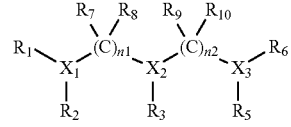

FORMULA II

Tri-heteroatom acyclic analogues according to the above Formula II are provided where X1, X2, and X3 are independently chosen from the atoms N, S or O such that, (a) for a three-nitrogen series, when X1, X2, and X3 are N then: R1, R2, R3, R5, and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, and n2 are independently chosen to be 2 or 3; and R7, R8, R9, and R10 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R3, R5 or R6 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, or R10 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(b) for a first two-nitrogen series, when X1, and X3, are N and X2 is S or O then: R3 does not exist; R1, R2, R3, R5, and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, and n2 are independently chosen to be 2 or 3; and R7, R8, R9, and R10 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R5 or R6 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, or R10 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(c) for a second, two-nitrogen series, when X1 and X2 are N and X3 is O or S then: R3 does not exist; R1, R2, R5, and R6 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1 and n2 are independently chosen to be 2 or 3; and R7, R8, R9, and R10 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R1, R2, R5, or R6 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, or R10 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

A second series of tri-heteroatom acyclic analogues according to the above Formula II are provided in which R1 and R6 are joined together by a bridging group in the form of $(CR11R12)n3$, and X1, X2, and X3 are independently chosen from the atoms N, S or O such that:

(a) for a three-nitrogen series, when X1, X2, and X3 are N then: R2, R3, and R5 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or several of R2, R3, or R5 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl- S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(b) for a two-nitrogen series, when X1, X2, are N and X3 is S or O then: R5 does not exist; R2, and R3 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, one or both of R2 or R3 may be functionalized in order to be attached to peptides, proteins, polyethylene glycols and other such chemical entities in order to modify the overall pharmacokinetics, deliverability and/or half-lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

(c) for a one-nitrogen series, when X1 is N and X2, and X3 are O or S then: R3, and R5 do not exist; R2 is independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl, $CH_2COOH$, $CH_2SO_3H$, $CH_2PO(OH)_2$, $CH_2P(CH_3)O(OH)$; n1, n2, and n3 are independently chosen to be 2 or 3; and R7, R8, R9, R10, R11, and R12 are independently chosen from H, CH3, C2-C10 straight chain or branched alkyl, C3-C10 cycloalkyl, C1-C6 alkyl C3-C10 cycloalkyl, aryl, mono, di, tri, tetra and penta substituted aryl, heteroaryl, fused aryl, C1-C6 alkyl aryl, C1-C6 alkyl mono, di, tri, tetra and penta substituted aryl, C1-C5 alkyl heteroaryl, C1-C6 alkyl fused aryl. In addition, R2 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein. Furthermore one or several of R7, R8, R9, R10, R11, or R12 may be functionalized in order to be attached to peptides, proteins, polyethylene glycols and other such chemical entities in order to modify the overall pharmacokinetics, deliverability and/or half lives of the constructs. Examples of such functionalization include but are not limited to C1-C10 alkyl-CO-peptide, C1-C10 alkyl-CO-protein, C1-C10 alkyl-CO-PEG, C1-C10 alkyl-NH-peptide, C1-C10 alkyl-NH-protein, C1-C10 alkyl-NH—CO-PEG, C1-C10 alkyl-S-peptide, and C1-C10 alkyl-S-protein.

The analogues of the invention may be made using any of a variety of chemical synthesis, isolation, and purification methods known in the art.

Aspects of the invention include controlled or other drug dose and drug dose delivery formulations and devices containing one or more copper chelators, for example, trientine or salts thereof. The present invention includes, for example, doses and dosage forms for at least oral administration, transdermal delivery, topical application, suppository delivery, transmucosal delivery, injection (including subcutaneous administration, subdermal administration, intramuscular administration, depot administration, and intravenous administration (including delivery via bolus, slow intravenous injection, and intravenous drip), infusion devices (including implantable infusion devices, both active and passive), administration by inhalation or insufflation, buccal administration, sublingual administration, and ophthalmic administration.

Indications in which the doses, dose formulations, and routes of administration thereof will be useful include, for example, diabetic cardiomyopathy, diabetic acute coronary syndrome (e.g.; myocardial infarction—MI), diabetic hypertensive cardiomyopathy, acute coronary syndrome associated with impaired glucose tolerance (IGT), acute coronary syndrome associated with impaired fasting glucose (IFG), hypertensive cardiomyopathy associated with IGT, hypertensive cardiomyopathy associated with IFG, ischemic cardiomyopathy associated with IGT, ischemic cardiomyopathy associated with IFG, ischemic cardiomyopathy associated with coronary heart disease (CHD), disorders of the heart muscle (cardiomyopathy or myocarditis) that include, for example, idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy, acute coronary syndrome not associated with any abnormality of glucose metabolism, hypertensive cardiomyopathy not associated with any abnormality of glucose metabolism, ischemic cardiomyopathy not associated with any abnormality of glucose metabolism (irrespective of whether or not such ischemic cardiomyopathy is associated with coronary heart disease or not), and any one or more diseases of the vascular tree including, by way of example, disease states of the aorta, carotid, and of the arteries including cerebrovascular, coronary, renal, retinal, iliac, femoral, popliteal, vasa nervorum, arteriolar tree and capillary bed, atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries, cardiac structure damage which includes, but is not limited to, for example, atrophy, loss of myocytes, expansion of the extracellular space and increased deposition of extracellular matrix (and its consequences) and/or coronary artery structure damage selected from at least media (the muscle layer) and/or intima (the endothelial layer) damage (and its consequences), plaque rupture of atheromatous lesions of major blood vessels such as the aorta, the coronary arteries, the carotid arteries, the cerebrovascular arteries, the renal arteries, the iliac arteries, the femoral arteries and the popliteal arteries, systolic dysfunction, diastolic dysfunction, aberrant contractility, recoil characteristics and ejection fraction, toxic, drug-induced, and metabolic (including hypertensive and/or diabetic disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems. Thus, the present invention also is directed to novel doses and dose formulations of one or more copper chelators, for example, trientine or salts thereof, useful for the pharmacological therapy of diseases in humans and other mammals as disclosed herein. The use of these doses, formulations and devices of, for example, trientine enables effective treatment of these conditions, through novel and improved formulations of the drug suitable for administration to humans and other mammals.

The invention provides, for example, drug delivery formulations containing one or more copper chelators, for example, trientine or salts thereof. Thus, the present invention is directed in part to novel delivery formulations of one or more copper chelators, for example, trientine to optimize bioavailability and to maintain plasma concentrations within the therapeutic range, including for extended periods, and results in increases in the time that trientine plasma concentrations of one or more copper chelators, for example, trientine or salts thereof, remain within a desired therapeutic range at the site or sites of action. Controlled delivery preparations also optimize the drug concentration at the site of action and minimize periods of under and over medication, for example.

The invention also in part provides drug delivery formulations and devices containing one or more copper chelators, for example, one or more trientine active agents, including but not limited to, trientine, trientine dihydrochloride or other pharmaceutically acceptable salts thereof, the formulation being suitable for periodic administration, including once daily administration, to provide low dose controlled and/or low dose long-lasting in vivo release of a copper chelator for chelation of copper and excretion of chelated copper via the urine.

The invention also in part provides a drug delivery formulations and devices containing one or more copper chelators, for example, one or more trientine active agents, including but not limited to, trientine, trientine dihydrochloride or other pharmaceutically acceptable salts thereof, the formulation being suitable for periodic administration, including once daily administration, to provide enhanced bioavailability of a copper chelator for chelation of copper and excretion of chelated copper via the urine.

Examples of controlled drug formulations useful for delivery of the compounds and formulations of the invention are found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C., Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The USP also provides examples of modified-release oral dosage forms, including those formulated as tablets or capsules. See, for example, The United States Pharmacopeia 23/National Formulary 18, The United States Pharmacopeial Convention, Inc., Rockville Md., 1995 (hereinafter "the USP"), which also describes specific tests to determine the drug release capabilities of extended-release and delayed-release tablets and capsules. The USP test for drug release for extended-release and delayed-release articles is based on drug dissolution from the dosage unit against elapsed test time. Descriptions of various test apparatus and procedures may be found in the USP. The individual monographs contain specific criteria for compliance with the test and the apparatus and test procedures to be used. Examples have been given, for example for the release of aspirin from Aspirin Extended-release Tablets (for example, see: Ansel, H. C., Allen, L. V. and Popovich, N. G. Pharmaceutical Dosage Forms and Drug Delivery Systems, 7th Ed., Lippincott 1999, p. 237). Modified-release tablets and capsules must meet the USP standard for uniformity as described for conventional dosage units. Uniformity of dosage units may be demonstrated by either of two methods, weight variation or content uniformity, as described in the USP. Further guidance concerning the analysis of extended release dosage forms has been provided by the F.D.A. (see Guidance for Industry. Extended release oral dosage forms: development, evaluation, and application of in vitro/in vivo correlations. Rockville, Md.: Center for Drug Evaluation and Research, Food and Drug Administration, 1997). Compliance of a dosage regime is always essential in order to derive the best benefit from a treatment regime. The present invention recognizes an additional benefit from dosage forms that can provide such levels of delivery to a subject as are required to elicit the advantages now seen from the prospect of lower overall dose delivery of trientine formulations when one compares them to BID (two times a day), TID (three times a day), QID (four times a day), and so on, multiple dosage oral regimes hitherto used with, for example, trientine formulations for Wilson's disease.

Aspects of the invention also include various drug delivery systems for the delivery of one or more copper chelators, for example, trientine or salts thereof. Thus, the present invention also is directed to novel types of drug delivery systems. These include, for example, modified-release (MR) dosage forms of the present invention, including delayed-release (DR) forms; prolonged-action (PA) forms; controlled-release (CR) forms; extended-release (ER) forms; timed-release (TR) forms; and long-acting (LA) forms. For the most part, these terms are used to describe orally administered dosage forms, whereas the term rate-controlled delivery is applied to certain types of drug delivery systems in which the rate of drug delivery is controlled by features of the device rather than by physiological or environmental conditions such as gastrointestinal pH or drug transit time through the gastrointestinal tract. These formulations effect (1) delayed total drug release form some time after drug administration, (2) drug release in small aliquots intermittently after administration, (3) drug release slowly at a controlled rate governed by the delivery system, (4) drug release at a constant rate that does not vary, and/or (5) drug release for a significantly longer period than usual formulations. Within the scope of the terms "modified", "delayed", "slow", "prolonged", "timed", "long-acting", "controlled", and/or "extended" release dosage units as used herein are any appropriate delivery form.

Advantages of these formulations for administration of one or more copper chelators, for example, trientine or salts thereof, include convenience to the subject; increased compliance and achievement of steady state drug levels with twice-daily (or less) dosing; smoothening of plasma drug profiles to a constant level for extended time periods; prevention of drug toxicity; and elimination of breakthrough of therapeutic failure, especially at night. Modified-release dosage forms of the invention include dosage forms having drug release features based on time, course, and/or location which are designed to accomplish therapeutic or convenience objectives not offered by conventional or immediate-release forms. See, for example, Bogner, R. H. Bioavailability and bioequivalence of extended-release oral dosage forms. *U. S. Pharmacist* 22 (Suppl.):3-12 (1997); Scale-up of oral extended-release drug delivery systems: part I, an overview. *Pharmaceutical Manufacturing* 2:23-27 (1985). Extended-release dosage forms of the invention include, for example, as defined by The United States Food and Drug Administration (F. D. A.), a dosage form that one that allows a reduction in dosing frequency to that presented by a conventional dosage form, e.g., a solution or an immediate-release dosage form. See, for example, Bogner, R. H. Bioavailability and bioequivalence of extended-release oral dosage forms. *US Pharmacist* 22 (Suppl.):3-12 (1997); Guidance for industry. Extended release oral dosage forms: development, evaluation, and application of the in vitro/in vivo correlations. Rockville, Md.: Center for Drug Evaluation and Research, Food and Drug Administration (1997). Repeat action dosage forms of the invention include, for example, forms that contain two single doses of medication, one for immediate release and the second for delayed release. Bi-layered tablets, for example, may be prepared with one layer of drug for immediate release with the second layer deigned to release drug later as either a second dose or in an extended-release manner. Targeted-release dosage forms of the invention include, for example, formulations that facilitate drug release and which are directed towards isolating or concentrating a drug in a body region, tissue, or site for absorption or for drug action.

One example is oral delivery forms of tablet, capsule, lozenge, or the like form, or any liquid form such as syrups, aqueous solutions, emulsion and the like, capable of providing over the period of time between dosages an ongoing release of an effective level of the active ingredient, e.g., one or more the compounds and formulations of the invention.

Examples of dosage units for transdermal delivery of the compounds and formulations of the invention include transdermal patches, transdermal bandages, and the like.

Examples of dosage units for topical delivery of the compounds and formulations of the invention are any lotion, stick, spray, ointment, paste, cream, gel, etc. whether applied directly to the skin or via an intermediary such as a pad, patch or the like but which again has a slow release action in delivery of the active agent into the body of the subject.

Examples of dosage units for suppository delivery of the compounds and formulations of the invention include any solid dosage form inserted into a bodily orifice particularly those inserted rectally, vaginally and urethrally.

Examples of dosage units for transmucosal delivery of the compounds and formulations of the invention include depositories solutions for enemas, pessaries, tampons, creams, gels, pastes, foams, nebulised solutions, powders and similar formulations containing in addition to the active ingredients such carriers as are known in the art to be appropriate.

Examples of dosage units for injection of the compounds and formulations of the invention include delivery via bolus such as single or multiple administrations by intravenous injection, subcutaneous, subdermal, and intramuscular administration or oral administration.

Examples of dosage units for depot administration of the compounds and formulations of the invention include pellets or small cylinders of active agent or solid forms wherein the active agent is entrapped in a matrix of biodegradable polymers, microemulsions, liposomes or is microencapsulated.

Examples of infusion devices for compounds and formulations of the invention include infusion pumps containing one or more copper chelators, for example, for example, trientine or salts thereof, at a desired amount for a desired number of doses or steady state administration, and include implantable drug pumps. Examples of implantable infusion devices include any solid form in which the active agent is encapsulated within or dispersed throughout a biodegradable polymer or synthetic, polymer such as silicone, silicone rubber, silastic or similar polymer.

Examples of dosage units for inhalation or insufflation of the compounds and formulations of the invention include compositions comprising solutions and/or suspensions in pharmaceutically acceptable, aqueous, or organic solvents, or mixture thereof and/or powders.

Examples of dosage units for buccal delivery of the compounds and formulations of the invention include lozenges, tablets and the like, compositions comprising solutions and/or suspensions in pharmaceutically acceptable, aqueous, or organic solvents, or mixture thereof and/or powders Examples of dosage units for sublingual delivery of the compounds and formulations of the invention include lozenges, tablets and the like, compositions comprising solutions and/or suspensions in pharmaceutically acceptable, aqueous, or organic solvents, or mixture thereof and/or powders Examples of dosage units for ophthalmic delivery of the compounds and formulations of the invention include compositions comprising solutions and/or suspensions in pharmaceutically acceptable, aqueous, or organic solvents, inserts, The invention in part provides dose delivery devices and formulations incorporating one or more copper chelators, for example, trientine or salts thereof, complexed with one or more suitable anions to yield complexes that are only slowly soluble in body fluids. One such example of modified release forms of one or more copper chelators, for example, trientine or salts thereof, is produced by the incorporation of the active agent or agents into certain complexes such as those formed with the anions of various forms of tannic acid (for example, see: Merck Index 12th Ed., 9221). Dissolution of such complexes may depend, for example, on the pH of the environment. This slow dissolution rate provides for the extended release of the drug. For example, trientine salts of tannic acid, trientine tannates, provide for this quality, and are expected to possess utility for the treatment of conditions in which increased copper plays a role. Examples of equivalent products are provided by those having the tradename Rynatan (Wallace: see, for example, Madan, P. L., "Sustained release dosage forms," *U.S. Pharmacist* 15:39-50 (1990); Ryna-12 S, which contains a mixture of mepyramine tannate with phenylephrine tannate, Martindale 33rd Ed., 2080.4).

Also included in the invention are coated beads, granules or microspheres containing one or more copper chelators, for example, trientine or salts thereof. Thus, the invention also provides a method to achieve modified release of one or more copper chelators, for example, trientine or salts thereof, by incorporation of the drug into coated beads, granules, or microspheres. Such formulations of one or more copper chelators, for example trientine or salts thereof, have utility for the treatment of diseases in humans and other mammals in which a copper chelator, for example, trientine, is indicated. In such systems, the drug is distributed onto beads, pellets, granules or other particulate systems. Using conventional pan-coating or air-suspension coating techniques, a solution of the drug substance is placed onto small inert nonpareil seeds or beads made of sugar and starch or onto microcrystalline cellulose spheres. The nonpareil seeds are most often in the 425 to 850 micrometer range whereas the microcrystalline cellulose spheres are available ranging from 170 to 600 micrometers (see Ansel, H. C., Allen, L. V. and Popovich, N. G. Pharmaceutical Dosage Forms and Drug Delivery Systems, 7th Ed., Lippincott 1999, p. 232). The microcrystalline spheres are considered more durable during production than sugar-based cores (see: Celphere microcrystalline cellulose spheres. Philadelphia: FMC Corporation, 1996). Methods for manufacture of microspheres suitable for drug delivery have been described (see, for example, Arshady, R. Microspheres and microcapsules: a survey of manufacturing techniques. 1: suspension and cross-linking. *Polymer Eng Sci* 30:1746-1758 (1989); see also, Arshady, R. Micro-spheres and microcapsules: a survey of manufacturing techniques. 2: coacervation. *Polymer Eng Sci* 30:905-914 (1990); see also: Arshady R. Microspheres and micro-capsules: a survey of manufacturing techniques. 3: solvent evaporation. *Polymer Eng Sci* 30:915-924 (!990). In instances in which the drug dose is large, the starting granules of material may be composed of the drug itself. Some of these granules may remain uncoated to provide immediate drug release. Other granules (about two-thirds to three-quarters) receive varying coats of a lipid material such as beeswax, carnauba wax, glycerylmonostearate, cetyl alcohol, or a cellulose material such as ethylcellulose (infra). Subsequently, granules of different coating thickness are blended to achieve a mixture having the desired drug-release characteristics. The coating material may be coloured with one or more dyes to distinguish granules or beads of different coating thickness (by depth of colour) and to provide distinctiveness to the product. When properly blended, the granules may be placed in capsules or tableted. Various coating systems are commercially available which are aqueous-based and which use ethylcellulose and plasticizer as the coating material (e.g., Aquacoat™ [FMC Corporation, Philadelphia] and Surerelease™ [Colorcon]; Aquacoat aqueous polymeric dispersion. Philadelphia: FMC Corporation, 1991; Surerelease aqueous controlled release coating system. West Point, Pa.: Colorcon, 1990; Butler, J., Cumming, I, Brown, J. et al. A novel multiunit controlled-release system. Pharm Tech 22:122-138 (1998); Yazici, E., Oner, L., Kas, H. S. & Hincal, A. A. Phenytoin sodium microspheres: bench scale formulation, process characterization and release kinetics. *Pharmaceut Dev Technol* 1:175-183 (1996)). Aqueous-based coating systems eliminate the hazards and environmental concerns associated with organic solvent-based systems. Aqueous and organic solvent-based coating methods have been compared (see, for example, Hogan, J. E. Aqueous versus organic solvent coating. *Int J Pharm Tech Prod Manufacture* 3:17-20 (1982)). The variation in the thickness of the coats and in the type of coating materials used affects the rate at which the body fluids are capable of penetrating the coating to dissolve the drug. Generally, the thicker the coat, the more resistant to penetration and the more delayed will be drug release and dissolution. Typically, the coated beads are about 1 mm in diameter. They are usually combined to have three or four release groups among the more than 100 beads contained in the dosing unit (see Madan, P. L. Sustained release dosage forms. U. S. Pharmacist 15:39-50 (1990)). This provides the different desired sustained or extended release rates and the targeting of the coated beads to the desired segments of the gastrointestinal tract. One example of this type of dosage form is the Spansule™ (SmithKline Beecham Corporation, U. K.). Examples of film-forming polymers which can be used in water-insoluble release-slowing intermediate layer(s) (to be applied to a pellet, spheroid or tablet core) include ethylcellulose, polyvinyl acetate, Eudragit® RS, Eudragit® RL, etc. (Each of Eudragit® RS and Eudragit® RL is an ammonio methacrylate copolymer.) The release rate can be controlled not only by incorporating therein suitable water-soluble pore formers, such as lactose, mannitol, sorbitol, etc., but also by the thickness of the coating layer applied. Multi tablets include small spheroid-shaped compressed minitablets that may have a diameter of between 3 to 4 mm and can be placed in gelatin capsule shell to provide the desired pattern of drug release. Each capsule may contain 8-10 minitablets, some uncoated for immediate release and others coated for extended drug release.

The following methods may be employed to generate delivery systems containing modified-release delivery forms of one or more copper chelators, for example trientine or salts thereof or other trientine active agents, suitable for oral administration to humans and other mammals. Two basic mechanisms are available to achieve modified release drug delivery. These are altered dissolution or diffusion of drugs and excipients. Within this context, for example, four processes may be employed, either simultaneously or consecutively. These are as follows: (i) hydration of the device (e.g., swelling of the matrix); (ii) diffusion of water into the device; (iii) controlled or delayed dissolution of the drug; and (iv) controlled or delayed diffusion of dissolved or solubilized drug out of the device. Continuous release is ideally zero-order, and is produced by a constant rate of diffusion or osmosis. Modified release dosage forms commonly fit into one of three categories of system: monolithic or matrix; reservoir- or membrane-controlled; or osmotic pump systems. Each comprises the following components: active drug; release controlling agents; matrix modifiers; drug modifiers; supplementary coatings; and conventional formulation excipients, such as those described in reference works known to those skilled in the art (see, for example, Kibble A. H (ed.) Handbook of Pharmaceutical Excipients, 3rd Edition, American Pharmaceutical Association, 2000, 665 pp.).

For orally administered dosage forms of the compounds and formulations of the invention, extended drug action may be achieved by affecting the rate at which the drug is released from the dosage form and/or by slowing the transit time of the dosage form through the gastrointestinal tract (see Bogner, R. H. Bioavailability and bioequivalence of extended-release oral dosage forms. *US Pharmacist* 22 (Suppl.):3-12 (1997)). The rate of drug release from solid dosage forms may be modified by the technologies described below which, in general, are based on the following: 1) modifying drug dissolution by controlling access of biologic fluids to the drug through the use of barrier coatings; 2) controlling drug diffusion rates from dosage forms; and 3) chemically reacting or interacting between the drug substance or its pharmaceutical barrier and site-specific biological fluids. Systems by which these objectives are achieved are also provided herein. In one approach, employing digestion as the release mechanism, the active agent is either coated or entrapped in a substance that is slow digested or dispersed into the intestinal tract. The rate of availability of the active agent is a function of the rate of digestion of the dispersible material. Therefore, the release rate, and thus the effectiveness of the agent, varies from subject to subject depending upon the ability of the subject to digest the material. In another approach such as disclosed in U.S. Pat. No. 3,247,066, the active agent is dispersed in a water-soluble colloid and then coated with a rupturable plastic, non-digestible material that is permeable to the diffusion of water. After ingestion and upon entering the gastrointestinal tract, water in the body fluids diffuses through the coating and causes the colloid to swell. The coating is ruptured by the swelling colloid and the total content of active agent is released. Although there is substantially less variation in the rate of release from subject to subject, substantially the entire active agent is released at once resulting in an initially high blood level content that decreases rapidly with time.

U.S. Pat. No. 3,115,441 discloses another encapsulation method useful for delivery of the compounds and formulations of the invention wherein particles of active agent are first given a quick thin coating of a film-forming material and a non-toxic, hydrophobic material that is then coated with successive coatings of an organic solvent-resistant material. The coated particles are mixed with uncoated active agent and this mixture is then formed into a tablet with the coated tablets being entrapped in a matrix of the uncoated active agent. Tablets made according to this method have the advantage of providing immediate delivery of the compounds and formulations of the invention because the matrix material (which comprises the initial dosage) dissolves immediately upon ingestion.

Another approach, as in U.S. Pat. No. 4,025,613, is to provide an improved blood level profile of the compounds and formulations of the invention that results from simply applying a film of a non-aqueous solution of cellulose acetate over either individual particles of active agent before tableting or over the outside of tablets formed from untreated active agent particles, which upon drying forms a coating of cellulose acetate. Depending on the role attributed to the film-coating, persons skilled in the art will be able to choose the film-forming agent from among the following categories: cellulose derivatives such as hydroxypropylmethylcellulose (HPMC), ethyl cellulose, cellulose acetophthalate, cellulose acetopropionate, cellulose trimelliate, the polymers and copolymers of methacrylic acid and its derivatives. The film-forming agent may be supplemented with: plasticizers (such as polyoxyethylene glycols of high molecular weight, esters of polyacids such as citric acid or phthalic acid) fillers (such as talc, metal oxides such as titanium oxide) colorants chosen from those usable and approved by the pharmaceutical and food industries.

A further form of slow release form of the compounds and formulations of the invention is any suitable osmotic system where semipermeable membranes of cellulose acetate, cellulose acetate butyrate, cellulose acetate propionate, to control the release of active ingredients. These can be coated with aqueous dispersions of enteric lacquers without changing release rate. An example of such an osmotic system is an osmotic pump device, an example of which is the Oros™ device developed by Alza Inc. (U.S.A.). This system comprises a core tablet surrounded by a semi-permeable membrane coating having a 0.4 mm diameter hole produced by a laser beam. The core tablet has two layers, one containing the drug (the "active" layer) and the other containing a polymeric osmotic agent (the "push" layer). The core layer consists of active drug, filler, a viscosity modulator, and a solubilizer. The system operates on the principle of osmotic pressure. This system is suitable for delivery of a wide range of drugs, including trientine or salts thereof. The coating technology is straightforward, and release is zero-order. When the tablet is swallowed, the semi-permeable membrane permits aqueous fluid to enter from the stomach into the core tablet, dissolving or suspending the drug. As pressure increases in the osmotic layer, it forces or pumps the drug solution out of the delivery orifice on the side of the tablet. Only the drug solution (not the undissolved drug) is capable of passing through the hole in the tablet. The system is designed such that only a few drops of water are drawn into the tablet each hour. The rate of inflow of aqueous fluid and the function of the tablet depends on the existence of an osmotic gradient between the contents of the bi-layer and the fluid in the gastrointestinal tract. Drug delivery is essentially constant as long as the osmotic gradient remains unchanged. The drug release rate may be altered by changing the surface area, the thickness or composition of the membrane, and/or by changing the diameter of the drug release orifice. The drug-release rate is not affected by gastrointestinal acidity, alkalinity, fed conditions, or gut motility. The biologically inert components of the tablet remain intact during gut transit and are eliminated in the feces as an insoluble shell. Other examples of the application of this technology are provided by Glucotrol XL Extended Release Tablets (Pfizer Inc.) and Procardia XL Extended Release Tablets (Pfizer Inc.; see, Martindale 33rd Ed., p. 2051.3).

The invention also provides delivery devices for compounds and formulations of the invention that utilize monolithic matrices including, for example, slowly eroding or hydrophilic polymer matrices, in which one or more copper chelators, for example, trientine or salts thereof, is compressed or embedded.

Monolithic matrix devices for delivery of the compounds and formulations of the invention comprise those formed using either of the following systems, for example: (I), drug particles are dispersed in a soluble matrix, in which they become increasingly available as the matrix dissolves or swells; examples include hydrophilic colloid matrices, such as hydroxypropylcellulose (BP) or hydroxypropyl cellulose (USP); hydroxypropyl methylcellulose (HPMC; BP, USP); methylcellulose (MC; BP, USP); calcium carboxymethylcellulose (Calcium CMC; BP, USP); acrylic acid polymer or carboxy polymethylene (Carbopol) or Carbomer (BP, USP); or linear glycuronan polymers such as alginic acid (BP, USP), for example those formulated into microparticles from alginic acid (alginate)-gelatin hydrocolloid coacervate systems, or those in which liposomes have been encapsulated by coatings of alginic acid with poly-L-lysine membranes. Drug release occurs as the polymer swells, forming a matrix layer that controls the diffusion of aqueous fluid into the core and thus the rate of diffusion of drug from the system. In such systems, the rate of drug release depends upon the tortuous nature of the channels within the gel, and the viscosity of the entrapped fluid, such that different release kinetics can be achieved, for example, zero-order, or first-order combined with pulsatile release. Where such gels are not cross-linked, there is a weaker, non-permanent association between the polymer chains, which relies on secondary bonding. With such devices, high loading of the active drug is achievable, and effective blending is frequent. Devices contain 20-80% of drug (w/w), along with gel modifiers that can enhance drug diffusion; examples of such modifiers include sugars that can enhance the rate of hydration, ions that can influence the content of cross-links, and pH buffers that affect the level of polymer ionization. Hydrophilic matrix devices typically contain pH buffers, surfactants, counter-ions, lubricants such as magnesium stearate (BP, USP) and a glidant such as colloidal silicon dioxide (USP; colloidal anhydrous silica, BP) in addition to drug substance and hydrophilic matrix; (II) drug particles are dissolved in an insoluble matrix, from which drug becomes available as solvent enters the matrix, often through channels, and dissolves the drug particles. Examples include systems formed with a lipid matrix, or insoluble polymer matrix, including preparations formed from Carnauba wax (BP; USP); medium-chain triglyceride such as fractionated coconut oil (BP) or triglycerida saturata media (PhEur); or cellulose ethyl ether or ethylcellulose (BP, USP). Lipid matrices are simple and easy to manufacture, and incorporate the following blend of powdered components: lipids (20-40% hydrophobic solids w/w) which remain intact during the release process; drug substance; channeling agent, such as sodium chloride or sugars, which leaches from the formulation, forming aqueous micro-channels (capillaries) through which solvent enters, and through which drug is released. In the alternative system, which employs an insoluble polymer matrix, the drug is embedded in an inert insoluble polymer and is released by leaching of aqueous fluid, which diffuses into the core of the device through capillaries formed between particles, and from which drug diffuses out of the device. The rate of release is controlled by the degree of compression, particle size, and the nature and relative content (w/w) of excipients. An example of such a device is that of Ferrous Gradumet (Martindale 33rd Ed., 1360.3). A further example of a suitable insoluble matrix is an inert plastic matrix. By this method, trientine active agent is granulated with an inert plastic material such as polyethylene, polyvinyl acetate, or polymethacrylate, and the granulated mixture is then compressed into tablets. Once ingested, the drug is slowly released from the inert plastic matrix by diffusion (see, for example, Bodmeier, R. & Paeratakul, O., "Drug release from laminated polymeric films prepared from aqueous latexes," *J Pharm Sci* 79:32-26 (1990); Laghoueg, N., et al., "Oral polymer-drug devices with a core and an erodable shell for constant drug delivery," *Int J Pharm* 50:133-139 (1989); Buckton, G., et al., "The influence of surfactants on drug release from acrylic matrices. *Int J Pharm* 74:153-158 (1991)). The compression of the tablet creates the matrix or plastic form that retains its shape during the leaching of the drug and through its passage through the gastrointestinal tract. An immediate-release portion of drug may be compressed onto the surface of the tablet. The inert tablet matrix, expended of drug, is excreted with the feces. An example of a successful dosage form of this type is Gradumet (Abbott; see, for example, Ferro-Gradumet, Martindale 33rd Ed., p. 1860.4).

Further useful approaches have compounds and formulations of the invention incorporated in pendent attachments to a polymer matrix (see, for example, Scholsky, K. M. & Fitch, R. M. Controlled release of pendant bioactive materials from acrylic polymer colloids. J Controlled Release 3:87-108 (1986)). In these devices, drugs are attached by means of an ester linkage to poly(acrylate) ester latex particles prepared by aqueous emulsion polymerization.

Further embodiments incorporate dosage forms of the compounds and formulations of the invention in which the drug is bound to a biocompatible polymer by a labile chemical bond, e.g., polyanhydrides prepared from a substituted anhydride (itself prepared by reacting an acid chloride with the drug: methacryloyl chloride and the sodium salt of methoxy benzoic acid) have been used to form a matrix with a second polymer (Eudragit RL) which releases drug on hydrolysis in gastric fluid (see: Chafi, N., Montheard, J. P. & Vergnaud, J. M. Release of 2-aminothiazole from polymeric carriers. Int J Pharm 67:265-274 (1992)).

In formulating a successful hydrophilic matrix system for the compounds and formulations of the invention, the polymer selected for use must form a gelatinous layer rapidly enough to protect the inner core of the tablet from disintegrating too rapidly after ingestion. As the proportion of polymer is increased in a formulation so is the viscosity of the gel formed with a resulting decrease in the rate of drug diffusion and release (see Formulating for controlled release with Methocel Premium cellulose ethers. Midland, Mich.: Dow Chemical Company, 1995). In general, 20% (w/w) of HPMC results in satisfactory rates of drug release for an extended-release tablet formulation. However, as with all formulations, consideration must be given to the possible effects of other formulation ingredients such as fillers, tablet binders, and disintegrants. An example of a proprietary product formulated using a hydrophilic matrix base of HPMC for extended drug release is that of Oramorph SR Tablets (Roxane; see Martindale 33rd Ed., p. 2014.4).

Two-layered tablets can be manufactured containing one or more of the compounds and formulations of the invention, with one layer containing the uncombined drug for immediate release and the other layer having the drug imbedded in a hydrophilic matrix for extended-release. Three-layered tablets may also be similarly prepared, with both outer layers containing the drug for immediate release. Some commercial tablets are prepared with an inner core containing the extended-release portion of drug and an outer shell enclosing the core and containing drug for immediate release.

The invention also provides forming a complex between the active agent, e.g., one or more compounds and formulations of the invention and an ion exchange resin, whereupon the complex may be tableted, encapsulated or suspended in an aqueous vehicle. Release of the active agent is dependent on the local pH and electrolyte concentration such that the choice of ion exchange resin may be made so as to preferentially release the active agent in a given region of the alimentary canal. Delivery devices incorporating such a complex are also provided. For example, a modified release dosage form of trientine can be produced by the incorporation of trientine into complexes with an anion-exchange resin. Solutions of trientine may be passed through columns containing an ion-exchange resin to form a complex by the replacement of $H_3O^+$ ions. The resin-trientine complex is then washed and may be tableted, encapsulated, or suspended in an aqueous vehicle. The release of the trientine is dependent on the pH and the electrolyte concentration in the gastrointestinal fluid. Release is greater in the acidity of the stomach than in the less acidic environment of the small intestine. Alternative examples of this type of extended release preparation are provided by hydrocodone polistirex and chorpheniramine polistirex suspension (Medeva; Tussionex Pennkinetic Extended Release Suspension, see: Martindale 33rd Ed., p. 2145.2) and by phentermine resin capsules (Pharmanex; Ionamin Capsules see: Martindale 33rd Ed., p. 1916.1). Such resin-trientine active agent systems can additionally incorporate polymer barrier coating and bead technologies in addition to the ion-exchange mechanism. The initial dose comes from an uncoated portion, and the remainder from the coated beads. The coating does not dissolve, and release may be extended over a 12-hour period by ion exchange. The drug containing particles are minute, and may be also suspended to produce a liquid with extended-release characteristics, as well as solid dosage forms. Such preparations may also be suitable for administration, for example in depot preparations suitable for intramuscular injection.

The invention also provides a method to produce modified release preparations of one or more copper chelators, for example, trientine or salts thereof, by microencapsulation. Such microencapsulated preparations are useful for the treatment of humans and other mammals, in which copper chelation therapy is indicated. Microencapsulation is a process by which solids, liquids, or even gasses may be encapsulated into microscopic size particles through the formation of thin coatings of "wall" material around the substance being encapsulated such as disclosed in U.S. Pat. Nos. 3,488,418; 3,391,416 and 3,155,590. Gelatin (BP, USP) is commonly employed as a wall-forming material in microencapsulated preparations, but synthetic polymers such as polyvinyl alcohol (USP), ethylcellulose (BP, USP), polyvinyl chloride, and other materials may also be used (see, for example, Zentner, G. M., Rork, G. S. & Himmelstein, K. J. Osmotic flow through controlled porosity films: an approach to delivery of water soluble compounds. J Controlled Release 2:217-229 (1985); Fites, A. L., Banker, G. S. & Smolen, V. F. Controlled drug release through polymeric films. *J Pharm Sci* 59:610-613 (1970); Samuelov, Y., Donbrow, M. & Friedman, M. Sustained release of drugs from ethylcellulose-polyethylene glycol films and kinetics of drug release. *J Pharm Sci* 68:325-329 (1979)).

Encapsulation begins with the dissolving of the prospective wall material, say gelatin, in water. One or more copper chelators, for example, trientine or one or more salts thereof, is then added and the two-phase mixture is thoroughly stirred. With the material to be encapsulated broken up to the desired particle size, a solution of a second material is added, that can be acacia (BP, USP). This additive material is chosen to have the ability to concentrate the gelatin (polymer) into tiny liquid droplets. These droplets (the coacervate) then form a film or coat around the particles of the solid trientine as a consequence of the extremely low interfacial tension of the residual water or solvent in the wall material so that a continuous, tight, film-coating remains on the particle (see Ansel, H. C., Allen, L. V. and Popovich, N. G. Pharmaceutical Dosage Forms and Drug Delivery Systems, 7th Ed., Lippincott 1999, p. 233). The final dry microcapsules are free flowing, discrete particles of coated material. Of the total particle weight, the wall material usually represents between 2 and 20% (w/w). The coated particles are then admixed with tableting excipients and formed into dosage-sized tablets. Different rates of trientine release may be obtained by changing the core-to-wall ratio, the polymer used for the coating, or the method of microencapsulation (for example, see: Yazici, E., Oner, L., Kas, H. S. & Hincal, A. A. Phenytoin sodium microspheres: bench scale formulation, process characterization and release kinetics. Pharmaceut Dev Technol 1996; 1:175-183).

One of the advantages of microencapsulation is that the administered dose of one or more copper chelators, for example, trientine or salts thereof, is subdivided into small units that are spread over a large area of the gastrointestinal tract, which may enhance absorption by diminishing localized drug concentrations (see Yazici et al., supra). An example of a drug that is commercially available in a microencapsulated extended-release dosage form is potassium chloride (Micro-K Exten-caps, Wyeth-Ayerst, Martindale 33rd Ed., p 1968.1). Other useful approaches include those in which the drug is incorporated into polymeric colloidal particles or microencapsulates (microparticles, microspheres or nanoparticles) in the form or reservoir and matrix devices (see: Douglas, S. J., et al., "Nanoparticles in drug delivery," *C. R. C. Crit Rev Therap Drug Carrier Syst* 3:233-261 (1987); Oppenheim, R. C., "Solid colloidal drug delivery systems: nanoparticles." *Int J Pharm* 8:217-234 (1981); Higuchi, T. "Mechanism of sustained action medication: theoretical analysis of rate of release of solid drugs dispersed in solid matrices." *J Pharm Sci* 52:1145-1149 (1963)).

The invention also includes repeat action tablets containing one or more copper chelators, for example, trientine or salts thereof. Further examples of a method by which modified release forms of one or more copper chelators, for example, trientine or salts thereof, suitable for treatment of humans or other mammals, can be produced are provided by the incorporation of trientine into repeat action tablets. These are prepared so that an initial dose of the drug is released immediately followed later by a second dose. The tablets may be prepared with the immediate-release dose in the tablet's outer shell or coating with the second dose in the tablet's inner core, separated by a slowly permeable barrier coating. In general, the drug from the inner core is exposed to body fluids and released 4 to 6 hours after administration. An example of this type of product is proved by Repetabs (Schering Inc.). Repeat action dosage forms are suitable for the administration of one or more copper chelators, for example, trientine or salts thereof, for the indications noted herein, including but not limited to chronic conditions such as heart failure, diabetic heart disease, acute coronary syndrome, hypertensive heart disease, ischemic heart disease, coronary artery disease, peripheral arterial disease, or any form of cancer. This form of delivery is particularly suitable for delivery of trientine, since it has a rapid rate of absorption and excretion.

The invention also includes delayed-release oral dosage forms containing one or more copper chelators, for example, trientine or salts thereof. The release of one or more copper chelators, for example, trientine or salts thereof from an oral dosage form can be intentionally delayed until it reaches the intestine by way of, for example, enteric coating. Enteric coatings by themselves are not an efficient method for the delivery of copper chelators such as, for example, trientine or salts thereof including trientine dihydrochloride, because of the inability of such coating systems to provide or achieve a sustained therapeutic effect after release onset. Enteric coats are designed to dissolve or breakdown in an alkaline environment. The presence of food may increase the pH of the stomach. Therefore, the concurrent administration of enteric-coated trientine dihydrochloride with food or the presence of food in the stomach may lead to dose dumping and unwanted secondary effects. Furthermore, given the fact that, for example, trientine dihydrochloride can give rise to gastrointestinal side-effects, it would be desirable to have a drug delivery system that is capable of providing the controlled delivery of trientine dihydrochloride or other pharmaceutically acceptable salts of trientine in a predictable manner over a long period of time.

Enteric coatings also have application in the present invention when combined or incorporated with one or more of the other dose delivery formulations or devices described herein. This form of delivery conveys the advantage of minimizing the gastric irritation that may be caused in some subjects by trientine. The enteric coating may be time-dependent, pH-dependent where it breaks down in the less acidic environment of the intestine and erodes by moisture over time during gastrointestinal transit, or enzyme-dependent where it deteriorates due to the hydrolysis-catalyzing action of intestinal enzymes (see, for example, Muhammad, N. A., et al. "Modifying the release properties of Eudragit L30D," *Drug Dev Ind Pharm.* 17:2497-2509 (1991)). Among the many agents used to enteric coat tablets and capsules known to those skilled in the art are fats including triglycerides, fatty acids, waxes, shellac, and cellulose acetate phthalate although further examples of enteric coated preparations can be found in the USP.

The invention also provides drug delivery devices incorporating one or more copper chelators, for example, trientine or salts thereof, in a membrane-control system. Such devices comprise a rate-controlling membrane surrounding a drug reservoir. Following oral administration the membrane gradually becomes permeable to aqueous fluids, but does not erode or swell. The drug reservoir may be composed of a conventional tablet, or a microparticle pellet containing multiple units that do not swell following contact with aqueous fluids. The cores dissolve without modifying their internal osmotic pressure, thereby avoiding the risk of membrane rupture, and typically comprise 60:40 mixtures of lactulose: microcrystalline cellulose (w/w). Drug is released through a two-phase process, comprising diffusion of aqueous fluids into the matrix, followed by diffusion of the drug out of the matrix. Multiple-unit membrane-controlled systems typically comprise more than one discrete unit. They can contain discrete spherical beads individually coated with rate-controlling membrane and may be encapsulated in a hard gelatin shell (examples of such preparations include Contac 400; Martindale 33rd Ed., 1790.1 and Feospan; Martindale 33rd Ed., p. 1859.4). Alternatively, multiple-unit membrane-controlled systems may be compressed into a tablet (for example, Suscard; Martindale 33rd Ed., p. 2115.1). Alternative implementations of this technology include devices in which the drug substance is coated around inert sugar spheres, and devices prepared by extrusion spheronization employing a conventional matrix system. Advantages of such systems include the more consistent gastro-intestinal transit rate achieved by multiple-unit systems, and the fact that such systems infrequently suffer from catastrophic dose dumping. They are also ideal for the delivery of more than one drug at a time.

Preferred for oral delivery is a sustained release form of one or more compounds and formulations of the invention which is a matrix formation, such a matrix formation taking the form of film coated spheroids containing as active ingredient one or more copper chelators, for example, trientine or salts thereof such as trientine dihydrochloride, and a non water soluble spheronising agent. The term "spheroid" is known in the pharmaceutical art and means spherical granules having a diameter usually of between 0.01 mm and 4 mm. The spheronising agent may be any pharmaceutically acceptable material that, together with the active ingredient, can be spheronised to form spheroids. Microcrystalline cellulose is preferred. Suitable microcrystalline cellulose includes, for example, the material sold as Avicel PH 101 (Trade Mark, FMC Corporation). According to a preferred aspect of the present invention, the film-coated spheroids contain between 70% and 99% (by wt), especially between 80% and 95% (by wt), of the spheronising agent, especially microcrystalline cellulose. In addition to the active ingredient and spheronising agent, the spheroids may also contain a binder. Suitable binders, such as low viscosity, water soluable polymers, will be well known to those skilled in the pharmaceutical art. A suitable binder is, in particular polyvinylpyrrolidone in various degrees of polymerization. However, water-soluble hydroxy lower alkyl celluloses, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. Other thickening agents or binders include: the lipid type, among which are vegetable oils (cotton seed, sesame and groundnut oils) and derivatives of these oils (hydrogenated oils such as hydrogenated castor oil, glycerol behenate, the waxy type such as natural carnauba wax or natural beeswax, synthetic waxes such as cetyl ester waxes, the amphiphilic type such as polymers of ethylene oxide (polyoxyethylene glycol of high molecular weight between 4000 and 100000) or propylene and ethylene oxide copolymers (poloxamers), the cellulosic type (semisynthetic derivatives of cellulose, hydroxypropylmethylcellulose, hydroxypropylcellulose, hydroxymethylcellulose, of high molecular weight and high viscosity, gum) or any other polysaccharide such as alginic acid, the polymeric type such as acrylic acid polymers (such as carbomers), and the mineral type such as colloidal silica, bentonite.

Suitable diluents for the active ingredient in the pellets, spheroids or core are, e.g., microcrystalline cellulose, lactose, dicalcium phosphate, calcium carbonate, calcium sulphate, sucrose, dextrates, dextrin, dextrose, dicalcium phosphate dihydrate, kaolin, magnesium carbonate, magnesium oxide, maltodextrin, cellulose, microcrystalline cellulose, sorbitol, starches, pregelatinized starch, talc, tricalcium phosphate and lactose. Suitable lubricants are e.g., magnesium stearate and sodium stearyl fumarate. Suitable binding agents are e.g., hydroxypropyl methyl cellulose, polyvidone and methyl cellulose.

Suitable binders that may be included are: gum arabic, gum tragacanth, guar gum, alginic acid, sodium alginate, sodium carboxymethylcellulose, dextrin, gelatin, hydroxyethylcellulose, hydroxypropylcellulose, liquid glucose, magnesium and aluminium. Suitable disintegrating agents are starch, sodium starch glycolate, crospovidone and croscarmalose sodium. Suitable surface active are Poloxamer 188®, polysorbate 80 and sodium lauryl sulfate. Suitable flow aids are talc colloidal anhydrous silica. Suitable lubricants that may be used are glidants (such as anhydrous silicate, magnesium trisilicate, magnesium silicate, cellulose, starch, talc or tricalcium phosphate) or alternatively antifriction agents (such as calcium stearate, hydrogenated vegetable oils, paraffin, magnesium stearate, polyethylene glycol, sodium benzoate, sodium lauryl sulphate, fumaric acid, stearic acid or zinc stearate and talc). Suitable water-soluble polymers are PEG with molecular weights in the range 1000 to 6000.

Delayed release through the use of a tablet, pellet, spheroid or core itself, which besides having a filler and binder, other ancillary substances, in particular lubricants and nonstick agents, and disintegrants. Examples of lubricants and nonstick agents, which may be mentioned, are higher fatty acids and their alkali metal and alkaline-earth-metal salts, such as calcium stearate. Suitable disintegrants are, in particular, chemically inert agents. Disintegrants that may be mentioned as preferred are cross-linked polyvinylpyrrolidone, cross-linked sodium carboxymethylcelluloses, and sodium starch glycolate.

The dosage unit if oral preferably delivers more than about than 50% of a copper chelator, for example, trientine dihydrochloride, in 12 hrs at a pH of about <6.5 in a controlled manner during in vivo and in vitro dissolution. Other formulations and dose forms are set forth below.

Yet further embodiments of the invention include forms of one or more copper chelators, for example, trientine or salts thereof, incorporated into transdermal drug delivery systems, such as those described in: Transdermal Drug Delivery Systems, Chapter 10. In: Ansel, H. C., Allen, L. V. and Popovich, N. G. Pharmaceutical Dosage Forms and Drug Delivery Systems, 7th Ed., Lippincott 1999, pp. 263-278). Transdermal drug delivery systems facilitate the passage of therapeutic quantities of drug substances through the skin and into the systemic circulation to exert systemic effects, as originally described (see Stoughton, R. D. Percutaneous absorption. *Toxicol Appl Pharmacol* 7:1-8 (1965)). Evidence of percutaneous drug absorption may be found through measurable blood levels of the drug, detectable excretion of the drug and/or its metabolites in the urine, and through the clinical response of the subject to its administration. For transdermal drug delivery, it is considered ideal if the drug penetrates through the skin to the underlying blood supply without drug build up in the dermal layers (Black, C. D., "Transdermal drug delivery systems," *U.S. Pharm* 1:49 (1982)). Formulations of drugs suitable for trans-dermal delivery are known to those skilled in the art, and are described in references such as Ansel et al. (supra). Methods known to enhance the delivery of drugs by the percutaneous route include chemical skin penetration enhancers, which increase skin permeability by reversibly damaging or otherwise altering the physicochemical nature of the stratum corneum to decrease its resistance to drug diffusion (see Shah, V. P., Peck, C. C. & Williams, R. L. Skin penetration enhancement: clinical pharmacological and regulatory considerations. In: Walters, K. A. & Hadgraft, J. (Eds.) Pharmaceutical skin penetration enhancement. New York: Dekker, 1993). Among effective alterations are increased hydration of the stratum corneum and/or a change in the structure of the lipids and lipoproteins in the intercellular channels brought about through solvent action or denaturation (see Walters K. A., "Percutaneous absorption and transdermal therapy," *Pharm Tech* 10:30-42 (1986)). Skin penetration enhances suitable for formulation with trientine in Transdermal Drug Delivery Systems may be chosen from the following list: acetone, laurocapram, dimethylacetamide, dimethylformamide, dimethylsulphoxide, ethanol, oleic acid, polyethylene glycol, propylene glycol and sodium lauryl sulphate. Further skin penetration enhancers may be found in publications known to those skilled in the art (see, for example, Osborne, D. W., & Henke, J. J., "Skin penetration enhancers cited in the technical literature," *Pharm Tech* 21:50-66 (1997); Rolf, D., "Chemical and physical methods of enhancing transdermal drug delivery," *Pharm Tech* 12:130-139 (1988)).

In addition to chemical means, there are physical methods that enhance transdermal drug delivery and penetration of the compounds and formulations of the invention. These include iontophoresis and sonophoresis. Iontophoresis involves the delivery of charged chemical compounds across the skin membrane using an applied electrical field. Such methods have proven suitable for delivery of a number of drugs. Accordingly, another embodiment of the invention comprises one or more copper chelators, for example, trientine or salts thereof, formulated in such a manner suitable for administration by iontophoresisor sonophoresis. Formulations of one or more copper chelators, for example, trientine, suitable for administration by iontophoresis or sonophoresis may be in the form of gels, creams, or lotions. Transdermal delivery may utilize, among others, monolithic delivery systems, drug-impregnated adhesive delivery systems (e.g., the Latitude™ drug-in-adhesive system from 3M), active transport devices and membrane-controlled systems. Monolithic systems incorporate an active agent matrix, comprising a polymeric material in which the active agent is dispersed between backing and frontal layers. Drug impregnated adhesive delivery systems comprise an adhesive polymer in which one or more compounds and formulations of the invention and any excipients are incorporated into the adhesive polymer. Active transport devices incorporate an active agent reservoir, often in liquid or gel form, a membrane that may be rate controlling, and a driving force to propel the active agent across the membrane. Membrane-controlled transdermal systems commonly comprise an active agent reservoir, often in liquid or gel form, a membrane that may be rate controlling and backing, adhesive and/or protecting layers. Transdermal delivery dosage forms include those which substitute the trientine active ingredient, preferably trientine dihydrochloride for the diclofenic or other pharmaceutically acceptable salt thereof referred to in the transdermal delivery systems disclosed in, by way of example, U.S. Pat. Nos. 6,193,996, 6,262,121.

Topical administration of one or more compounds and formulations of the invention ingredient can be prepared as an admixture or other pharmaceutical formulation to be applied in a wide variety of ways including, but are not limited to, lotions, creams gels, sticks, sprays, ointments and pastes. These product types may comprise several types of formulations including, but not limited to solutions, emulsions, gels, solids, and liposomes. If the topical composition is formulated as an aerosol and applied to the skin as a spray-on, a propellant may be added to a solution composition. Suitable propellants as used in the art can be utilized. By way of example of topical administration of an active agent, reference is made to U.S. Pat. Nos. 5,602,125, 6,426,362 and 6,420,411.

Also included in the sustained dosage forms in accordance with the present invention are any variants of the oral forms that are adapted for suppository or other parenteral use. When rectally administered in the form of suppositories, for example, these compositions may be prepared by mixing one or more compounds and formulations of the invention with a suitable non-irritating excipient, such as cocoa butter, synthetic glyceride esters or polyethylene glycols, which are solid at ordinary temperatures, but liquidify and/or dissolve in the rectal cavity to release the drug. Suppositories are generally solid dosage forms intended for insertion into body orifices including rectal, vaginal and occasionally urethrally and can be long acting or slow release. Suppositories include a base that can include, but is not limited to, materials such as alginic acid, which will prolong the release of the pharmaceutically acceptable active ingredient over several hours (5-7). Such bases can be characterized into two main categories and a third miscellaneous group: 1) fatty or oleaginous bases, 2) water-soluble or water-miscible bases and 3) miscellaneous bases, generally combinations of lipophilic and hydrophilic substances. Fatty or oleaginous bases include hydrogenated fatty acids of vegetable oils such as palm kernel oil and cottonseed oil, fat-based compound containing compounds of glycerin with the higher molecular weight fatty acids such as palmitic and stearic acids, cocoa butter is also used where phenol and chloral hydrate lower the melting point of cocoa butter when incorporated, solidifying agents like cetyl esters wax (about 20%) or beeswax (about 4%) may be added to maintain a solid suppository. Other bases include other commercial products such as Fattibase (triglycerides from palm, palm kernel and coconut oils with self-emulsifying glycerol monostearate and poloxyl stearate), Wecobee and Witepsol bases. Water-soluble bases are generally glycerinated gelatin and Water-miscible bases are generally polyethylene glycols. The miscellaneous bases include mixtures of the oleaginous and water-soluble or water-miscible materials. An example of such a base in this group is polyoxyl 40 stearate and polyoxyethylene diols and the free glycols.

Transmucosal delivery of the compounds and formulations of the invention may utilize any mucosal membrane but commonly utilizes the nasal, buccal, vaginal and rectal tissues.

Formulations suitable for nasal administration of the compounds and formulations of the invention may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose. Compositions in solution may be neubulised by the use of inner gases and such nebulised solutions may be breathed directly from the neulising device or the nebulising device may be attached to a facemask, tent or intermittent positive pressure-breathing machine. Solutions, suspensions or powder compositions may be administered orally or nasally from devices that deliver the formulation in an appropriate manner. Formulations may be prepared as aqueous solutions for example in saline, solutions employing benzyl alcohol or other suitable preservatives, absorption promoters to enhance bioavailability, fluorocarbons, and/or other solubilising or dispersing agents known in the art.

The invention provides extended-release formulations containing one or more copper chelators, for example, trientine or salts thereof suitable for parenteral administration. Extended rates of drug action following injection may be achieved in a number of ways, including the following: crystal or amorphous drug forms having prolonged dissolution characteristics; slowly dissolving chemical complexes of the drug entity; solutions or suspensions of drug in slowly absorbed carriers or vehicles (as oleaginous); increased particle size of drug in suspension; or, by injection of slowly eroding microspheres of drug (for example, see: Friess, W., Lee, G. and Groves, M. J. Insoluble collagen matrices for prolonged delivery of proteins. *Pharmaceut Dev Technol* 1:185-193 (1996)). The duration of action of the various forms of insulin for example is based in part on its physical form (amorphous or crystalline), complex formation with added agents, and its dosage form (solution of suspension).

The copper chelator must be formulated into a stable, safe pharmaceutical composition for administration to a patient. The copper chelator is a trientine active agent. The composition can be prepared according to conventional methods by dissolving or suspending an amount of the trientine active agent ingredient in a diluent. The amount is from between 0.1 mg to 1000 mg per ml of diluent of the trientine active agent. An acetate, phosphate, citrate or glutamate buffer may be added allowing a pH of the final composition to be from 5.0 to 9.5; optionally a carbohydrate or polyhydric alcohol tonicifier and, a preservative selected from the group consisting of m-cresol, benzyl alcohol, methyl, ethyl, propyl and butyl parabens and phenol may also be added. A sufficient amount of water for injection is used to obtain the desired concentration of solution. Additional tonicifying agents such as sodium chloride, as well as other excipients, may also be present, if desired. Such excipients, however, must maintain the overall tonicity of the trientine active agent.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydroxyl ion added does not exceed the capacity of the buffer system to neutralize it.

The stability of the parenteral formulation of the present invention is enhanced by maintaining the pH of the formulation in the range of approximately 5.0 to 9.5. Other pH ranges, for example, include, 5.5 to 9.0, or 6.0 to 8.5, or 6.5 to 8.0, or 7.0 to 7.5.

The buffer used in the practice of the present invention is selected from any of the following, for example, an acetate buffer, a phosphate buffer or glutamate buffer, the most preferred buffer being a phosphate buffer.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, polyethylene glycols and physiologically compatible solvents.

A stabilizer may be included in the present formulation but, and importantly, is not needed. If included, however, a stabilizer useful in the practice of the present invention is a carbohydrate or a polyhydric alcohol. The polyhydric alcohols include such compounds as sorbitol, mannitol, glycerol, and polyethylene glycols (PEGs). The carbohydrates include, for example, mannose, ribose, trehalose, maltose, inositol, lactose, galactose, arabinose, or lactose.

Suitable stabilizers include, for example, polyhydric alcohols such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000).

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular agent will be effective in one formulation but not effective in another formulation.

A preservative is, in the common pharmaceutical sense, a substance that prevents or inhibits microbial growth and may be added to a pharmaceutical formulation for this purpose to avoid consequent spoilage of the formulation by microorganisms. While the amount of the preservative is not great, it may nevertheless effect the overall stability of the trientine active agent. Thus, even selection of a preservative can be difficult.

While the preservative for use in the practice of the present invention can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

A detailed description of each preservative is set forth in "Remington's Pharmaceutical Sciences" as well as Pharmaceutical Dosage Forms: Parenteral Medications, Vol. 1, 1992, Avis et al. For these purposes, the crystalline trientine dihydrochloride salt may be administered parenterally (including subcutaneous injections, intravenous, intramuscular, intradermal injection or infusion techniques) or by inhalation spray in dosage unit formulations containing conventional non-toxic pharmaceutically-acceptable carriers, adjuvants and vehicles.

It may also be desirable to add sodium chloride or other salt to adjust the tonicity of the pharmaceutical formulation, depending on the tonicifier selected. However, this is optional and depends on the particular formulation selected. Parenteral formulations must be isotonic or substantially isotonic otherwise significant irritation and pain would occur at the site of administration.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Generally, the composition is isotonic with the blood of the subject.

If desired, the parenteral formulation may be thickened with a thickening agent such as methyl cellulose. The formulation may be prepared in an emulsified form, either water in oil or oil in water. Any of a wide variety of pharmaceutically acceptable emulsifying agents may be employed including, for example, acacia powder, a non-ionic surfactant or an ionic surfactant.

It may also be desirable to add suitable dispersing or suspending agents to the pharmaceutical formulation these may include, for example, aqueous suspensions such as synthetic and natural gums i.e. tragacanth, acacia, alginate, dextran, sodium carboxymethylcellulose, methylcellulose, polyvinylpyrrolidone or gelatin.

The vehicle of greatest importance for parenteral products is water. Water of suitable quality for parenteral administration must be prepared either by distillation or by reverse osmosis. Only by these means is it possible to separate adequately various liquid, gas and solid contaminating substances from water. Water for injection is the preferred aqueous vehicle for use in the pharmaceutical formulation of the present invention. The water may be purged with nitrogen gas to remove any oxygen or free radicals of oxygen from the water.

It is possible that other ingredients may be present in the parenteral pharmaceutical formulation of the present invention. Such additional ingredients may include wetting agents, oils (e.g., a vegetable oil such as sesame, peanut or olive), analgesic agents, emulsifiers, antioxidants, bulking agents, tonicity modifiers, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Containers are also an integral part of the formulation of an injection and may be considered a component, for there is no container that is totally insoluble or does not in some way affect the liquid it contains, particularly if the liquid is aqueous. Therefore, the selection of a container for a particular injection must be based on a consideration of the composition of the container, as well as of the solution, and the treatment to which it will be subjected.

In order to permit introduction of a needle from a hypodermic syringe into a multiple-dose vial and provide for resealing as soon as the needle is withdrawn, each vial is sealed with a rubber closure held in place by an aluminum band.

Stoppers for glass vials, such as, West 4416/50, 4416/50 (Teflon faced) and 4406/40, Abbott 5139 or any equivalent stopper can be used as the closure for the dose vial. These stoppers pass the stopper integrity test when tested using patient use patterns, e.g., the stopper can withstand at least about 100 injections.

Each of the components of the pharmaceutical formulation described above is known in the art and is described in Pharmaceutical Dosage Forms: Parenteral Medications, Vol. 1, 2nd ed., Avis et al. Ed., Mercel Dekker, New York, N.Y. 1992, which is incorporated by reference in its entirety herein.

The manufacturing process for the above formulation involves compounding, sterile filtration and filling steps. The compounding procedure, may for example, involve the dissolution of ingredients in a specific order, such as the preservative first followed by the stabilizer/tonicity agents, buffers and then the trientine active agent or dissolving all of the ingredients forming the parenteral formulation at the same time. An example of one method of preparing a parenteral formulation for administration is the dissolution of the trientine active form, for example, trientine hydrochloride, in water and diluting the resultant mixture to 154 mM in a phosphate buffered saline.

Alternatively, parenteral formulations of the present invention are prepared by mixing the ingredients following generally accepted procedures. For example, the selected components may be mixed in a blender or other standard device to produce a concentrated mixture which may then be adjusted to the final concentration and viscosity by the addition of water, a thickening agent, a buffer, 5% human serum albumin or an additional solute to control tonicity.

Alternatively, the trientine active agent can be packaged as a dry solid and/or powder to be reconstituted with a solvent to yield a parenteral formulation in accordance with the present invention for use at the time of reconstitution.

In addition the manufacturing process may include any suitable sterilization process when developing the parenteral formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), radiant exposure and aseptic handling.

Suitable routes of parenteral administration include intramuscular, intravenous, subcutaneous, intradermal, intraarticular, intrathecal and the like. The subcutaneous route of administration is preferred. Mucosal delivery is also permissible. The dose and dosage regimen will depend upon the weight and health of the subject.

Routes for parenteral administration therefore include intravenous, intramuscular, intraperitoneal, sub dermal, and subcutaneous administration.

In addition to the above means of achieving extended drug action, the rate and duration of drug delivery may be controlled by, for example by using mechanically controlled drug infusion pumps.

The pharmaceutically acceptable active agent, for example, one or more copper chelators, such as, for example, trientine or salts thereof such as trientine dihydrochloride, can be administered in the form of a depot injection that may be formulated in such a manner as to permit a sustained release of the active ingredient. The active ingredient can be compressed into pellets or small cylinders and implanted subcutaneously or intramuscularly. The pellets, or cylinders may additionally be coated with a suitable biodegradable polymer chosen so as to provide a desired release profile. The active ingredient may alternatively be micropelleted. Active agent micropellets using bioacceptable polymers can be designed to allow release rates to be manipulated to provide a desired release profile. Alternatively, injectable depot forms can be made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations can also be prepared by entrapping the drug in liposomes, examples of which include unilamellar vesicles, large unilamellar vesicles and multilamellar vesicles. Liposomes can be formed from a variety of phospholipids, such as cholesterol, stearyl amine or phosphatidylcholines. Depot injectable formulations can also be prepared by entrapping the drug in microemulsions which are compatible with body tissue. By way of example reference is made to U.S. Pat. Nos. 6,410,041 and 6,362,190.

The invention in part provides infusion dose delivery formulations and devices, including but not limited to implantable infusion devices. Implantable infusion devices may employ inert material such as biodegradable polymers listed above or synthetic silicones for example cylastic, silicone rubber or other polymers manufactured by the Dow-Corning Corporation. The polymer may be loaded with active agent and any excipients. Implantable infusion devices may also comprise a coating of, or a portion of, a medical device wherein the coating comprises the polymer loaded with active agent and any excipient. Such an implantable infusion device may be prepared as disclosed in U.S. Pat. No. 6,309,380 by coating the device with an in vivo biocompatible and biodegradable or bioabsorbable or bioerodible liquid or gel solution containing a polymer with the solution comprising a desired dosage amount of active ingredient and any excipients. The solution is converted to a film adhering to the medical device thereby forming the implantable drug-deliverable medical device.

An implantable infusion device may also be prepared by the in situ formation of an active agent containing solid matrix as disclosed in U.S. Pat. No. 6,120,789, herein incorporated in its entirety. Implantable infusion devices may be passive or active. An active implantable infusion device may comprise an active agent reservoir, a means of allowing the active agent to exit the reservoir, for example a permeable membrane, and a driving force to propel the active agent from the reservoir. Such an active implantable infusion device may additionally be activated by an extrinsic signal, such as that disclosed in WO 02/45779, wherein the implantable infusion device comprises a system configured to deliver the active agent comprising an external activation unit operable by a user to request activation of the implantable infusion device, including a controller to reject such a request prior to the expiration of a lockout interval. Examples of an active implantable infusion device include implantable drug pumps. Implantable drug pumps include, for example, miniature, computerized, programmable, refillable drug delivery systems with an attached catheter that inserts into a target organ system, usually the spinal cord or a vessel. See Medtronic Inc. Publications: UC9603124EN NP-2687, 1997; UC199503941b EN NP-2347 182577-101, 2000; UC199801017a EN NP3273a 182600-101, 2000; UC200002512 EN NP4050, 2000; UC199900546bEN NP-3678EN, 2000. Minneapolis, Minn.: Medtronic Inc; 1997-2000. Many pumps have 2 ports: one into which drugs can be injected and the other that is connected directly to the catheter for bolus administration or analysis of fluid from the catheter. Implantable drug infusion pumps (SynchroMed EL and Synchromed programmable pumps; Medtronic) are indicated for long-term intrathecal infusion of morphine sulfate for the treatment of chronic intractable pain; intravascular infusion of floxuridine for treatment of primary or metastatic cancer; intrathecal injection (baclofen injection) for severe spasticity; long-term epidural infusion of morphine sulfate for treatment of chronic intractable pain; long-term intravascular infusion of doxorubicin, cisplatin, or methotrexate for the treatment or metastatic cancer; and long-term intravenous infusion of clindamycin for the treatment of osteomyelitis. Such pumps may also be used for the long-term infusion of one or more copper chelators, for example, for example, trientine or salts thereof, at a desired amount for a desired number of doses or steady state administration. One form of a typical implantable drug infusion pump (Synchromed EL programmable pump; Medtronic) is titanium covered and roughly disk shaped, measures 85.2 mm in diameter and 22.86 mm in thickness, weighs 185 g, has a drug reservoir of 10 mL, and runs on a lithium thionyl-chloride battery with a 6- to 7-year life, depending on use. The downloadable memory contains programmed drug delivery parameters and calculated amount of drug remaining, which can be compared with actual amount of drug remaining to access accuracy of pump function, but actual pump function over time is not recorded. The pump is usually implanted in the right or left abdominal wall. Other pumps useful in the invention include, for example, portable disposable infuser pumps (PDIPs). Alternatively, implantable infusion devices may employ liposome delivery systems such as a small unilamellar vesicles, large unilamellar vesicles, and multilamellar vesicles can be formed from a variety of phospholipids, such as cholesterol, stearyl amine or phosphatidylcholines.

The invention also includes delayed-release ocular preparations containing one or more copper chelators, for example, trientine or salts thereof. Disease of the retinal arteries, leading to leading to leakage of plasma and ultimately to diabetic retinopathy, is a leading cause of impaired vision and blindness consequent upon diabetes. Trientine therapy is effective in treating diabetic arterial disease. This aspect of the invention provides ocular preparations of trientine suitable for administration to humans for the treatment of the disease of the retinal arteries in diabetes. Such administration is expected to yield high, localized concentrations of drug, suitable for treatment of diabetic arterial disease in the retina, and diabetic retinopathy.

One of the problems associated with the use of ophthalmic solutions is the rapid loss of administered drug due to blinking of the eye and the flushing effect of lacrimal fluids. Up to 80% of an administered dose may be lost through tears and the action of nasolacrimal drainage within 5 minutes of installation. Extended periods of therapy may be achieved by formulations that increase the contact time between the medication and the corneal surface. This may be accomplished through use of agents that increase the viscosity of solutions; by ophthalmic suspensions in which the drug particles slowly dissolve; by slowly dissipating ophthalmic ointments; or by use of ophthalmic inserts. Preparations of one or more copper chelators, for example, trientine or its salts suitable for ocular administration to humans may be formulated using synthetic high molecular weight cross-linked polymers such as those of acrylic acid (e.g., Carbopol 940) or gellan gum (Gelrite; see, Merck Index 12th Ed., 4389), a compound that forms a gel upon contact with the precorneal tear film (e.g. as employed in Timoptic-XE by Merck, Inc.).

Further embodiments include delayed-release ocular preparations containing trientine in ophthalmic inserts, such as the OCUSERT system (Alza Inc.). Typically, such inserts are elliptical with dimensions of about 13.4 mm by 5.4 mm by 0.3 mm (thickness). The insert is flexible and has a drug-containing core surrounded on each side by a layer of hydrophobic ethylene/vinyl acetate copolymer membranes through which the drug diffuses at a constant rate. The white margin around such devices contains white titanium dioxide, an inert compound that confers visibility. The rate of drug diffusion is controlled by the polymer composition, the membrane thickness, and the drug solubility. During the first few hours after insertion, the drug release rate is greater than that which occurs thereafter in order to achieve initially therapeutic drug levels. The drug-containing inserts may be placed in the conjunctival sac from which they release their medication over a typical 7-d period in the treatment of diabetic retinal disease. Another form of an ophthalmic insert is a rod shaped, water soluble structure composed of hydroxypropyl cellulose in which trientine is embedded. The insert is placed into the inferior cul-de-sac of the eye once or twice daily in the treatment of diabetic retinal disease. The inserts soften and slowly dissolve, releasing the drug that is then taken up by the ocular fluids. A further example of such a device is furnished by Lacrisert (Merck Inc.).

Also targeted release delivery systems where the active agent is isolated or concentrated in a body region, tissue or site for absorption or action.

The invention also provides in part dose delivery formulations and devices formulated to enhance bioavailability of trientine active agent. This may be in addition to or in combination with any of the dose delivery formulations or devices described above.

Despite good hydrosolubility, trientine is poorly absorbed in the digestive tract and consequently its bioavailability is incomplete, and may be irregular or vary from one person to another. A therapeutically effective amount of trientine active agent is an amount capable of providing an appropriate level of trientine active agent in the bloodstream. By increasing the bioavailability of trientine active agent, a therapeutically effective level of trientine active agent may be achieved by administering lower dosages than would otherwise be necessary.

An increase in bioavailability of trientine active agent may be achieved by complexation of trientine active agent with one or more bioavailability or absorption enhancing agents or in bioavailability or absorption enhancing formulations.

The invention in part provides for the formulation of trientine active agent with other agents useful to enhance bioavailability or absorption. Such bioavailability or absorption enhancing agents include, but are not limited to, various surfactants such as various triglycerides, such as from butter oil, monoglycerides, such as of stearic acid and vegetable oils, esters thereof, esters of fatty acids, propylene glycol esters, the polysorbates, sodium lauryl sulfate, sorbitan esters, sodium sulfosuccinate, among other compounds. By altering the surfactant properties of the delivery vehicle it is possible to, for example, allow an active agent to have greater intestinal contact over a longer period of time which increases uptake and reduces side effects. Further examples of such agents include carrier molecules such as cyclodextrin and derivatives thereof, well known in the art for their potential as complexation agents capable of altering the physicochemical attributes of drug molecules. For example, cyclodextrins may stabilize (both thermally and oxidatively), reduce the volatility of, and alter the solubility of, active agents with which they are complexed. Cyclodextrins are cyclic molecules composed of glucopyranose ring units which form toroidal structures. The interior of the cyclodextrin molecule is hydrophobic and the exterior is hydrophilic, making the cyclodextrin molecule water soluble. The degree of solubility can be altered through substitution of the hydroxyl groups on the exterior of the cyclodextrin. Similarly, the hydrophobicity of the interior can be altered through substitution, though generally the hydrophobic nature of the interior allows accommodation of relatively hydrophobic guests within the cavity. Accommodation of one molecule within another is known as complexation and the resulting product is referred to as an inclusion complex. Examples of cyclodextrin derivatives include sulfobutylcyclodextrin, maltosylcyclodextrin, hydroxypropylcyclodextrin, and salts thereof. Complexation of trientine with a carrier molecule such as cyclodextrin to form an inclusion complex may thereby reduce the size of the trientine dose needed for therapeutic efficacy by enhancing the bioavailability of the administered trientine.

The invention in part provides for the formulation of trientine active agent in a microemulsions to enhance bioavailability. A microemulsion is a fluid and stable homogeneous solution composed of four major constituents, respectively, a hydrophilic phase, a lipophilic phase, at least one surfactant (SA) and at least one cosurfactant (CoSA). A surfactant is a chemical compound possessing two groups, the first polar or ionic, which has a great affinity for water, the second which contains a longer or shorter aliphatic chain and is hydrophobic. These chemical compounds having marked hydrophilic character are intended to cause the formation of micelles in aqueous or oily solution. Examples of suitable surfactants include mono-, di- and triglycerides and polyethylene glycol (PEG) mono- and diesters. A cosurfactant, also sometimes known as "co-surface-active agent", is a chemical compound having hydrophobic character, intended to cause the mutual solubilization of the aqueous and oily phases in a microemulsion. Examples of suitable co-surfactants include ethyl diglycol, lauric esters of propylene glycol, oleic esters of polyglycerol, and related compounds.

The invention in part provides for the formulation of trientine active agent with various polymers to enhance bioavailability by increasing adhesion to mucosal surfaces, by decreasing the rate of degradation by hydrolysis or enzymatic degradation of the active agent, and by increasing the surface area of the active agent relative to the size of the particle. Suitable polymers can be natural or synthetic, and can be biodegradable or non-biodegradable. Delivery of low molecular weight active agents such as trientine active agent may occur by either diffusion or degredation of the polymeric system. Representative natural polymers include proteins such as zein, modified zein, casein, gelatin, gluten, serum albumin, and collagen, polysaccharides such as cellulose, dextrans, and polyhyaluronic acid. Synthetic polymers are generally preferred due to the better characterization of degradation and release profiles. Representative synthetic polymers include polyphosphazenes, poly(vinyl alcohols), polyamides, polycarbonates, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate). Synthetically modified natural polymers include cellulose derivatives such as alkyl celluloses, hydroxyalkyl celluloses, cellulose ethers, cellulose esters, and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. Each of the polymers described above can be obtained from commercial sources such as Sigma Chemical Co., St. Louis, Mo., Polysciences, Warrenton, Pa., Aldrich Chemical Co., Milwaukee, Wis., Fluka, Ronkonkoma, N.Y., and BioRad, Richmond, Calif. or can be synthesized from monomers obtained from these suppliers using standard techniques. The polymers described above can be separately characterized as biodegradable, non-biodegradable, and bioadhesive polymers, as discussed in more detail below. Representative synthetic degradable polymers include polyhydroxy acids such as polylactides, polyglycolides and copolymers thereof, poly(ethylene terephthalate), poly(butic acid), poly(valeric acid), poly(lactide-co-caprolactone), polyanhydrides, polyorthoesters and blends and copolymers thereof. Representative natural biodegradable polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers. In general, these materials degrade either by enzymatic hydrolysis or exposure to water in vivo, by surface or bulk erosion. Examples of non-biodegradable polymers include ethylene vinyl acetate, poly (meth)acrylic acid, polyamides, polyethylene, polypropylene, polystyrene, polyvinyl chloride, polyvinylphenol, and copolymers and mixtures thereof. Hydrophilic polymers and hydrogels tend to have bioadhesive properties. Hydrophilic polymers that contain carboxylic groups (e.g., poly[acrylic acid]) tend to exhibit the best bioadhesive properties. Polymers with the highest concentrations of carboxylic groups are preferred when bioadhesiveness on soft tissues is desired. Various cellulose derivatives, such as sodium alginate, carboxymethylcellulose, hydroxymethylcellulose and methylcellulose also have bioadhesive properties. Some of these bioadhesive materials are water-soluble, while others are hydrogels. Polymers such as hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP) may be utilized to enhance the bioavailibity of drugs with which they are complexed. Rapidly bioerodible polymers such as poly(lactide-co-glycolide), polyanhydrides, and polyorthoesters, whose carboxylic groups are exposed on the external surface as their smooth surface erodes, can also be used for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone. Upon degradation, these materials also expose carboxylic groups on their external surface, and accordingly, these can also be used for bioadhesive drug delivery systems.

Other agents that may enhance bioavailability or absorption can act by facilitating or inhibiting transport across the intestinal mucosa. For example, it has long been suggested that blood flow in the stomach and intestine is a factor in determining intestinal drug absorption and drug bioavailability, so that agents that increase blood flow, such as vasodilators, may increase the rate of absorption of orally administered drugs by increasing the blood flow to the gastrointestinal tract. Vasodilators have been used in combination with other drugs. For example, in EPO Publication 106335, the use of a coronary vasodilator, diltiazem, is reported to increase oral bioavailability of drugs which have an absolute bioavailability of not more than 20%, such as adrenergic beta-blocking agents (e.g., propranolol), catecholamines (e.g., dopamine), benzodiazepine derivatives (e.g., diazepam), vasodilators (e.g., isosorbide dinitrate, nitroglycerin or amyl nitrite), cardiotonics or antidiabetic agents, bronchodilators (e.g., tetrahydroisoquinoline), hemostatics (e.g., carbazochrome sulfonic acid), antispasmodics (e.g., timepidium halide) and antitussives (e.g., tipepidine). Vasodilators therefore constitute another class of agents which may enhance the bioavailability of trientine.

Other mechanisms of enhancing bioavailability of the compounds and formulations of the invention include the inhibition of reverse active transport mechanisms. For example, it is now thought that one of the active transport mechanisms present in the intestinal epithelial cells is p-glycoprotein transport mechanism which facilitates the reverse transport of substances, which have diffused or have been transported inside the epithelial cell, back into the lumen of the intestine. It has been speculated that the p-glycoprotein present in the intestinal epithelial cells may function as a protective reverse pump which prevents toxic substances which have been ingested and diffused or transported into the epithelial cell from being absorbed into the circulatory system and becoming bioavailable. One of the unfortunate aspects of the function of the p-glycoprotein in the intestinal cell however is that it can also function to prevent bioavailability of substances which are beneficial, such as certain drugs which happen to be substrates for the p-glycoprotein reverse transport system. Inhibition of this p-glycoprotein mediated active transport system will cause less drug to be transported back into the lumen and will thus increase the net drug transport across the gut epithelium and will increase the amount of drug ultimately available in the blood. Various p-glycoprotein inhibitors are well known and appreciated in the art. These include, water soluble vitamin E; polyethylene glycol; poloxamers including Pluronic F-68; Polyethylene oxide; polyoxyethylene castor oil derivatives including Cremophor EL and Cremophor RH 40; Chrysin, (+)-Taxifolin; Naringenin; Diosmin; Quercetin; and the like.

By analogy, inhibition of a reverse active transport system of which, for example, a trientine active agent is a substrate may thereby enhance the bioavailability of said trientine active agent.

Figure 4:
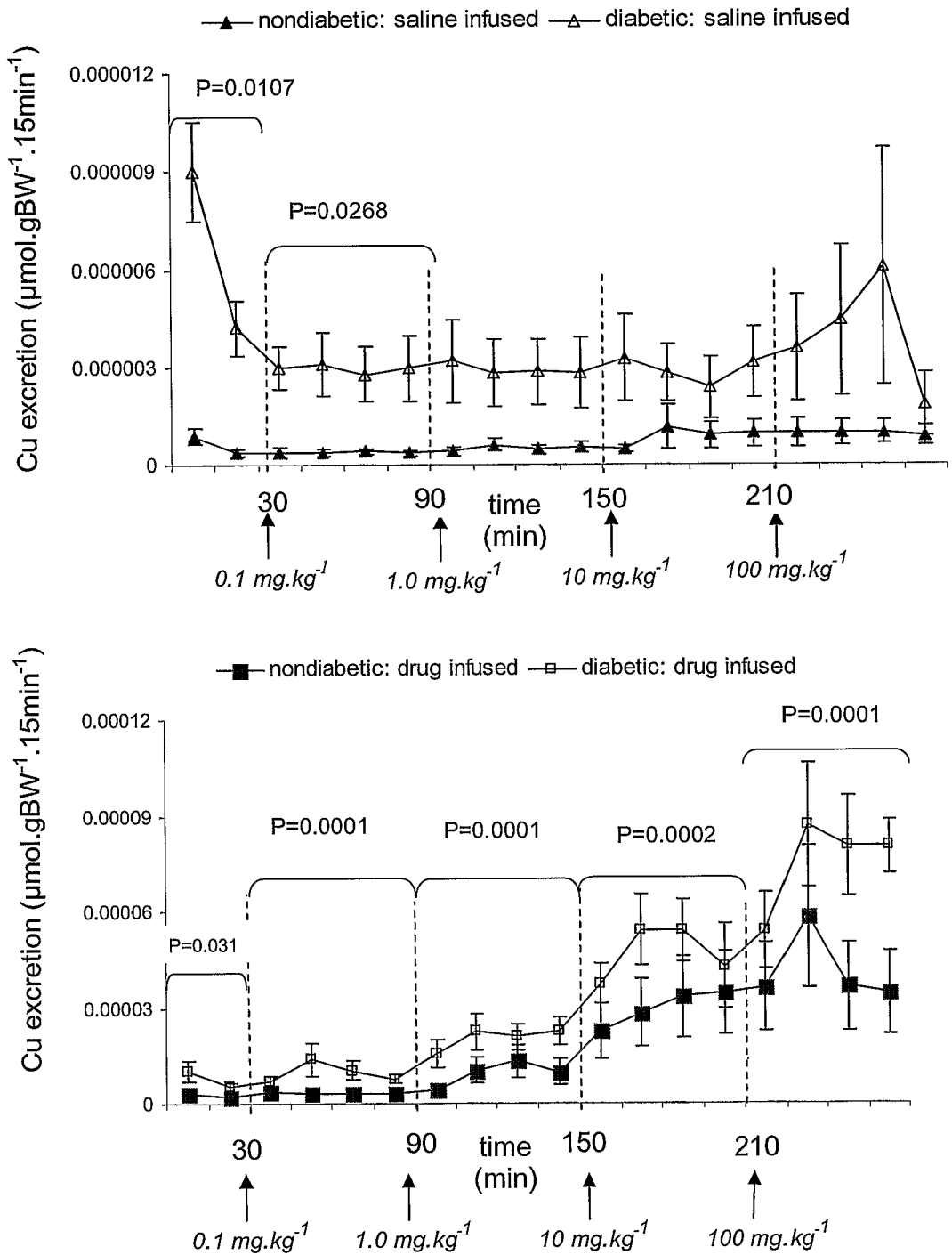
FIG. 4 shows the same information in FIG. 18 with presentation of urinary copper excretion per gram of bodyweight, wherein urinary copper excretion per gram of bodyweight in diabetic and nondiabetic animals in response to increasing doses of trientine (bottom; 0.1, 1.0, 10, 100 mg·kg$^{-1}$ in 75 μl saline followed by 125 μl saline flush injected at time shown by arrow) or an equivalent volume of saline (top), and each point represents a 15 min urine collection period (see Example 2 Methods for details); error bars show SEM and P values are stated if significant (P<0.05).

Surprisingly, as shown in Example 2, and in FIGS. 3 and 4 in particular, trientine dihydrochloride is effective at removing Cu from diabetic rats at doses far lower than have been previously shown to be effective. As can be seen in FIG. 3 and particularly in FIG. 4 which presents Cu excretion normalised to body weight, Cu excretion in the urine of diabetic rats administered trientine at a dose of 0.1 mg·kg$^{-1}$ (the lowest dose administered in the studies presented herein) is significantly increased over that of diabetic rats administered saline.

These data show that trientine active agents, including but not limited to trientine, trientine salts, trientine analogues of formulae I and II, and so on, will be effective at doses lower than, for example, the 1.2 g·d$^{-1}$ herein shown to be effective in treating human heart disease. It may be effective at doses in the order of 1/10, 1/100 and even 1/1000 of those we have already employed (e.g. in the order of 120 mg·d$^{-1}$, 12 mg·d$^{-1}$ or even 1.2 mg·d$^{-1}$).

The invention accordingly in part provides low-dose dose delivery formulations and devices comprising one or more trientine active agents, including but not limited to trientine, trientine salts, trientine analogues of formulae I and II, and so on, in an amount sufficient to provide, for example, dosage rates from 0.01 mg·kg$^{-1}$ to 5 mg·kg$^{-1}$, 0.01 mg·kg$^{-1}$ to 4.5 mg·kg$^{-1}$, 0.02 mg·kg$^{-1}$ to 4 mg·kg$^{-1}$, 0.02 to 3.5 mg·kg$^{-1}$, 0.02 mg·kg$^{-1}$ to 3 mg·kg$^{-1}$, 0.05 mg·kg$^{-1}$ to 2.5 mg·kg$^{-1}$, 0.05 mg·kg$^{-1}$ to 2 mg·kg$^{-1}$, 0.05-0.1 mg·kg$^{-1}$ to 5 mg·kg$^{1}$, 0.05-0.1 mg·kg$^{-1}$ to 4 mg·kg$^{-1}$, 0.05-0.1 mg·kg$^{-1}$ to 3 mg·kg$^{-1}$, 0.05-0.1 mg·kg$^{-1}$ to 2 mg·kg$^{-1}$, 0.05-0.1 mg·kg$^{-1}$ to 1 mg·kg$^{-1}$, and/or any other rate within the ranges as set forth.

Any such dose may be administered by any of the routes or in any of the forms herein described. It will be appreciated that any of the dose delivery formulations or devices described herein particularly for oral administration may be utilized, where applicable or desirable, in a dose delivery formulation or device for administration by any of the other routes herein contemplated or commonly employed. For example, it could be given parenterally using a dose form suitable for parenteral administration, or be delivered in an oral dosage form such as a modified release, extended release, delayed release, slow release or repeat action oral dosage form.

Another aspect of the invention, base on results of studies described herein that equate human copper values depletion against those of the STZ rat, a dosage form each with less than 250 mg of trientine dihydrochloride (or trientine active agent when expressed as the dihydrochloride). Envisaged are capsule forms having less than 250 mg trientine dihydrochloride or equivalent thereof of trientine active agent per capsule or tablets or capsules of any suitable form.

As used herein "at risk" refers to mammals subjected to a risk assessment of a kind exemplified in the Journal of American Medical Association, May 16, 2001, Volume 285 No. 19, 2486-2497 where Framingham risk scoring which takes account of age, total cholesterol, HDL cholesterol, systolic blood pressure, treatment for hypertension and cigarette smoking is mentioned and to which can be added glucose abnormalities of any of the kinds herein described.

Reference herein to "elevated" in relation to the presence of copper values in a mammal, for example, a human, will include undesired copper levels, copper to be removed for therapeutic benefit, and/or copper levels of at least about 10 mcg free copper/dL of serum when measured as discussed by Merck & Co Inc.

Histological evidence from experiments showed that six months of treatment with trientine appears to protect the hearts of diabetic Wistar rats from development of diabetic damage (cardiomyopathy), as judged by histology. The doses of trientine required for copper and iron to be excreted in the urine have also been investigated, for example, as well as possible differences between the excretion of these metals in diabetic and nondiabetic animals. For example, the excretion profiles of copper and iron in the urine of normal and diabetic rats were compared after acute intravenous administration of increasing doses of trientine. Additionally, it was ascertained whether acute intravenous administration of trientine has acute adverse cardiovascular side effects.

A better understanding of the invention will be gained by reference to the following experimental section. The following experiments are illustrative of the present invention and are not intended to limit the invention in any way.

Example 1

This Example was carried out to determine for the sake of subsequent comparison baseline physiological data relating to the effects of streptozotocin (STZ) treatment in rats, in addition to baseline physiological data from diabetic and nondiabetic rats.

All methods used in this study were approved by the University of Auckland Animal Ethics Committee and were in accordance with The Animals Protection Act and Regulations of New Zealand.

In order to induce diabetes, male Wistar rats (n=28, 303±2.9 g) were divided randomly into diabetic and nondiabetic groups. Following induction of anesthesia (5% halothane and 2 l·min$^{-1}$ O2), animals in the diabetic group received a single intravenous dose of streptozotocin (STZ, 55 mg·kg$^{-1}$ body weight, Sigma; St. Louis, Mo.) in 0.5 ml saline administered via the tail vein. Nondiabetic animals received an equivalent volume of saline. Following injection, both diabetic and nondiabetic rats were housed in like-pairs and provided with access to normal rat chow (Diet 86 pellets; New Zealand Stock Feeds, Auckland, NZ) and deionized water ad libitum. Blood glucose and body weight were measure at day 3 following STZ/saline injection and then weekly throughout the study. Diabetes was identified by polydipsia, polyuria and hyperglycemia (>11 mmol·l$^{-1}$, Advantage II, Roche Diagnostics, NZ Ltd).

Results were as follows. With regard to Effects of STZ on blood glucose and body weight, blood glucose increased to 25±2 mmol·l$^{-1}$ three days following STZ injection (Table 1).

Despite a greater daily food intake, diabetic animals lost weight whilst nondiabetic animals continued to gain weight during the 44 days following STZ/saline injection. On the day of the experiment blood glucose levels were 24±1 and 5±0 mmol·l$^{-1}$ and body weight 264±7 g and 434±9 g for diabetic and nondiabetic animals respectively.

TABLE 1

Blood glucose, body weight and food consumption in diabetic versus nondiabetic animals

|  | Diabetic | Nondiabetic |
|---|---|---|
| Body weight prior to STZ/saline | 303 ± 3 g | 303 ± 3 g |
| Blood glucose 3 days following STZ/saline | *25 ± 2 mmol · l$^{-1}$ | 5 ± 0.2 mmol · l$^{-1}$ |
| Daily food consumption | *58 ± 1 g | 28 ± 1 g |
| Blood glucose on experimental day | *24 ± 1 mmol · l$^{-1}$ | 5 ± 0.2 mmol · l$^{-1}$ |
| Body weight on experimental day | *264 ± 7 g | 434 ± 9 g |

Diabetic animals n = 14, nondiabetic animals n = 14. Values shown as mean ± SEM. Asterisk indicates a significant difference (P < 0.05).

Thus, results showed that STZ treatment resulted in elevated blood glucose, increased food intake, and decreased body weight consistent with induction of diabetes.

Example 2

This Example assessed the effect of acute intravenous administration of increasing doses of trientine on the excretion profiles of copper and iron in the urine of diabetic and nondiabetic rats.

Six to seven weeks (mean=44±1 days) after administration of STZ, animals underwent either a control or drug experimental protocol. All animals were fasted overnight prior to surgery but continued to have ad libitum access to deionized water. Induction and maintenance of surgical anesthesia was by 3-5% halothane and 2 l·min$^{-1}$ O2. The femoral artery and vein were cannulated with a solid-state blood pressure transducer (Mikrotip™ 1.4F, Millar Instruments, Texas, USA) and a saline filled PE 50 catheter respectively. The ureters were exposed via a midline abdominal incision, cannulated using polyethylene catheters (external diameter 0.9 mm, internal diameter 0.5 mm) and the wound sutured closed. The trachea was cannulated and the animal ventilated at 70-80 breaths·min$^{-1}$ with air supplemented with O2 (Pressure Controlled Ventilator, Kent Scientific, Connecticut, USA). The respiratory rate and end-tidal pressure (10-15 cmH2O) were adjusted to maintain end-tidal CO2 at 35-40 mmHg (SC-300 CO2 Monitor, Pryon Corporation, Wisconsin, USA). Body temperature was maintained at 37° C. throughout surgery and the experiment by a heating pad. Estimated fluid loss was replaced with intravenous administration of 154 mmol·l$^{-1}$ NaCl solution at a rate of 5 ml·kg$^{-1}$·h$^{-1}$.

Following surgery and a 20 min stabilization period, the experimental protocol was started. Trientine was administered intravenously over 60 s in hourly doses of increasing concentration (0.1, 1.0, 10 and 100 mg·kg-1 in 75 µl saline followed by 125 µl saline flush). Control animals received an equivalent volume of saline. Urine was collected in 15 min aliquots throughout the experiment in pre-weighed polyethylene epindorf tubes. At the end of the experiment a terminal blood sample was taken by cardiac puncture and the separated serum stored at −80° C. until future analysis. Hearts were removed through a rapid mid-sternal thoracotomy and processed as described below.

Mean arterial pressure (MAP), heart rate (HR, derived from the MAP waveform) oxygen saturation (Nonin 8600V Pulse Oximeter, Nonin Medical Inc., Minnesota, USA) and core body temperature, were all continuously monitored throughout the experiment using a PowerLab/16s data acquisition module (AD Instruments, Australia). Calibrated signals were displayed on screen and saved to disc as 2 s averages of each variable.

Urine and tissue analysis was carried out as follows. Instrumentation: A Perkin Elmer (PE) Model 3100 Atomic Absorption Spectrophotometer equipped with a PE HGA-600 Graphite Furnace and PE AS-60 Furnace Autosampler was used for Cu and Fe determinations in urine. Deuterium background correction was employed. A Cu or Fe hollow-cathode lamp (Perkin Elmer Corporation) was used and operated at either 10 W (Cu) or 15 W (Fe). The 324.8 nm atomic line was used for Cu and the 248.3 nm atomic line for Fe. The slit width for both Cu and Fe was 0.7 nm. Pyrolytically coated graphite tubes were used for all analyses. The injection volume was 20 µL. A typical graphite furnace temperature program is shown below:

| GF-AAS temperature program | | | | |
|---|---|---|---|---|
| Procedure | Temp/° C. | Ramp/s | Hold/s | Int. Flow/mL min$^{-1}$ |
| Drying | 90 | 1 | 5 | 300 |
|  | 120 | 60 | 5 | 300 |
| Pre-treatment | 1250* | 20 | 10 | 300 |
|  | 20 | 1 | 10 | 300 |
| Atomization-Cu/Fe | 2300/2500 | 1 | 8 | 0 |
| Post-treatment | 2600 | 1 | 5 | 300 |

*A pre-treatment temperature of 1050° C. was used for tissue digest analyses (see Example 3)

Reagents:

All reagents used were of the highest purity available and at least of analytical grade. GF-AAS standard working solutions of Cu and Fe were prepared by stepwise dilution of 1000 mg·l$^{-1}$ (Spectrosol standard solutions; BDH). Water was purified by a Millipore Milli-Q ultra-pure water system to a resistivity of 18 MΩ.

Sample Pretreatment was Carried Out as Follows.

Urine: Urine was collected in pre-weighed 1.5 ml micro test tubes (eppendorf). After reweighing, the urine specimens were centrifuged and the supernatant diluted 25:1 with 0.02 M 69% Aristar grade HNO$_3$. The sample was stored at 4° C. prior to GF-AAS analysis. If it was necessary to store a sample for a period in excess of 2 weeks, it was frozen and kept at −20° C. Serum: Terminal blood samples were centrifuged and serum treated and stored as per urine until analysis. From the trace metal content of serum from the terminal blood sample and urine collected over the final hour of the experiment, renal clearance was calculated using the following equation:

$$\text{renal clearance of trace metal}(\mu l \cdot min^{-1}) = \frac{\text{concentration of metal in urine}(\mu g \cdot \mu l^{-1}) * \text{rate of urine flow}(\mu l \cdot min^{-1})}{\text{concentration of metal in serum}(\mu g \cdot \mu l^{-1})}$$

Statistical analyses were carried out as follows. All values are expressed as mean±SEM and P values<0.05 were considered statistically significant. Student's unpaired t-test was initially used to test for weight and glucose differences between the diabetic and control groups. For comparison of responses during drug exposure, statistical analyses were performed using analysis of variance (Statistics for Windows v.6.1, SAS Institute Inc., California, USA). Subsequent statistical analysis was performed using a mixed model repeated measures ANOVA design (see Example 4).

The results were as follows. With regard to cardiovascular variables during infusion, baseline levels of MAP during the control period prior to infusion were not significantly different between nondiabetic and diabetic animals (99±4 mmHg). HR was significantly lower in diabetic than nondiabetic animals (287±11 and 364±9 bpm respectively, P<0.001). Infusion of trientine or saline had no effect on these variables except at the highest dose where MAP decreased by a maximum of 19±4 mmHg for the 2 min following administration and returned to pre-dose levels within 10 min. Body temperature and oxygen saturation remained stable in all animals throughout the experiment.

Figure 16:
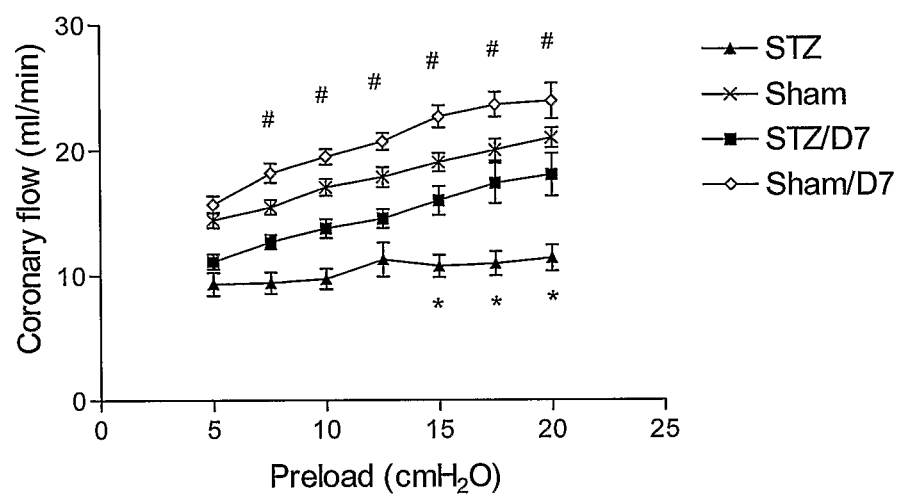
FIG. 16 is a diagram showing coronary flow in animals as measured in Example 5.
Figure 17:
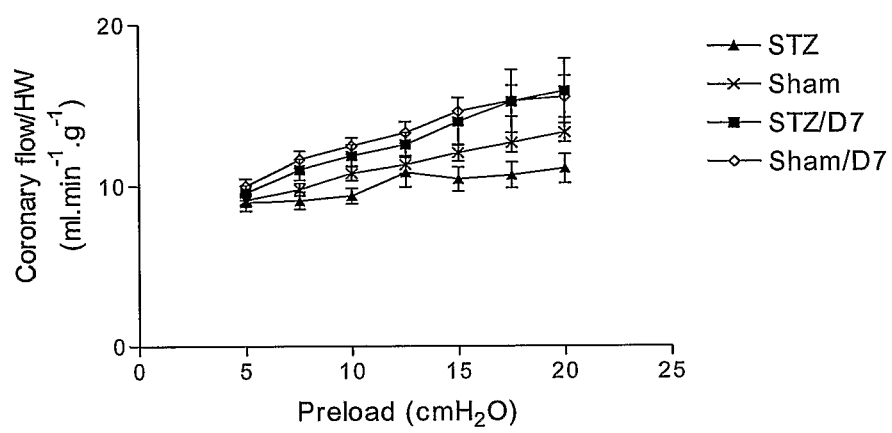
FIG. 17 is a diagram showing coronary flows normalized to final cardiac weight in animals as measured in Example 5.

With regard to urine excretion, diabetic animals consistently excreted significantly more urine than nondiabetic animals except in response to the highest dose of drug (100 mg·kg$^{-1}$) or equivalent volume of saline (FIG. 16). Administration of the 100 mg·kg$^{-1}$ dose of trientine also increased urine excretion in nondiabetic animals to greater than that of nondiabetic animals receiving the equivalent volume of saline (FIG. 17). This effect was not seen in diabetic animals.

Figure 18:
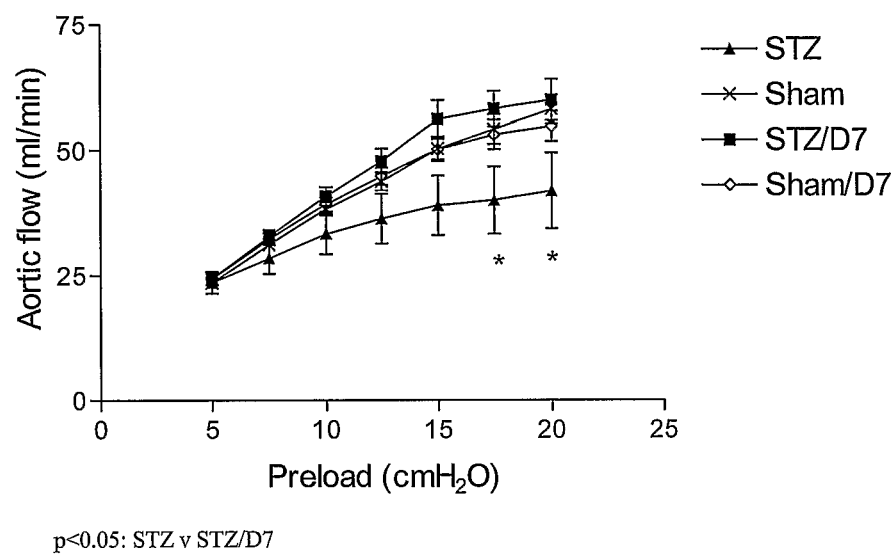
FIG. 18 is a diagram showing aortic flow in animals as measured in Example 5.
Figure 19:
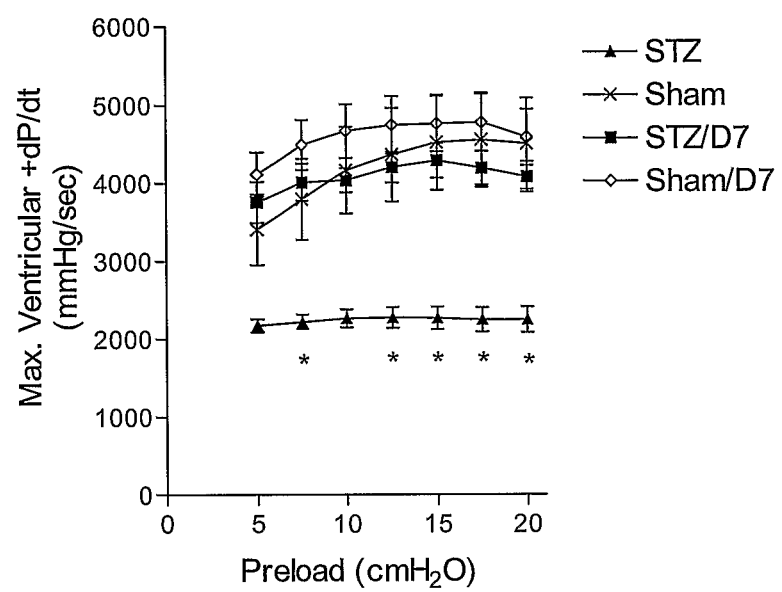
FIG. 19 is a diagram showing the maximum rate of positive change in pressure development in the ventricle with each cardiac cycle (contraction) in animals as measured in Example 5.

With regard to urinary excretion of Cu and Fe analysis of the dose response curves showed that, at all doses, diabetic and nondiabetic animals receiving drug excreted more Cu than animals receiving an equivalent volume of saline (FIG. 18). To provide some correction for the effects of lesser total body growth of the diabetic animals, and thus to allow more appropriate comparison between diabetic and nondiabetic animals, excretion rates of trace elements were also calculated per gram of body weight. FIG. 19 shows that diabetic animals had significantly greater copper excretion per gram of body weight in response to each dose of drug than did nondiabetic animals. The same pattern was seen in response to saline, however the effect was not always significant.

Figure 20:
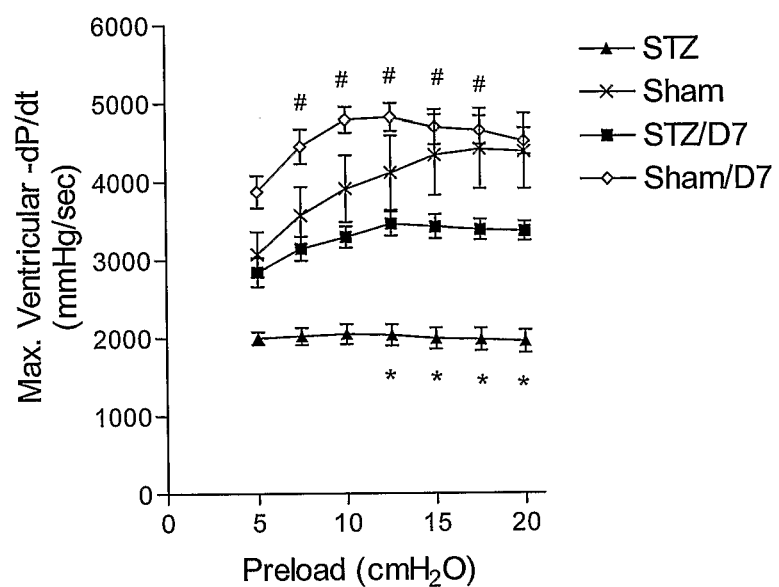
FIG. 20 is a diagram showing the maximum rate of decrease in pressure in the ventricle with each cardiac cycle (relaxation) in animals as measured in Example 5.
Figure 21:
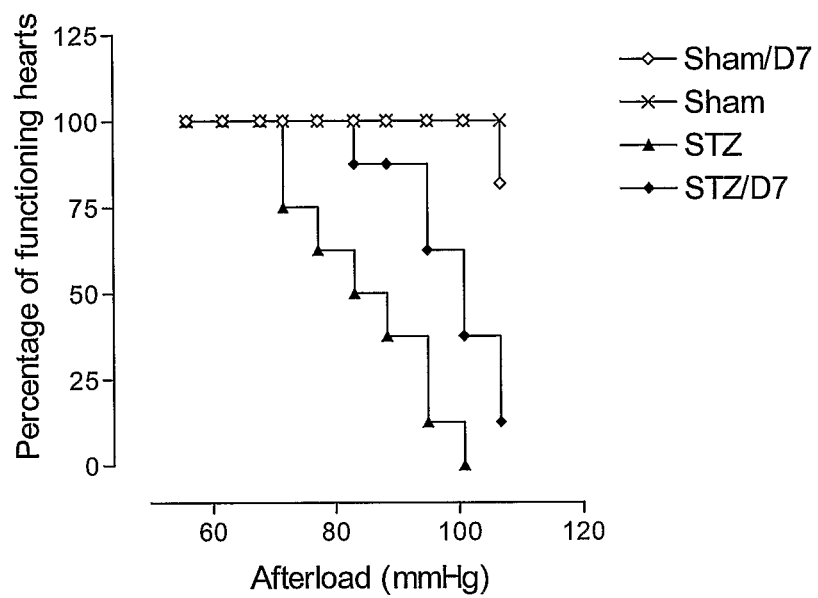
FIG. 21 shows the percentage of functional surviving hearts at each after-load in animals as measured in Example 5.

Total copper excreted over the entire duration of the experiment was significantly increased in both nondiabetic and diabetic animals administered trientine compared with their respective saline controls (FIG. 20). Diabetic animals receiving drug also excreted more total copper per gram of body weight than nondiabetic animals receiving drug. The same significant trend was seen in response to saline administration (FIG. 21).

Figure 22:
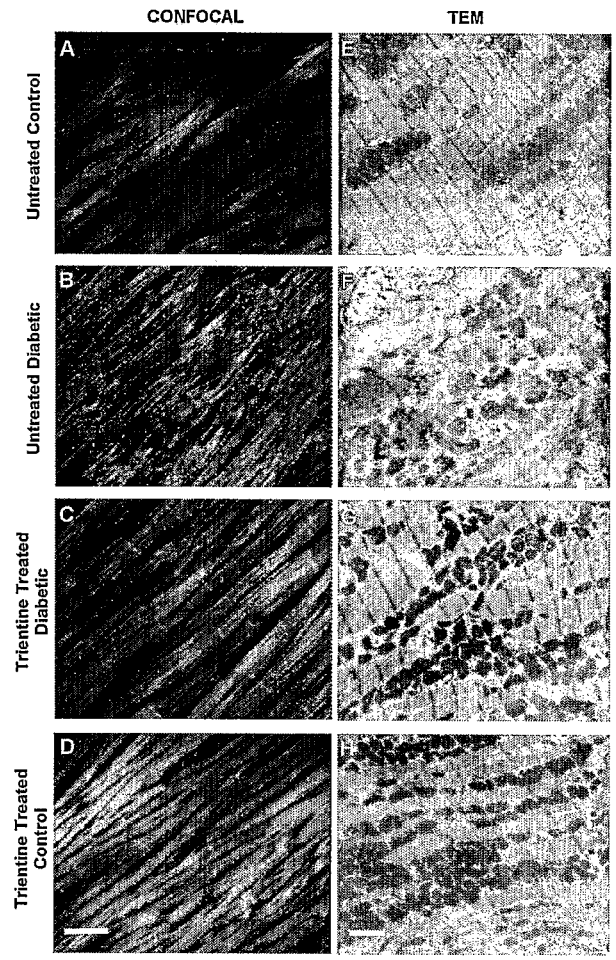
FIG. 22 shows the structure of LV-myocardium from STZ-diabetic and matched non-diabetic control rats following 7-w oral trientine treatment, wherein cardiac sections were cut following functional studies. Each image is representative of 5 independent sections per heart ×3 hearts per treatment. a-d, Laser confocal images of 120-μM LV sections co-stained for actin (Phalloidin-488, orange) and immunostained for β$_1$-integrin (CY5-conjugated secondary antibody, purple) (scale-bar=33 μm). a, Untreated-control; b, Untreated-diabetic; c, Trientine treated diabetic; d, Trientine-treated non-diabetic control. e-h, TEM images of corresponding 70-nM sections stained with uranyl acetate/lead citrate (scale-bar=158 nm); e, Untreated-control; f, Untreated-diabetic; g, Trientine-treated diabetic; h, Trientine-treated non-diabetic control.
Figure 23:
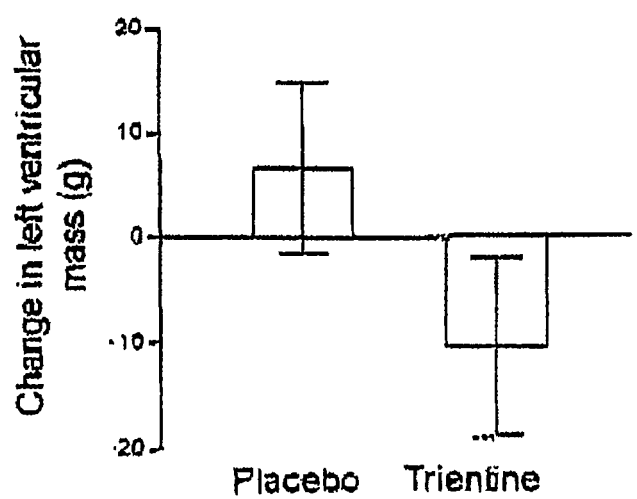
FIG. 23 shows effect of 6 months' oral trientine treatment on LV mass in humans with T2DM, wherein trientine (600 mg twice-daily) or matched placebo were administered to subjects with diabetes (n=15) or matched controls (n=15) in a double-blind, parallel-group study, and wherein differences in LV mass (g; mean and 95% confidence interval) were determined by tagged-cardiac MRI.
Figure 24:
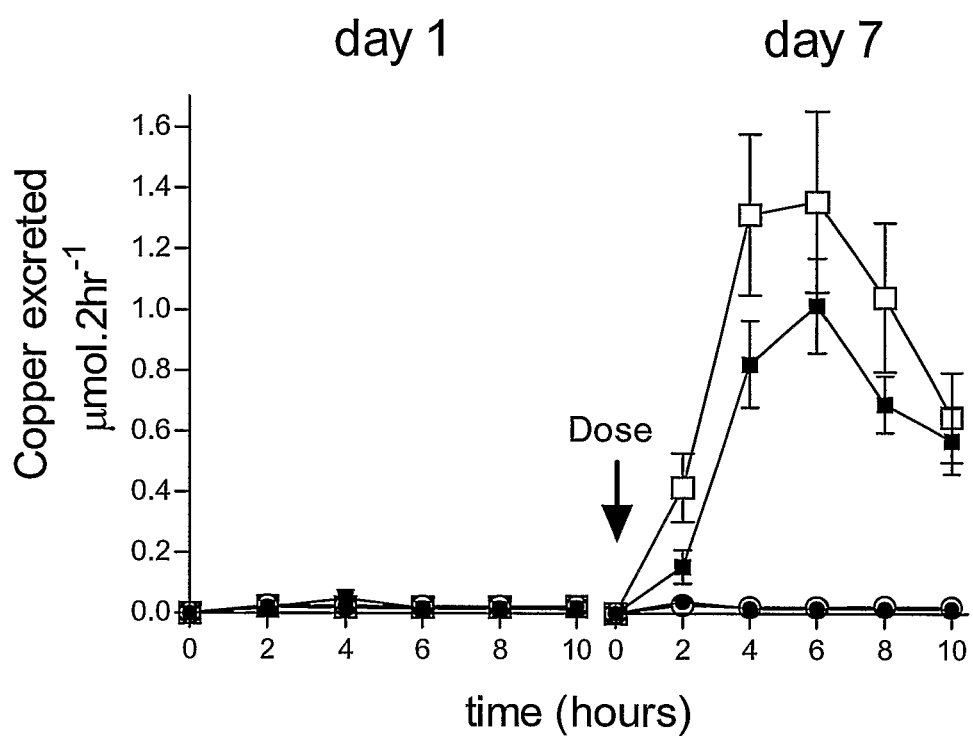
FIG. 24 shows a randomized, double blind, placebo-controlled trial comparing effects of oral trientine and placebo on urinary Cu excretion from male humans with uncomplicated T2DM and matched non-diabetic controls, wherein urinary Cu excretion ($\mu mol \cdot 2 \ h^{-1}$ on day 1 (baseline) and day 7 following a single 2.4-g oral dose of trientine or matched placebo to subjects described in Table 9, placebo-treated T2DM, ○, placebo-treated control, ●, trientine-treated T2DM, □; trientine treated control, ■. Cu excretion from T2DM following trientine-treatment was significantly greater than that from trientine-treated non-diabetic controls (P<0.05).
Figure 25:
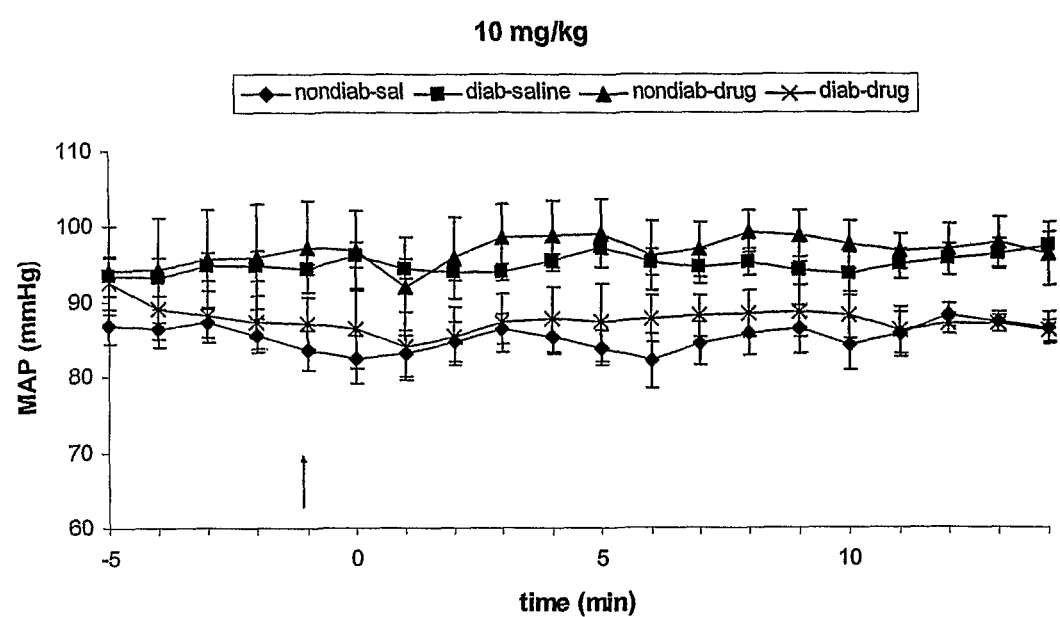
FIG. 25 shows mean arterial pressure (MAP) response in diabetic and nondiabetic animals to 10 $mg \cdot kg^{-1}$ Trientine in 75 μl+125 μl saline flush (or an equivalent volume of saline). Each point represents one minute averages of data points collected every 2 seconds. The time of drug (or saline) administration is indicated by the arrow. Error bars show SEM.

In comparison, iron excretion in both diabetic and nondiabetic animals receiving trientine was not greater than animals receiving an equivalent volume of saline (FIG. 22). Analysis per gram of body weight shows diabetic animals receiving saline excrete significantly more iron than nondiabetic animals, however this trend was not evident between diabetic and nondiabetic animals receiving trientine (FIG. 23). Total iron excretion in both diabetic and nondiabetic animals receiving drug was not different from animals receiving saline (FIG. 24). In agreement with analysis of dose response curves, total iron excretion per gram of body weight was significantly greater in diabetic animals receiving saline than nondiabetic animals but this difference was not seen in response to trientine (FIG. 25).

Electron paramagnetic resonance spectroscopy showed that the urinary Cu from drug-treated animals was mainly complexed as trientine-Cu$^{II}$ (FIG. 28), indicating that the increased tissue Cu in diabetic rats is mainly divalent. These data indicate that rats with severe hyperglycaemia develop increased systemic $Cu^{II}$ that can be extracted by selective chelation.

With regard to Serum content and renal clearance of Cu and Fe, while there was no significant difference in serum copper content, there was a significant increase in renal clearance of copper in diabetic animals receiving drug compared with diabetic animals receiving saline (Table 2). The same pattern was seen in nondiabetic animals, although the trend was not statistically significant (P=0.056). There was no effect of drug or state (diabetic versus nondiabetic) on serum content or renal clearance of iron.

TABLE 2

Serum content and renal clearance of Cu and Fe in diabetic and nondiabetic animals receiving drug or saline.

|  | 1.1.a.a.1 diabetic trientine n = 6 | 1.1.a.a.1 diabetic Saline n = 7 | 1.1.a.a.2 nondiabetic trientine n = 4 | 1.1.a.a.2 nondiabetic Saline n = 7 |
|---|---|---|---|---|
| Serum Cu ($\mu g \cdot \mu l^{-1} \times 10^{-4}$) | 7.56 ± 0.06 | 9.07 ± 1.74 | 7.11 ± 0.4 | 7.56 ± 0.62 |
| Serum Fe ($\mu g \cdot \mu l^{-1} \times 10^{-4}$) | 35.7 ± 7.98 | 63.2 ± 16.4 | 33.6 ± 1.62 | 31.4 ± 8.17 |
| Renal clearance Cu ($\mu l \cdot min^{-1}$) | *28.5 ± 4.8 | 1.66 ± 0.82 | 19.9 ± 6.4 | 0.58 ± 0.28 |
| Renal clearance Fe ($\mu l \cdot min^{-1}$) | 0.25 ± 0.07 | 0.38 ± 0.15 | 0.46 ± 0.22 | 0.11 ± 0.03 |

Values shown as mean ± SEM. Asterisk indicates a significant difference (P < 0.05) between diabetic animals receiving trientine and diabetic animals receiving an equivalent volume of saline.

In summary, acute intravenous administration of trientine significantly increased total copper excretion in both nondiabetic and diabetic animals compared with their respective saline controls. Furthermore, following acute intravenous administration of increasing doses of trientine, diabetic animals had significantly greater copper excretion per gram of body weight than did nondiabetic animals. In contrast, total iron excretion in both diabetic and nondiabetic animals receiving drug was not different from animals receiving saline.

Example 3

This example was carried out to determine the effect of acute intravenous administration of increasing doses of trientine on the copper and iron content of cardiac tissue in normal and diabetic rates.

Methods were carried out as follows. Spectrophotometric analysis was conducted as described in Example 2. Cu, Fe and Zn in tissue digests were determined at Hill Laboratories (Hamilton, New Zealand) using either a PE Sciex Elan-6000 or PE Sciex Elan-6100 DRC ICP-MS. The operating parameters are summarized in the Table below.

Instrumental operating parameters for ICP-MS

| Parameter | Value |
|---|---|
| Inductively coupled plasma | |
| Radiofrequency power | 1500 W |
| Argon plasma gas flow rate | 15 $l \cdot min^{-1}$ |
| Argon auxiliary gas flow rate | 1.2 $l \cdot min^{-1}$ |
| Argon nebuliser gas flow rate | 0.89 $l \cdot min^{-1}$ |

-continued

Instrumental operating parameters for ICP-MS

| Parameter | Value |
|---|---|
| Interface | |
| Sampler cone and orifice diameter | Ni/1.1 mm |
| Skimmer cone and orifice diameter | Ni/0.9 mm |
| Data acquisition parameters | |
| Scanning mode | Peak hopping |
| Dwell time | 30 ms (Cu, Zn)/100 ms (Fe) |
| Sweeps/replicate | 20 |
| Replicates | 3 |
| Sample uptake rate | 1 $ml \cdot min^{-1}$ |

Reagents were as follows. Standard Reference Material 1577b Bovine Liver was obtained from the National Institute of Standards and Technology and used to evaluate the efficiency of tissue digestion. The results obtained are reported below:

GF-AAS and ICP-MS results for NIST SRM 1577b bovine liver*

| Element | Certified value | GF-AAS | ICP-MS |
|---|---|---|---|
| Cu | 160 ± 8 | 142 ± 12 | 164 ± 12 |
| Fe | 184 ± 15 | 182 ± 21 | 166 ± 14 |
| Zn | 127 ± 16 | — | 155 ± 42 |

*Measured in $\mu g \cdot g^{-1}$ of dry matter.

Sample pre-treatment was carried out as follows. Heart: Following removal from the animal, the heart was cleaned of excess tissue, rinsed in buffer to remove excess blood, blotted dry and a wet ventricular weight recorded. Using titanium instruments a segment of left ventricular muscle was dissected and placed in a pre-weighed 5.0 ml polystyrene tube. The sample was freeze-dried overnight to constant weight before 0.45 ml of 69% Aristar grade $HNO_3$ was added. The sample tube was heated in a water bath at 65° C. for 60 minutes. The sample was brought to 4.5 ml with Milli-Q $H_2O$. The resulting solution was diluted 2:1 in order to reduce the $HNO_3$ concentration below the maximum permitted for ICP-MS analysis.

The results were as follows. With regard to the metal content of cardiac tissue, wet heart weights in diabetic animals were significantly less than those in nondiabetic animals while heart/body weight ratios were increased (see Table 3). Cardiac tissue from some animals was also analysed for Cu and Fe content. There was no significant difference in content of copper between diabetic and nondiabetic animals receiving saline or trientine. Iron content of the non-diabetic animals administered saline was significantly greater than that of the diabetic animals administered saline (see Table 3).

TABLE 3

Heart weight, heart weight/body weight ratios and trace metal content of heart tissue in diabetic versus nondiabetic animals

|  | Diabetic | Nondiabetic |
|---|---|---|
| Wet heart weight | *0.78 ± 0.02 g | 1.00 ± 0.02 g |
| Heart weight/body weight | *2.93 ± 0.05 $mg \cdot g^{-1}$ | 2.30 ± 0.03 $mg \cdot g^{-1}$ |
| Cu content $\mu g \cdot g^{-1}$ dry tissue | | |
| Trientine treated | 24.7 ± 1.5 | 27.1 ± 1.0 |
| Saline treated | 21.3 ± 0.9 | 27.2 ± 0.7 |
| Fe content $\mu g \cdot g^{-1}$ dry tissue | | |

TABLE 3-continued

Heart weight, heart weight/body weight ratios and trace metal content of heart tissue in diabetic versus nondiabetic animals

|  | Diabetic | Nondiabetic |
|---|---|---|
| Trientine treated | 186 ± 46 | 235 ± 39 |
| Saline treated | †180 ± 35 | 274 ± 30 |

Diabetic animals: n = 14; nondiabetic animals: n = 14. Values shown as mean ± SEM.
Asterisk indicates a significant difference (P < 0.05) between diabetic and non-diabetic animals.
†indicates a significant difference (P < 0.05) between diabetic and non-diabetic animals receiving saline.

In summary, it was demonstrated that acute intravenous administration of increasing doses of trientine had no significant effect on the copper content of cardiac tissue in normal and diabetic rates.

Example 4

In this Example, a mixed linear model was applied to the data generated above in Examples 1-3.

Methods were as follows. With regard to statistical analysis using a mixed linear model, data for each dose level were analyzed using a mixed linear model (PROC MIXED; SAS, Version 8). The model included diabetes, drug and their interaction as fixed effects, time as a repeated measure, and rats as the subjects in the dataset. Complete independence was assumed across subjects. The full model was fitted to each dataset using a maximum likelihood estimation method (REML) fits mixed linear models (L e., fixed and random effects models). A mixed model is a generalization of the standard linear model, the generalization being that one can analyze data generated from several sources of variation instead of just one. A level of significance of 0.05 was used for all tests. Results were as follows.

With regard to copper, diabetic rats excreted significantly higher levels of copper across all dose levels (see FIG. 27). Baseline copper excretion was also significantly higher in diabetic rats compared to nondiabetic rats. There was no difference at baseline levels between the drug and saline groups. The interaction effect for the model was significant at dose levels of 1.0 mg·kg$^{-1}$ and above. The presence of a significant interaction term means that the influence of one effect varies with the level of the other effect. Therefore, the outcome of a significant interaction between the diabetes and drug factors is increased copper excretion above the predicted additive effects of these two factors.

With regard to iron, diabetic rats in the saline only group excreted significantly higher levels of iron at all dose levels. This resulted in all factors in the model being significant across all dose levels.

In sum, the acute effect of intravenous trientine administration on the cardiovascular system and urinary excretion of copper and iron was studied in anesthetized, diabetic (6 weeks of diabetes, Streptozotocin induced) and nondiabetic rats. Animals were assigned to one of four groups: diabetic+trientine, diabetic+saline, nondiabetic+trientine, nondiabetic+saline. Drug, or an equivalent volume of saline, was administered hourly in doses of increasing strength (0.1, 1.0, 10, 100 mg·kg$^{-1}$) and urine was collected throughout the experiment in 15 min aliquots. A terminal blood sample was taken and cardiac tissue harvested. Analysis of urine samples revealed: (1) At all drug doses, diabetic and nondiabetic animals receiving drug excreted more Cu (µmol) than animals receiving an equivalent volume of saline; (2) When analyzed per gram of bodyweight, diabetic animals excreted significantly more copper (µmol·gBW$^{-1}$) at each dose of trientine than did nondiabetic animals. The same pattern was seen in response to saline but the effect was not significant at every dose; (3) At most doses, in diabetic animals iron excretion (µmol) was greater in animals administered saline than in those administered drug. In nondiabetic animals there was no difference between iron excretion in response to saline or trientine administration; (4) Analysis per gram of body weight shows no difference between iron excretion in non-diabetic and diabetic animals receiving trientine. Diabetic animals receiving saline excrete more iron per gram of bodyweight than nondiabetic animals receiving saline; (5) Analysis of heart tissue showed no significant difference in total copper content between diabetic and nondiabetic animals, nor any effect of drug on cardiac content of iron and copper; and (6) Renal clearance calculations showed a significant increase in clearance of copper in diabetic animals receiving trientine compared with diabetic animals receiving saline. The same trend was seen in nondiabetic animals but the affect was not significant. There was no effect of trientine on renal clearance of iron.

There were no adverse cardiovascular effects were observed after acute administration of trientine. Trientine treatment effectively increases copper excretion in both diabetic and nondiabetic animals. The excretion of copper in urine following trientine administration is greater per gram of bodyweight in diabetic than in nondiabetic animals. Iron excretion was not increased by trientine treatment in either diabetic or nondiabetic animals.

Example 5

Experiments relating to the efficacy of trientine to restore cardiac function in STZ diabetic rats were carried out. As noted above, histological evidence showed that treatment with trientine appears to protect the hearts of diabetic Wistar rats from development of cardiac damage (diabetic cardiomyopathy), as judged by histology. However, it was unknown whether this histological improvement may lead to improved cardiac function.

This experiment was carried out to compare cardiac function in trientine-treated and non-treated, STZ diabetic and normal rats using an isolated-working-rodent heart model.

Methods were as follows. The animals used in these experiments received care that complied with the "Principles of Laboratory Animal Care" (National Society for Medical Research), and the University of Auckland Animal Ethics Committee approved the study.

Male albino Wistar rats weighing 330-430 g were assigned to four experimental groups as shown in Table 4.

TABLE 4

Experimental groups

| Group | Code | N | Treatment |
|---|---|---|---|
| Group A | STZ | 8 | Diabetes for 13 weeks |
| Group B | STZ/D7 | 8 | Diabetes for 13 weeks (Drug therapy week 7-13) |
| Group C | Sham | 9 | Non-diabetic controls |
| Group D | Sham/D7 | 11 | Non-diabetic controls (Drug therapy week 7-13) |

STZ = Streptozotocin;
D7 = trientine treatment for 7 consecutive weeks commencing 6 weeks after the start of the experiment.

Diabetes was induced by intravenous streptozotocin (STZ; Sigma; St. Louis, Mo.). All rats were given a short inhalational anesthetic (Induction: 5% halothane and 2 L/min oxygen, maintained on 2% halothane and 2 L/min oxygen). Those in the two diabetic groups then received a single intravenous bolus dose of STZ (57 mg/kg body weight) in 0.5 ml of 0.9% saline administered via a tail vein. Non-diabetic sham-treated animals received an equivalent volume of 0.9% saline. Diabetic and non-diabetic rats were housed in like-pairs and provided with free access to normal rat chow (Diet 86 pellets; New Zealand Stock Feeds, Auckland, NZ) and deionized water ad libitum. Each cage had two water bottles on it to ensure equal access to water or drug for each animal. Animals were housed at 21 degrees and 60% humidity in standard rat cages with a sawdust floor that was changed daily.

Blood glucose was measured in tail-tip capillary blood samples (Advantage II, Roche Diagnostics, NZ Ltd). Sampling was performed on all groups at the same time of the day. Blood glucose and body weight were measured on day 3 following STZ/saline injection and then weekly throughout the study. Diabetes was confirmed by presence of polydipsia, polyuria and hyperglycemia (>11 mmol·L$^{-1}$).

In the drug treated diabetic group, trientine was prepared in the drinking water for each cage at a concentration of 50 mg/L. The trientine-containing drinking water was administered continuously from the start of week 7 until the animal was sacrificed at the end of week 13. In the case of the Sham/D7 non-diabetic group that drank less water per day than diabetic animals, the drug concentration in their drinking water was adjusted so that they consumed approximately the same dose as the corresponding STZ/D7 group. Trientine treated animals ingested mean drug doses of between 8 to 11 mg per day.

At the time the drug started in the diabetic group the diabetic animals were expected to have to have established cardiomyopathy, as shown by preliminary studies (data not shown) and confirmed in the literature. See Rodrigues B, et al., *Diabetes* 37(10):1358-64 (1988).

On the last day of the experiment, animals were anesthetized (5% halothane and 2 L·min$^{-1}$ O$_2$), and heparin (500 IU·kg$^{-1}$) (Weddel Pharmaceutical Ltd., London) administered intravenously via tail vein. A 2 ml blood sample was then taken from the inferior vena cava and the heart was then rapidly excised and immersed in ice-cold Krebs-Henseleit bicarbonate buffer to arrest contractile activity. Hearts were then placed in the isolated perfused working heart apparatus.

The aortic root of the heart was immediately ligated to the aortic cannula of the perfusion apparatus. Retrograde (Langendorff) perfusion at a hydrostatic pressure of 100 cm H$_2$O and at 37° C. was established and continued for 5 min while cannulation of the left atrium via the pulmonary vein was completed. The non-working (Langendorff) preparation was then converted to the working heart model by switching the supply of perfusate buffer from the aorta to the left atrium at a filling pressure of 10 cm H$_2$O. The left ventricle spontaneously ejected into the aortic cannula against a hydrostatic pressure (after-load) of 76 cmH$_2$O (55.9 mmHg). The perfusion solution was Krebs-Henseleit bicarbonate buffer (mM: KCl 4.7, CaCl$_2$ 2.3, KH$_2$PO$_4$ 1.2, MgSO$_4$ 1.2, NaCl 118, and NaHCO$_3$ 25), pH 7.4 containing 11 mM glucose and it was continuously gassed with 95% O$_2$:5% CO$_2$. The buffer was also continuously filtered in-line (initial 8 µm, following 0.4 µm cellulose acetate filters; Sartorius, Germany). The temperature of the entire perfusion apparatus was maintained by water jackets and buffer temperature was continuously monitored and adjusted to maintain hearts at 37° C. throughout perfusion.

A modified 24 g plastic intravenous cannula (Becton Dickson, Utah, USA) was inserted into the left ventricle via the apex of the heart using the normal introducer-needle. This cannula was subsequently attached to a SP844 piezo-electric pressure transducer (AD Instruments) to continuously monitor left ventricular pressure. Aortic pressure was continuously monitored through a side arm of the aortic cannula with a pressure transducer (Statham Model P23XL, Gould Inc., CA, USA). The heart was paced (Digitimer Ltd, Heredfordshire, England) at a rate of 300 bpm by means of electrodes attached to the aortic and pulmonary vein cannulae using supra-threshold voltages with pulses of 5-ms duration from the square wave generator.

Aortic flow was recorded by an in-line flow meter (Transonic T206, Ithaca, N.Y., USA) and coronary flow was measured by timed 30 sec collection of the coronary vein effluent at each time point step of the protocol.

Figure 14:
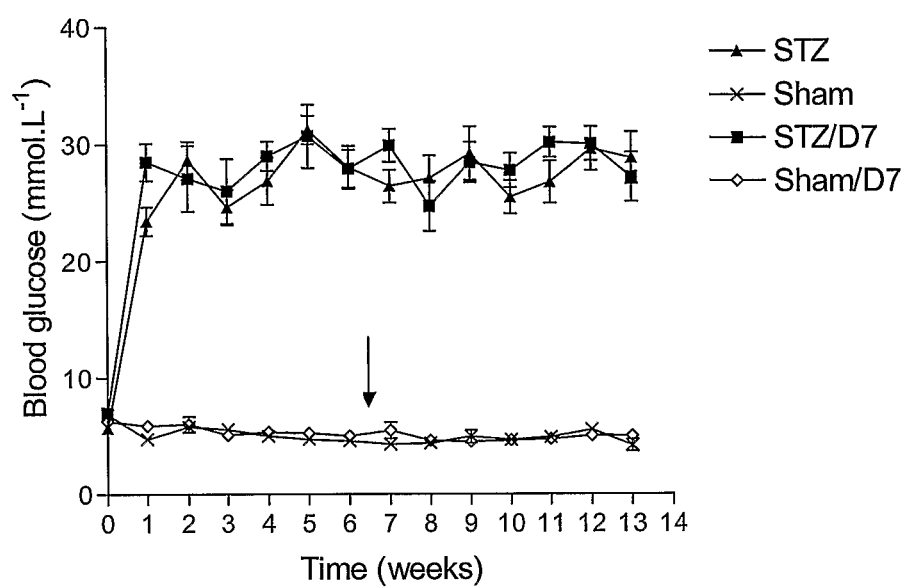
FIG. 14 shows the glucose levels of animals changing over the time period of the experiment in Example 5.
Figure 15:
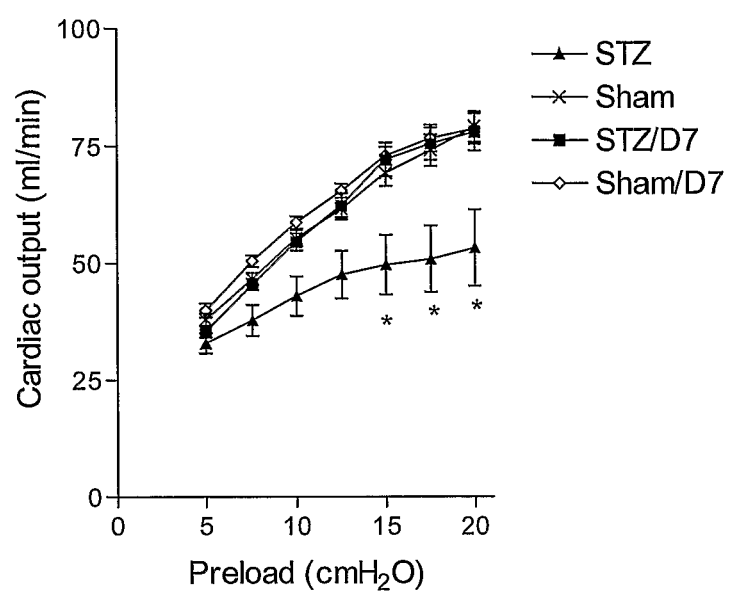
FIG. 15 is a diagram showing cardiac output in animals as measured in Example 5.

The working heart apparatus used was a variant of that originally described by Neely, J R, et al., *Am J Physiol* 212: 804-14 (1967). The modified apparatus allowed measurements of cardiac function at different pre-load pressures (FIG. 14 and FIG. 15). This was achieved by constructing the apparatus so that the inflow height of the buffer coming to the heart could be altered through a series of graduated steps in a reproducible manner. As in the case of the pre-load, the outflow tubing from the aorta could also be increased in height to provide a series of defined after-load pressures. The after-load heights have been converted to mm Hg for presentation in the results which is in keeping with published convention.

All data from the pressure transducers and flow probe were collected (Powerlab 16s data acquisition machine; AD Instruments, Australia). The data processing functions of this device were used to calculate the first derivative of the two pressure waves (ventricular and aortic). The final cardiac function data available comprised:

Cardiac output*; aortic flow; coronary flow; peak left ventricular/aortic pressure developed; maximum rate of ventricular pressure development (+dP/dt); maximum rate of ventricular pressure relaxation (−dP/dt); maximum rate of aortic pressure development (aortic +dP/dt); maximum rate of aortic relaxation (aortic −dP/dt). [*Cardiac output (CO) is the amount of buffer pumped per unit time by the heart and is comprised of buffer that is pumped out the aorta as well as the buffer pumped into the coronary vessels. This is an overall indicator of cardiac function. ** +dP/dt is the rate of change of ventricular (or aortic pressure) and correlates well with the strength of the contraction of the ventricle (contractility). It can be used to compare contractility abilities of different hearts when at the same pre-load (Textbook of Medical Physiology, Ed. A. Guyton. Saunders company 1986). −dP/dt is an accepted measurement of the rate of relaxation of the ventricle].

The experiment was divided into two parts, the first with fixed after-load and variable pre-load the second, which immediately followed on from the first, with fixed pre-load and variable after-load.

Fixed after-Load and Changing Pre-Load:

After the initial cannulation was completed, the heart was initially allowed to equilibrate for 6 min at 10 cm H$_2$O atrial filling pressure and 76 cm H$_2$O after-load. During this period the left ventricular pressure transducer cannula was inserted and the pacing unit started. Once the heart was stable, the atrial filling pressure was then reduced to 5 cm H$_2$O of water and then progressively increased in steps of 2.5cmH$_2$O over a series of 7 steps to a maximum of 20cmH$_2$O. The pre-load was kept at each filling pressure for 2 min, during which time the pressure trace could be observed to stabilize and the coronary flow was measured. On completion of the variable pre-load experiment, the variable after-load portion of the experiment was immediately commenced.

Fixed Pre-Load and Changing after-Load:

During this part of the experiment the filling pressure (pre-load) was set at 10 cm $H_2O$ and the after-load was then increased from 76 cm $H_2O$ (55.9 mm Hg) in 9 steps; of 2 min duration. The maximum height (after-load) to which each individual heart was ultimately exposed, was determined either by attainment of the maximal available after-load height of 145 cm $H_2O$ (106.66 mm Hg), or the height at which measured aortic flow became 0 ml/min. In the later situation, the heart was considered to have "functionally failed." To ensure that this failure was indeed functional and not due to other causes (e.g., permanent ischemic or valvular damage) all hearts were then returned to the initial perfusion conditions (pre-load 10 cm H2O; after-load 75 cm $H_2O$) for 4 minutes to confirm that pump function could be restored. At the end of this period the hearts were arrested with a retrograde infusion of 4 ml of cold KCL (24 mM). The atria and vascular remnants were then excised, the heart blotted dry and weighed. The ventricles were incised midway between the apex and atrioventricular sulcus. Measurements of the ventricular wall thickness were then made using a micro-caliper (Absolute Digimatic, Mitutoyo Corp, Japan).

Data from the Powerlab was extracted by averaging 1min intervals from the stable part of the electronic trace generated from each step in the protocol. The results from each group were then combined and analyzed for differences between the groups for the various cardiac function parameters (aortic flow, cardiac flow, MLVDP, LV or aortic +/−dP/dt). Differences between repeated observations at different pre-load conditions were explored and contrasted between study group using a mixed models approach to repeated measures (SAS v8.1, SAS Institute Inc, Cary N.C.). Missing random data were imputed using a maximum likelihood approach. Significant mean and interaction effects were further examined using the method of Tukey to maintain a pairwise 5% error rate for post hoc tests. All tests were two-tailed. Survival analysis was done using Proc Liftest (SAS V8.2). A one-way analysis of variance was used to test for difference between groups in various weight parameters. Tukey's tests were used to compare each group with each other. In each graph unless otherwise stated.* indicates p<0.05=STZ v STZ/D7, #.p<0.05=STZ/D7 v Sham/D7.

Figure 5:
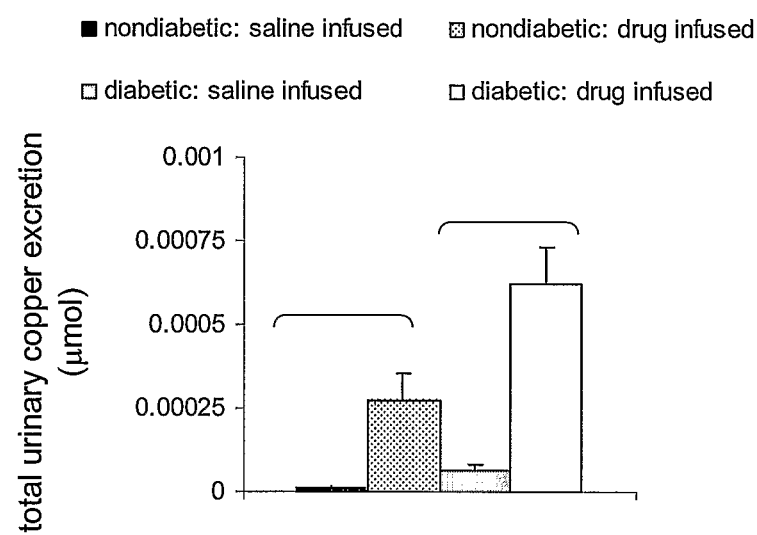
FIG. 5 shows the total amount of copper excreted in non-diabetic and diabetic animals administered saline or drug, wherein total urinary copper excretion (μmol) in nondiabetic animals administered saline (black bar, n=7) or trientine (hatched bar, n=7) and in diabetic animals administered saline (grey bar, n=7) or trientine (white bar, n=7); error bars show SEM and P values are stated if significant (P<0.05).

Results showing the weights of the animals at the end of the experimental period are found in Table 5. Diabetic animals were about 50% smaller than their corresponding age matched normals. A graph of the percentage change in weight for each experimental group is found in FIG. 5, wherein the arrow indicates the start of trientine treatment.

TABLE 5

Initial and final animal body weights (mean ± SD)

| | Number (n) | Treatment | Initial weight (g) | Final weight (g) |
|---|---|---|---|---|
| Group A | 8 | STZ | 361 ± 12 | 221 ± 27 |
| Group B | 8 | STZ/D7 | 401 ± 33 * | 290 ± 56 * |
| Group C | 9 | Sham | 361 ± 16 * | 574 ± 50 |
| Group D | 11 | Sham/D7 | 357 ± 7 | 563 ± 77 |

*P < 0.05

Figure 6:
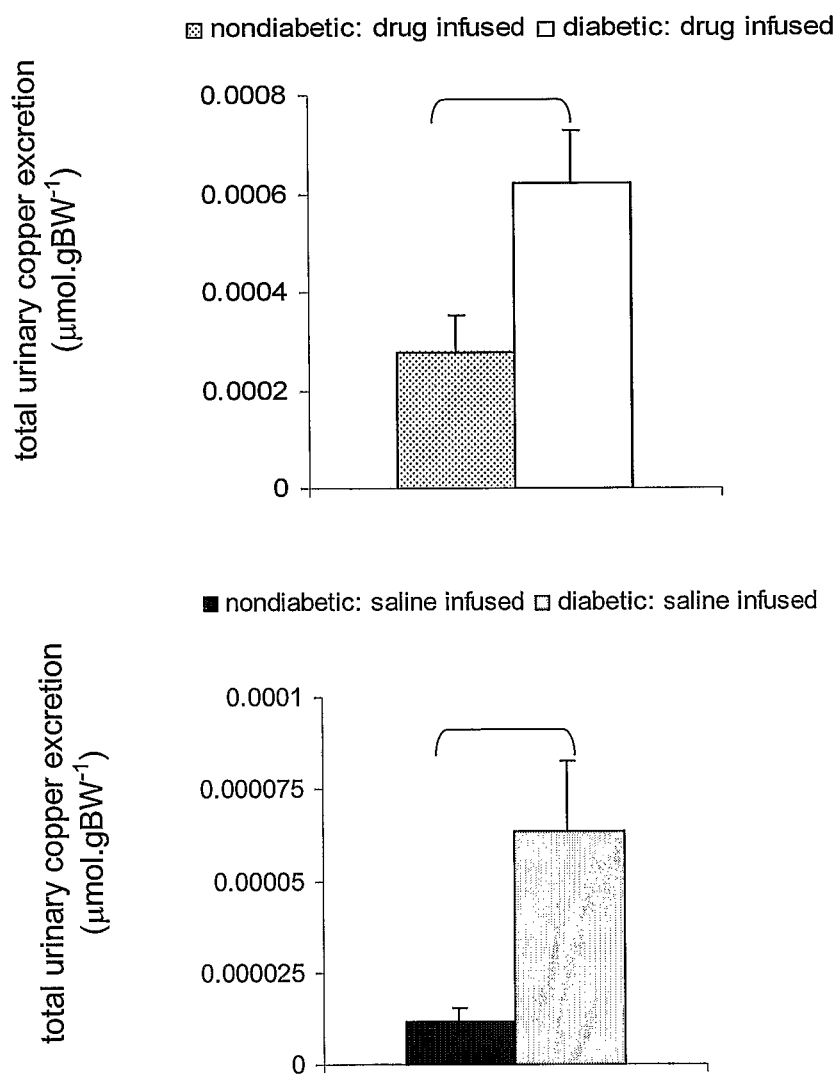
FIG. 6 shows the total amount of copper excreted per gram of bodyweight in animals receiving trientine or saline, wherein total urinary copper excretion per gram of bodyweight (μmol·gBW$^{-1}$) in animals receiving trientine (nondiabetic: hatched bar, n=7; diabetic: white bar, n=7) or saline (nondiabetic: black bar, n=7; diabetic: grey bar, n=7); error bars show SEM and P values are stated if significant (P<0.05).
Figure 7:
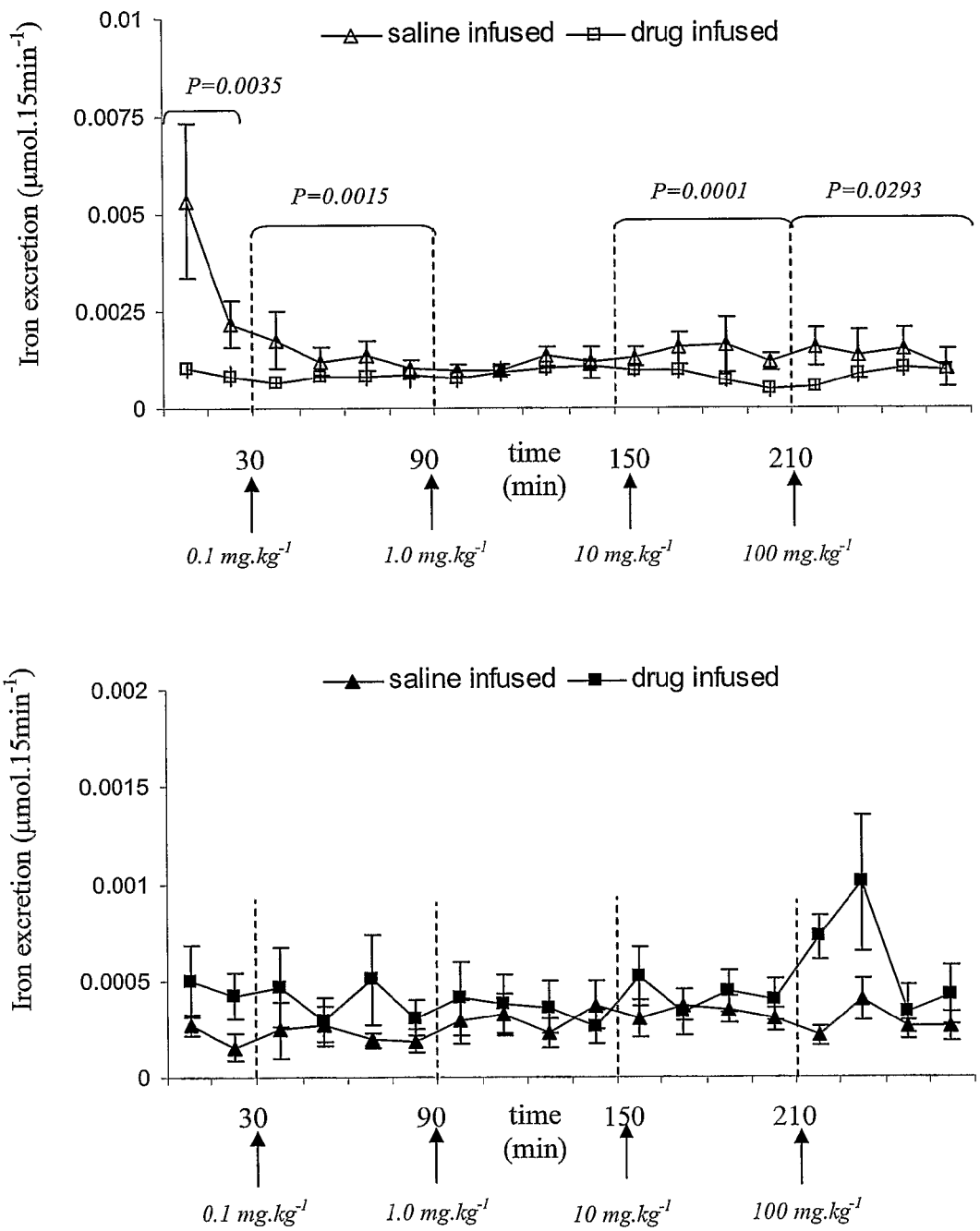
FIG. 7 shows the iron excretion in urine of diabetic and non-diabetic animals receiving increasing doses of trientine or an equivalent volume of saline, wherein iron excretion in urine of diabetic (top) and nondiabetic (bottom) rats receiving increasing doses of trientine (0.1, 1.0, 10, 100 mg·kg$^{-1}$ in 75 μl saline followed by 125 μl saline flush injected at time shown by arrow) or an equivalent volume of saline, and each point represents a 15 min urine collection period (see Example 2 Methods for details); error bars show SEM and P values are stated if significant (P<0.05).

Blood glucose values for the three groups of rats are presented in FIG. 6. Generally, the presence of diabetes was established and confirmed within 3-5 days following the STZ injection. The Sham and Sham/D7 control group remained normoglycemic throughout the experiment. Treatment with the drug made no difference to the blood glucose profile (p=ns) in either treated group compared to their respective appropriate untreated comparison group.

Final heart weight and ventricular wall thickness measurements are presented in Table 6. There was a small but significant improvement in the "heart:body weight" ratio with treatment in the diabetic animals. There was a trend toward improved "ventricular wall thickness:bodyweight" ratio in treated diabetics compared to non-treated but this did not reach significance.

Fixed after-Load and Changing Pre-Load

The following graphs of FIGS. 7 to 12 represent cardiac performance parameters of the animals (STZ diabetic; STZ diabetic+drug; and sham-treated controls) while undergoing increasing atrial filling pressure (5-20 cm$H_2O$, pre-load) with a constant after-load of 75 cm $H_2O$. All results are mean±sem. In each graph for clarity unless otherwise stated, only significant differences related to the STZ/D7 the other groups are shown:* indicates p<0.05 for STZ v STZ/D7, # p<0.05 for STZ/D7 v Sham/D7. Unless stated, STZ/D7 v Sham or Sham/D7 was not significant.

Figure 8:
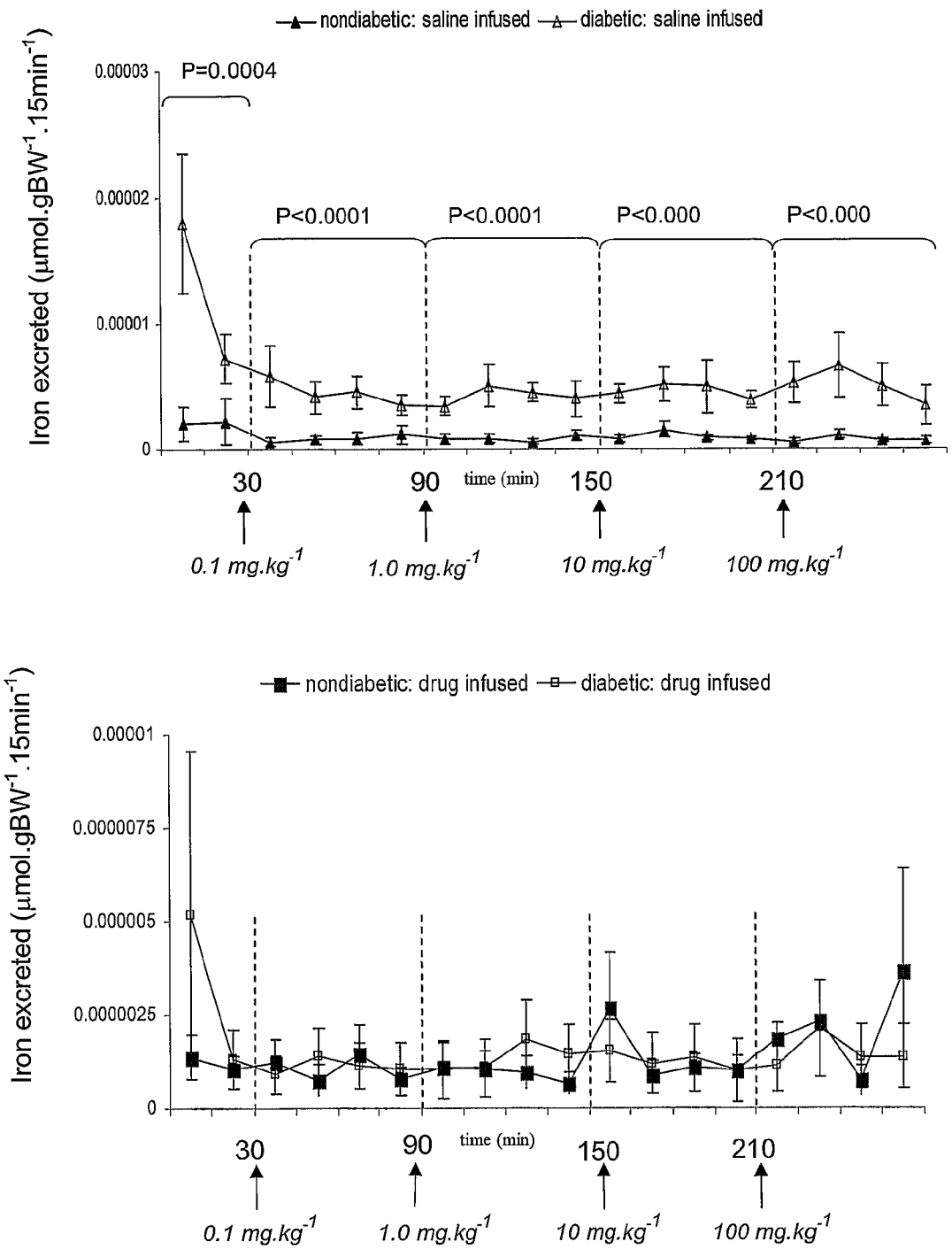
FIG. 8 shows the urinary iron excretion per gram of bodyweight in diabetic and non-diabetic animals receiving trientine or saline, wherein urinary iron excretion per gram of bodyweight in diabetic and nondiabetic animals in response to increasing doses of trientine (bottom; 0.1, 1.0, 10, 100 mg·kg$^{-1}$ in 75 μl saline followed by 125 μl saline flush injected at time shown by arrow) or an equivalent volume of saline (top), and each point represents a 15 min urine collection period (see Example 2 Methods for details); error bars show SEM and P values are stated if significant (P<0.05).
Figure 9:
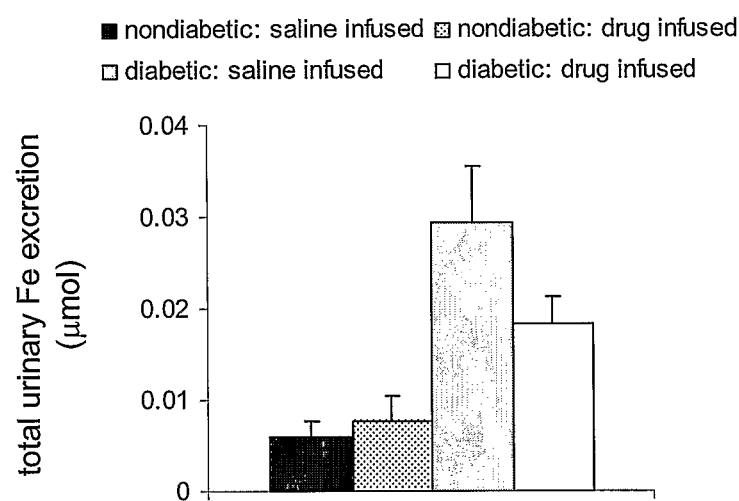
FIG. 9 shows the total urinary iron excretion in non-diabetic and diabetic animals administered saline or drug, wherein total urinary iron excretion (μmol) in nondiabetic animals administered saline (black bar, n=7) or trientine (hatched bar, n=7) and in diabetic animals administered saline (grey bar, n=7) or trientine (white bar, n=7); error bars show SEM and P values are stated if significant (P<0.05).
Figure 10:
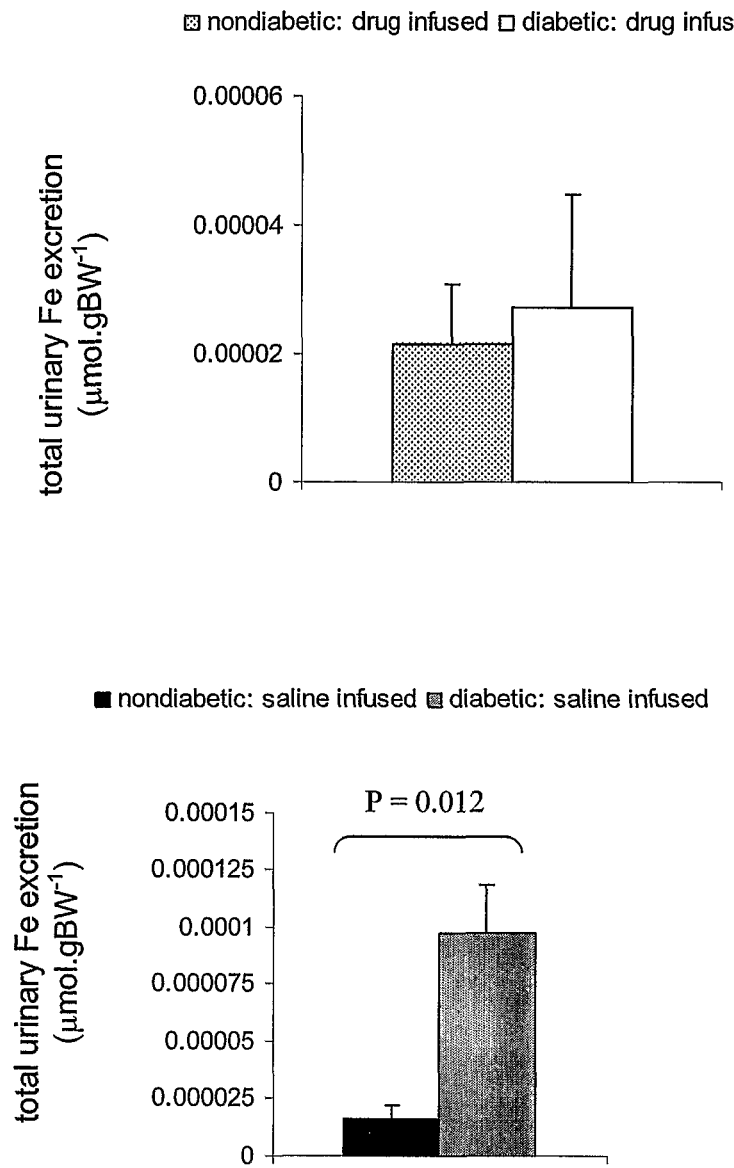
FIG. 10 shows the total urinary iron excretion per gram of bodyweight in animals receiving trientine or saline, wherein total urinary iron excretion per gram of bodyweight (μmol·gBW$^{-1}$) in animals receiving trientine (nondiabetic: hatched bar, n=7; diabetic: white bar, n=7) or saline (nondiabetic: black bar, n=7; diabetic: gray bar, n=7); error bars show SEM and P values are stated if significant (P≤0.05).

Cardiac output (FIG. 7) is the sum to the aortic flow (FIG. 10) and the coronary flow as displayed in FIG. 8. Since the control hearts and experimental groups have significantly different final weights, the coronary flow is also presented (FIG. 9) as the flow normalized to heart weight (note that coronary flow is generally proportional to cardiac muscle mass, and therefore to cardiac weight).

TABLE 6

Final heart weights (g) and per g of animal body Weight (BW) (mean ±

| Group | Heart weight (g) | Heart weight (g)/ BW (g) | Left Ventricular wall thickness (mm) | Left Ventricular wall thickness per BW (mm)/(g) |
|---|---|---|---|---|
| Sham | 1.58 ± 0.13 § | 0.0028 ± 0.0002 § | 3.89 ± 0.38 § | 0.0068 ± 0.0009 § |
| STZ/D7 | 1.18 ± 0.24 ns | 0.0041 ± 0.0005 * | 3.79 ± 0.52 ns | 0.0127 ± 0.0027 ns |
| STZ | 1.03 ± 0.17 | 0.0047 ± 0.0004 | 3.31 ± 0.39 | 0.0152 ± 0.0026 |
| Sham/D7 | 1.58 ± 0.05 § | 0.0028 ± 0.0001 § | 4.03 ± 0.1 § | 0.0072 ± 0.0003 § |

*P < 0.05
§ = significant with the STZ and STZ/D7 groups p < 0.05

Figure 11:
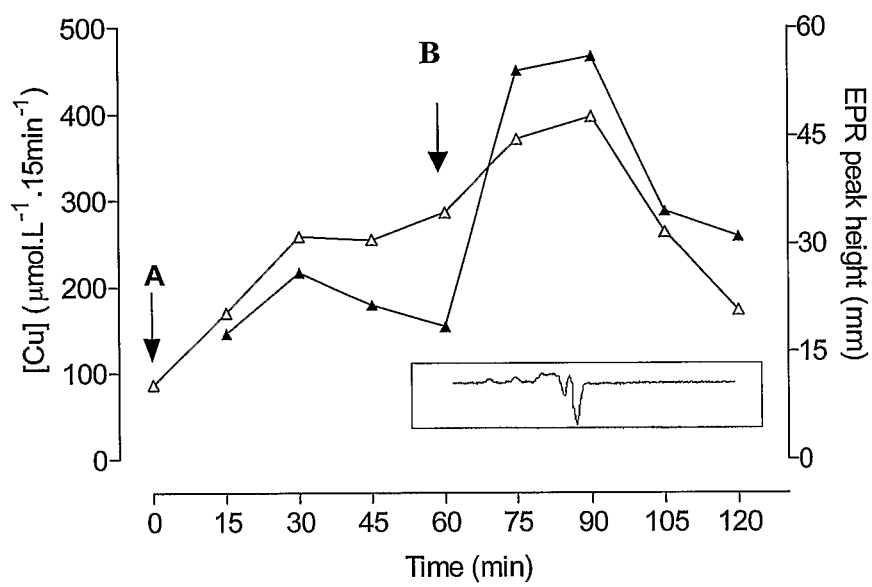
FIG. 11 shows urinary [Cu] by AAS (Δ) and EPR (♦) following sequential 10 mg·kg$^{-1}$ (A) and 100 (B) trientine boluses, as in FIG. 19; (inset) background-corrected EPR signal from 75-min urine indicating presence of Cu$^{II}$-trientine; *, P<0.05, **, P<0.01 vs. control.

The first derivative of the pressure curve gives the rate of change in pressure development in the ventricle with each cardiac cycle and the maximum positive rate of change (+dP/dt) value is plotted in FIG. 11. The corresponding maximum rate of relaxation (−dP/dt) is in FIG. 12. Similar results showing improvement in cardiac function were found from the data derived from the aortic pressure cannula (results not shown).

Fixed Pre-Load and Changing after-Load

Figure 13:
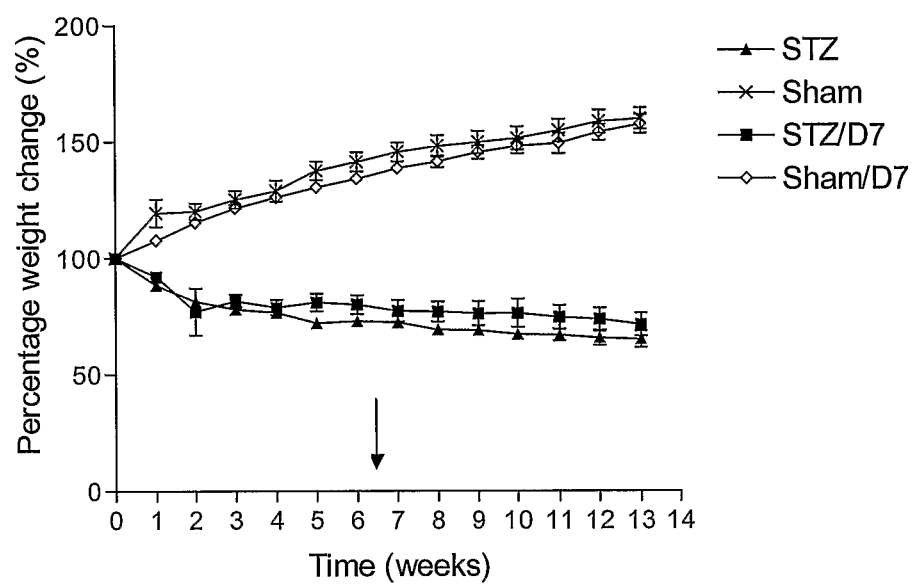
FIG. 13 shows the body weight of animals changing over the time period of experiment in Example 5.

Under conditions for constant pre-load and increasing after-load the ability of the hearts to cope with additional after-load work was assessed. The plot of functional survival, that is, the remaining number of hearts at each after-load that still had an aortic output of greater than 0 ml/min, is found in FIG. 13.

Administration of trientine improved cardiac function in STZ diabetic rats compared to untreated diabetic controls. For example, cardiac output, ventricular contraction and relaxation, and coronary flow were all improved in trientine treated diabetic rats compared to non-treated diabetic controls.

Example 6

This Example was carried out to further evaluate the effect of acute trientine administration on cardiac tissue by assessing left ventricular (LV) histology.

Methods were as follows. Following functional analysis, LV histology was studied by laser confocal (LCM; FIG. 29*a-d*) and transmission electron microscopy (TEM; FIG. 29*e-h*). For LCM, LV sections were co-stained with phalloidin to visualize actin filaments, and $\beta_1$-integrin as a marker for the extracellular space. Ding B, et al., "Left ventricular hypertrophy in ascending aortic stenosis in mice: anoikis and the progression to early failure," *Circulation* 101:2854-2862 (2000).

For each treatment, 5 sections from each of 3 hearts were examined by both LCM and TEM. For LCM, LV sections were fixed (4% paraformaldehyde, 24 h); embedded (6% agar); vibratomed (120 pm, Campden); stained for f-actin (Phalloidin-488, Molecular Probes) and $\beta_1$-integrin antibody with a secondary antibody of goat anti-rabbit conjugated to CY5 (1:200; Ding B, et al., "Left ventricular hypertrophy in ascending aortic stenosis in mice: anoikis and the progression to early failure," *Circulation* 101:2854-2862 (2000)); and visualised (TCS-SP2, Leica). For TEM, specimens were post-fixed (1:1 v/v 1% w/v 0s0 M 0s0 M PBS); stained (aqueous uranyl acetate (2% w/v, 20 mm) then lead citrate (3 mm)); sectioned (70 nm); and visualized (CM-12, Phillips).

The results were as follows. Copper chelation normalized LV structure in diabetic rats. Compared with controls (FIG. 29*a*), diabetes caused obvious alterations in myocardial structure, with marked loss of myocytes; thinning and disorganization of remaining myofibrils; decreased density of actin filaments; and marked expansion of the interstitial space (FIG. 29*b*). These findings are consistent with previous reports. Jackson C V, et al., "A functional and ultrastructural analysis of experimental diabetic rat myocardium: manifestation of acardiomyopathy," *Diabetes* 34:876-883 (1985). By marked contrast, myocardial histology following trientine treatment was improved (FIG. 29*c*). Importantly, the orientation and volume of cardiomyocytes and their actin filaments was largely normalized, consistent with the normalization of −dP$_{LV}$/dt observed in the functional studies. Trientine treatment reversed the expanded cardiac ECM. Myocardium from trientine-treated nondiabetics appeared normal by LCM (FIG. 29*d*) suggesting that it has no detectable adverse effects on LV structure. Thus, Cu chelation essentially restored the normal histological appearance of the myocardium without suppressing hyperglycaemia. These data provide important structural correlates for the functional recovery of these hearts, shown above.

TEM was largely consistent with LCM. Compared with controls (FIG. 29*e*), diabetes caused unmistakable myocardial damage characterized by loss of myocytes with evident myocytolysis; disorganization of remaining cardiomyocytes in which swollen mitochondria were prominent; and marked expansion of the extracellular space (FIG. 29*f*). These findings are consistent with previous reports. Jackson C V, et al., "A functional and ultrastructural analysis of experimental diabetic rat myocardium: manifestation of acardiomyopathy," *Diabetes* 34:876-883 (1985). Oral trientine caused substantive recovery of LV structure in diabetics, with increased numbers and normalized orientation of myocytes; return to normal of mitochondrial structure; and marked narrowing of the extracellular space (FIG. 29*g*). These data suggest that hyperglycaemia-induced systemic $Cu^{II}$ accumulation might contribute to the development of mitochondrial dysfunction. Brownlee M, "Biochemistry and molecular cell biology of diabetic complications," *Nature* 414:813-820 (2001). Myocardium from trientine-treated non-diabetics appeared normal by TEM (FIG. 29*h*). Thus, trientine treatment normalized both cellular and interstitial aspects of hyperglycaemia-induced myocardial damage. Taken together, these microscopic studies provide remarkable evidence that selective Cu-chelation can substantially improve LV structure, even in the presence of severe chronic hyperglycaemia.

In sum, it was demonstrated that (1) Treatment with trientine had no obvious effect on blood glucose concentrations in the two diabetic groups (as expected); (2) There was a small but significant improvement in the (heart weight)/(body weight) ratio in the trientine-treated diabetic group compared to that of the untreated diabetic group; (3) When the Pre-load was increased with the After-load held constant, cardiac output was restored to Sham values. Both the aortic and absolute coronary flows improved in the drug treated group; (4) Indicators for ventricular contraction and relaxation were both significantly improved in the drug treated group compared to equivalent values in the untreated diabetic group. The improvement restored function to such an extent that there was no significant difference between the drug treated and the sham-treated control groups; (5) The aortic transducer measures of pressure change also showed improved function in the drug treated diabetic group compared to the untreated diabetics (data not shown); (6) When after-load was increased in the presence of constant pre-load, it was observed that the heart's ability to function at higher after-loads was greatly improved in the drug treated diabetic group compared to the untreated diabetic group. When 50% of the untreated diabetic hearts had failed, about 90% of the trientine treated diabetic hearts were still functioning; (7) Compared to the untreated diabetic hearts, the response of the drug treated diabetic hearts showed significant improvements in several variables: cardiac output, aortic flow, coronary flow, as well as improved ventricular contraction and relaxation indices; (8) Drug treatment of normal animals had no adverse effects on cardiac performance; and, (9) Histological observations (TEM and LCM) also showed improvement in cardiac architecture in rats following treatment with trientine.

Treatment of STZ diabetic rats with trientine dramatically improves several measures of cardiac function. It is also concluded that administration of oral trientine for 7 weeks in Wistar rats with previously established diabetes of 6 weeks duration resulted in a global improvement in cardiac function.

This improvement was demonstrated by improved contractile function (+dP/dT) and a reduction in ventricular stiffness (−dP/dT). The overall ability of the trientine treated diabetic heart to tolerate increasing after-load was also substantially improved.

Example 7

This Example was carried out to assess the effect of chronic trientine administration on cardiac structure and function in diabetic and non-diabetic humans.

Methods were as follows. Human studies were approved by institutional ethics and regulatory committees. The absorption and excretion of trientine, and representative plasma concentration—time profiles of trientine after oral administration have been reported (see Miyazaki K, et al., "Determination of trientine in plasma of patients with high-performance liquid chromatography," *Chem. Pharm. Bull.* 38:1035-1038 (1990)).

Subjects (30-70 y) who provided written informed consent were eligible for inclusion if they had: T2DM with $HbA_{1c}$>7%; cardiac ejection fraction (echocardiography) ≥45% with evidence of diastolic dysfunction but no regional wall-motion anomalies; no new medications for more than 6 months with no change of β-blocker dose; normal electrocardiogram (sinus rhythm, normal PR Interval, normal T wave and QRS configuration, and isoelectric ST segment); and greater than 90% compliance with single-blinded placebo therapy during a 2-w run-in period. Women were required to be post-menopausal, surgically sterile, or non-lactating and non-pregnant and using adequate contraception. Patients were ineligible if they failed to meet the inclusion criteria or had: morbid obesity (B. M. I.≥45 $kg \cdot m^{-2}$)T1 DM; a history of significant cardiac valvular disease; evidence of autonomic neuropathy; ventricular wall motion abnormality; history of multiple drug allergies; use or misuse of substances of abuse; abnormal laboratory tests at randomisation; or standard contraindications to MRI.

Before randomization, potentially eligible subjects entered a 4-w single blind run-in phase of two placebo-capsules twice-daily and underwent screening echocardiography, being excluded if regional wall motion abnormalities or impaired LV systolic function (ejection fraction <50%) were detected. In addition, LV diastolic filling was assessed using mitral inflow Doppler (with pre-load reduction) to ensure patients had abnormalities of diastolic filling; no patient with normal mitral filling proceeded to randomisation. Subjects meeting inclusion criteria and with no grounds for exclusion were then randomised to receive trientine (600 mg twice-daily) before meals (total dose 1.2 $g \cdot d^{-1}$) or 2 identical placebo capsules twice-daily before meals, in a double-blind, parallel-group design. Treatment assignment was performed centrally using variable block sizes to ensure balance throughout trial recruitment and numbered drug packs were prepared and dispensed sequentially to randomised patients. The double-blind treatment was continued for 6 months in each subject.

At baseline and following 6 months' treatment, LV mass was determined using cardiac MRI, performed in the supine position with the same 1.5 T scanner (Siemens Vision) using a phased array surface coil. Prospectively gated cardiac cine images were acquired in 6 short axis and 3 long axis slices with the use of a segmented k-space pulse sequence (TR 8 ms; TE 5 ms; flip angle 10°; field of view 280-350 mm) with view sharing (11-19 $frames \cdot slice^{-1}$). Each slice was obtained during a breath-hold of 15-19 heartbeats. The short axis slices spanned the left ventricle from apex to base with a slice thickness of 8 mm and inter-slice gap of 2-6 mm. The long axis slices were positioned at equal 60° intervals about the long axis of the LV. Cardiac MRI provides accurate and reproducible estimates of LV mass and volume. LV-mass and volume were calculated using guide point modeling, which produces precise and accurate estimations of mass and volume. Briefly, a three dimensional mathematical model of the LV was interactively fitted to the epicardial and endocardial boundaries of the LV wall in each slice of the study, simultaneously. Volume and mass were then calculated from the model by numerical integration (mass=wall volume×1.05 $g \cdot ml^{-1}$). All measurements were performed by 1 measurer at the end of six months' data collection. Outcome analyses were conducted by intention-to-treat, using a maximum likelihood approach to impute missing at random data within a mixed model, and marginal least-squares adjusted-means were determined. Changes from baseline were compared between treatment-groups in the mixed model with baseline values entered as covariate. Since there were only 2 groups in the main effect and no interaction effect, no post hoc procedures were employed. In additional analysis the influence of clinically important differences between the treatment groups at baseline was considered by adjusting for them as covariates in an additional model. All P values were calculated from 2-tailed tests of statistical significance and a 5% significance level was maintained throughout. The effect of treatment on categorical variables was tested using the procedures of Mantel and Haenzel (SAS v8.01, SAS Institute).

Table 7 shows baseline information on 30 patients with long-standing type 2 diabetes, no clinical evidence of coronary artery disease and abnormal diastolic function who participated in a 6-month randomized, double blind, placebo controlled study of chronic oral therapy with trientine dihydrochloride.

TABLE 7

Characteristics of Study Participants

| | Placebo | Trientine dihydrochloride |
|---|---|---|
| N | 15 | 15 |
| Median age (years) | 54 (range 43-64) | 52 (range 33-69) |
| % female | 44% | 56% |
| Median duration of diabetes (years) | 10 (1-24) | 8 (1-21) |
| Mean body mass index ($kg/m^2$) (SD) | 32 (5) | 34 (5) |
| % hypertensive | 64% | 80% |
| Mean % $HbA_{1c}$ (SD) | 9.3 (1.3) | 9.3 (2.0) |
| Initial left ventricular mass (g) (SD) | 202.2 (53.1) | 207.5 (48.7) |

Trientine (600 mg twice-daily, a dose at the lower end of those employed in adult Wilson's disease, see Dahlman T, et al., "Long-term treatment of Wilson's disease with triethylene tetramine dihydrochloride (trientine)," *Quart. J Med* 88: 609-616 (1995)) or placebo was administered orally for 6 months to equivalent groups of diabetic adults (n=15·$group^{-1}$; Table 7), also matched for pharmacotherapy including: β-blockers, calcium antagonists, ACE-inhibitors, cholesterol-lowering drugs, antiplatelet agents and antidiabetic drugs. LV masses were determined by tagged-molecular resonance imaging (MRI; see Bottini P B, et al., "Magnetic resonance imaging compared to echocardiography to assess left ventricular mass in the hypertensive patient," *Am. J Hypertens* 8: 221-228 (1995)) at baseline and following 6 months' trientine treatment. As expected, diabetics initially had significant LVH, consistent with previous reports. Struthers A D & Morris A D, "Screening for and treating left-ventricular abnormalities in diabetes mellitus: a new way of reducing cardiac deaths," Lancet 359: 1430-1432 (2002).

Results showed that Trientine treatment reverses LVH in type-2 diabetic humans. MRI scans of the heart at baseline and 6-months showed a significant reduction in LV mass. Mean LV mass in diabetics significantly decreased, by 5%, following 6 months' trientine treatment, whereas that in placebo-treated subjects increased by 3% (FIG. 33); this highly significant effect remained after LV mass was indexed to body surface area, and occurred without change in systolic or diastolic blood pressure (Table 8). Thus, trientine caused powerful regression in LV mass without altering blood pressure or urinary volume (FIG. 32). No significant drug-related adverse events occurred during the 6 months' trientine therapy.

TABLE 8

Chronic trientine treatment improves cardiac structure and function in humans
Results of Trientine treatment

|  | Placebo | Trientine-treated |
|---|---|---|
| Δ urinary copper ($\mu mol \cdot L^{-1}$) | 0.67 (−1.16 to 2.49) | −0.83 (−2.4 to 0.74) |
| Δ systolic blood pressure (mmHg) | −1.9 (−10.6 to 6.8) | −3.5 (−9.5 to 1.8) |
| Δ diastolic blood pressure (mmHg) | −4.5 (−9.0 to 0.01) | −3.9 (−13.4 to 6.5) |
| Δ left ventricular mass/body surface area ($g \cdot m^{-2}$) | +3.49 (0.63 to 7.61) | −5.56** (−9.64 to −1.48) |

Differences in key treatment-variables (6 months-baseline, mean (95% confidence interval. *, P < 0.05 vs. placebo **, P < 0.01 vs. placebo).

MRI scans of the heart at baseline and 6-months showed a significant reduction in LV mass.

In sum, trientine administration for 6 months yielded improvements in the structure and function of the human heart.

Example 8

This Example was carried out to assess the effect of chronic trientine administration on urinary metal excretion in diabetic and non-diabetic humans.

Methods were as follows. Human studies were approved by institutional ethics and regulatory committees. We measured urinary metal excretion in human males with T2DM or matched non-diabetic controls, baseline information on which is shown in Table 9, in a randomized, double blind, placebo-controlled trial. Males with uncomplicated T2DM (Table 9) underwent 12-d elemental balance studies in a fully residential metabolic unit. All foods and beverages were provided. Total daily intake (method of double diets) and excretion (urinary and fecal) of trace elements (Ca, Mg, Zn, Fe, Cu, Mn, Mo, Cr and Se) were determined (ICP MS). Baseline measurements were taken during the first 6 d, after which oral trientine (2.4 g once-daily) or matched placebo was administered in a 2×2 randomized double-blind protocol and metal losses measured for a further 6 d.

TABLE 9

Characteristics of Study Participants

|  | Placebo control | Trientine treated control | Placebo diabetic | Trientine treated diabetic |
|---|---|---|---|---|
| Median age (years) | 42 (range 32-53) | 52 (range 30-68) | 51 (range 32-66) | 50 (range 30-64) |
| n | 10 | 10 | 10 | 10 |
| Median duration of diabetes (years) | — | — | 5.9 (range 1-13) | 7.5 (range 1-34) |
| Fasting plasma glucose (mmol · $L^{-1}$) | 4.7 ± 0.3 | 5.0 ± 0.4 | 11.5 ± 3.8 | 10.8 ± 4.3 |
| Mean $HbA_{1c}$ (%) | 5.4 ± 0.2 | 5.0 ± 0.3 | 9.9 ± 2.7 | 9.1 ± 1.6 |
| Body mass index (kg · $m^{-2}$) | 24.6 ± 3.5 | 27.9 ± 5.2 | 32.9 ± 4.5 | 30.4 ± 3.1 |

(mean ± S. E. M. unless otherwise stated); f.b.g., $HbA_{1c}$ and B.M.I. were significantly greater in diabetics and groups were otherwise well-matched).

Results showed that urinary Cu losses are increased following oral trientine treatment in humans with type-2 diabetes. Urine volumes were equivalent in drug- and placebo-treated groups. Basal 2-h Cu-losses were measured for 10 h in diabetic (n=20) and matched control (n=20) subjects during part of day 1 (FIG. 32); and daily losses were determined throughout days 1-6.

Baseline urinary Cu-excretion was significantly greater in diabetics than controls (mean diabetic, 0.257 $\mu mol \cdot d^{-1}$ control, 0.196; P<0.001)..

Trientine- and placebo-evoked 2-h urinary Cu-excretion was measured again in the same subjects on day 7 following oral drug (2.4 g once-daily) or matched placebo (n=10· $group^{-1}$. Trientine increased urinary Cu in both groups, but the excretion rate in diabetes was greater (FIG. 30; P<0.05). There was no corresponding increase in trientine-evoked urinary Fe excretion, although basal concentrations in diabetes were increased relative to control (P<0.001; results not shown). Thus, trientine elicited similar urinary Cu responses in rats with T1DM and in humans with T2DM. Mean trientine-evoked urinary Cu-excretion was 5.8 $\mu mol \cdot d^{-1}$ in T2DM compared to 4.1 $\mu mol \cdot d^{-1}$ in non-diabetic controls, a 40% increase. This correspondence between the two major forms of diabetes in two species suggests that increased systemic $Cu^{II}$ is likely to be widely present in diabetes.

In sum, chronic trientine administration increased urinary copper in both diabetic and nondiabetic groups, but the excretion rate in diabetes was greater. No corresponding increase in urinary Fe excretion was observed with trientine. Thus, trientine elicited similar urinary copper responses in rats with type 1 diabetes mellitus and in humans with type 2 diabetes mellitus.

Example 9

This Example was carried out to determine the effect of oral trientine (triethylene tetramine dihydrochloride) administration on fecal output of metals in diabetic and non-diabetic humans. Methods were as follows.

Oral trientine (2.4 g once daily) or matched placebo were administered to matched groups (n=10/group) of humans with type-2 diabetes mellitus (T2DM) or matched controls. Total metal balance studies were performed in a residential metabolic unit. Total fecal outputs were collected daily for 12 days, freeze dried, and analyzed by ICP-MS for content of Cu, Fe, Zn, Ca, Mg, Mn, Cr, Mb and Se. Baseline measurements were taken during the first 6 d after which oral trientine or matched placebo were administered in a 2×2 randomized double-blind protocol and metal losses measured for a further 6 d.

Results were as follows. Mean daily fecal losses of Cu were not significantly different between subjects before and after administration of trientine or placebo, nor were Cu outputs different between diabetic and control subjects. The lack of effect of trientine on fecal Cu output was unexpected (see Table 11), and contrasts sharply with reports from Wilson's disease, in which trientine reportedly increased fecal Cu excretion.

TABLE 11

Fecal copper excretion

| Mean Cu Losses (mg/day) | Pre-Tment | Post-Tment |
|---|---|---|
| Diab-Plac (n = 10) | 1.914503965 | 1.937921277 |
| Ctrl-Plac (n = 10) | 1.670142101 | 2.078654892 |
| Diab-Drug (n = 10) | 1.869867293 | 1.965342334 |
| Ctrl-Drug (n = 10) | 2.19850868 | 2.045467014 |
| SEM: Diabetic-PrePlac | 0.122570307 | 0.178995736 |
| SEM: Control-PrePlac | 0.1765707 | 0.209400786 |
| SEM: Diabetic-PreDrug | 0.228263465 | 0.144463056 |
| SEM: Control-PreDrug | 0.209289978 | 0.124516832 |

Reference Values

| | |
|---|---|
| Ishikawa et al (2001): control | −1.00 mg/d |
| Kenzie Parnall et al (1988): control | −1.30 mg/d |
| Kosaka H et al (2001) control | 53.5 ug/d |

Results of fecal output studies of other metals were similar. Neither diabetes nor drug had measurable effects on outputs of Zn, Fe, Ca, Mg, Mn, Cr, Mb or Se. In sum, in normal humans and those with T2DM, trientine did not increase fecal output of Cu or other metals. Therefore, trientine does not act in T2DM by increasing fecal Cu output. On the other hand, our previous results showed that trientine administration increased urinary Cu output. Taken in aggregate, these results indicate that trientine acts to remove Cu from the systemic compartment by increasing its loss in the urine. Therefore, systemically active forms of trientine are the preferred embodiment of this invention.

The human data, taken together with those in rats above, indicate that chronic Cu chelation can cause significant regeneration of the heart in those with diabetes-evoked damage. Trientine largely reversed heart failure and LV damage in severely diabetic rats. Furthermore, six months' oral trientine administration significantly ameliorated left ventricular hypertrophy in humans with type-2 diabetes. Rat rats and humans with diabetes acquire increased systemic $Cu^{II}$, which can be removed by treatment with the Cu-selective chelator, trientine.

Example 10

This Example assessed the effect of the copper chelation efficacy of various concentrations of parenteral administration of trientine on anaesthetized diabetic and nondiabetic male Wistar rats through the measurement of copper in the urine.

Stock solutions of various intravenous formulations having concentrations of trientine hydrochloride were made up in 0.9% saline and was stored for four months at 4° C. without appreciable deterioration in efficacy. The concentrations of the stock formulations were: 0.67 mg/ml, 6.7 mg/ml, 67 mg/ml, and 670 mg/ml. The formulation was then administered to the rats in doses of 0.1 mg/kg, 1 mg/kg, 10 mg/kg, and 100 mg/kg to the animals respectively.

Six to seven weeks (mean=44±1 days) after administration of STZ, animals underwent either a control or drug experimental protocol. All animals were fasted overnight prior to surgery but continued to have ad libitum access to deionized water. Induction and maintenance of surgical anesthesia was by 3-5% halothane and 2 l·min$^{-1}$ O2. The femoral artery and vein were cannulated with a solid-state blood pressure transducer (Mikrotip™ 1.4F, Millar Instruments, Texas, USA) and a saline filled PE 50 catheter respectively. The ureters were exposed via a midline abdominal incision, cannulated using polyethylene catheters (external diameter 0.9 mm, internal diameter 0.5 mm) and the wound sutured closed. The trachea was cannulated and the animal ventilated at 70-80 breaths·min$^{-1}$ with air supplemented with O2 (Pressure Controlled Ventilator, Kent Scientific, Connecticut, USA). The respiratory rate and end-tidal pressure (10-15 cmH2O) were adjusted to maintain end-tidal CO2 at 35-40 mmHg (SC-300 CO2 Monitor, Pryon Corporation, Wisconsin, USA). Body temperature was maintained at 37° C. throughout surgery and the experiment by a heating pad. Estimated fluid loss was replaced with intravenous administration of 154 mmol·l$^{-1}$ NaCl solution at a rate of 5 ml·kg$^{-1}$·h$^{-1}$.

Mean arterial pressure (MAP), heart rate (HR, derived from the MAP waveform) oxygen saturation (Nonin 8600V Pulse Oximeter, Nonin Medical Inc., Minnesota, USA) and core body temperature, were all continuously monitored throughout the experiment using a PowerLab/16s data acquisition module (AD Instruments, Australia). Calibrated signals were displayed on screen and saved to disc as 2 s averages of each variable.

Following surgery and a 20 min stabilization period, the experimental protocol was started. The trientine formulation or an equivalent volume of saline was intravenously administered hourly in doses of increasing strength from 0.1 mg/kg, 1.0 mg/kg, 10 mg/kg, and 100 mg/kg. Urine was collected throughout the experiment in 15 min aliquots.

Sample pretreatment was carried out as follows. Urine: Urine was collected in pre-weighed 1.5 ml micro test tubes (eppendorf). After reweighing, the urine specimens were centrifuged and the supernatant diluted 25:1 with 0.02 M 69% Aristar grade HNO$_3$. The sample was stored at 4° C. prior to GF-AAS analysis. If it was necessary to store a sample for a period in excess of 2 weeks, it was frozen and kept at −20° C. Serum: Terminal blood samples were centrifuged and serum treated and stored as per urine until analysis. From the trace metal content of serum from the terminal blood sample and urine collected over the final hour of the experiment, renal clearance was calculated using the following equation:

renal clearance of trace metal (μl·min$^{-1}$)=concentration of metal in urine (μg·μl$^{-1}$)*rate of urine flow (μl·min$^{-1}$) concentration of metal in serum (ρg·μl$^{-1}$)

Statistical analyses were carried out as follows. All values are expressed as mean±SEM and P values <0.05 were considered statistically significant. Student's unpaired t-test was initially used to test for weight and glucose differences between the diabetic and control groups. For comparison of responses during drug exposure, statistical analyses were performed using analysis of variance (Statistics for Windows v.6.1, SAS Institute Inc., California, USA). Subsequent statistical analysis was performed using a mixed model repeated measures ANOVA design (see Example 4).

The results were as follows. With regard to the cardiovascular effects there were no adverse effects from the acute injection of trientine. See FIG. 25 that shows no adverse cardiovascular effects after the injection, although at 100 mg/kg this gave a transient drop in blood pressure. This change was a maximum blood pressure fall of 19+/−4 mmHg, however the rat recovered in 10 minutes (not shown).

In summary, acute intravenous administration of trientine in the concentration ranges from between 0.1 mg/kg, 1 mg/kg, 10 mg/kg, and 100 mg/kg has no significant effect on blood pressure. Furthermore, a trientine formulation is efficacious as a copper chelator when given intravenously and that trientine in saline remains active as a copper chelator after storage at 4° C. for 4 months.

Example 11

This Example assessed the stability of a trientine formulation after being stored by its ability to chelate copper.

A standard 100 mM solution of Trientine HCl was made up in deionized (MilliQ) water. One sample of the solution was stored in the dark at 4° C. and 21° C. in the dark and a third sample was stored at 21° C. in daylight.

Figure 26:
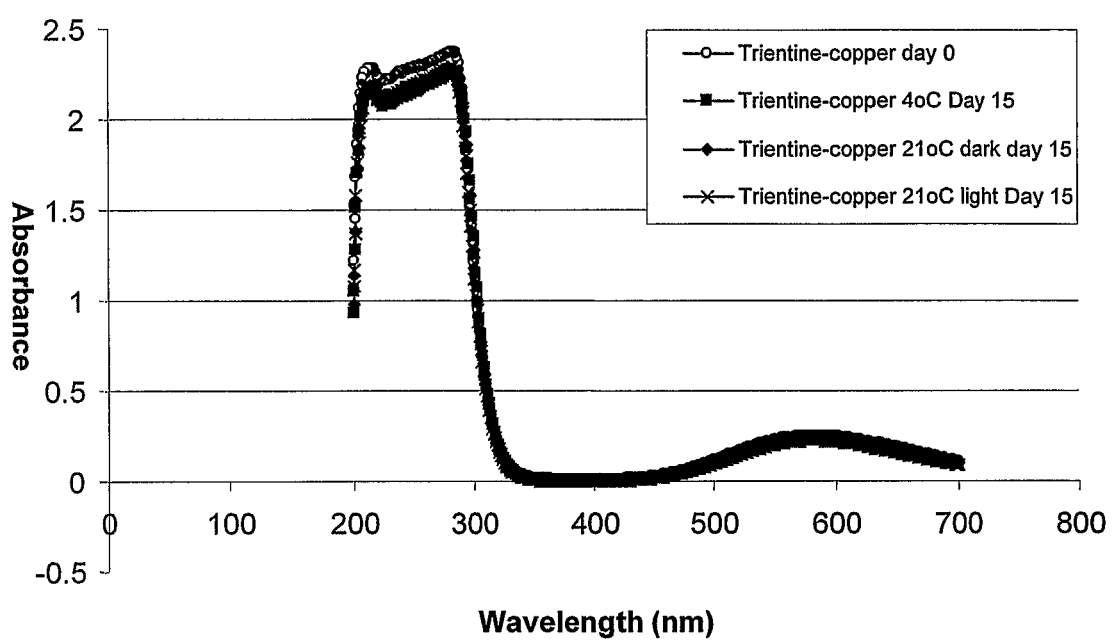
FIG. 26 shows the ultraviolet-visible spectral trace of the trientine containing formulation after being stored for 15 days and upon the addition of copper to form the trientine-copper complex. The traces were taken on day 0 (control formulation) and day 15. There were three formulations containing trientine one was stored in the dark at 4° C., the second at room temperature (21° C.) in the dark and a third at room temperature in daylight. When the spectral was taken copper was added.

The Ultraviolet-visible spectrum of the formulation was initially measured at day 0 and then at day 15. 20 µl aliquots of sample solutions were taken at day 15. For each aliquot 960 µl of 50 mM TRIS buffer and 20 µl aliquot of Copper Nitrate standard (100 mM—Orion Research Inc) were added. This was then measured over wavelengths 700-210 nm to determine the binding stability of the trientine formulations. See FIG. 26 that shows that there was no detectable change in the ability of the trientine formulation to chelate copper over this 15 day time period irrespective of storage conditions. Furthermore room light had no detectable detrimental effect on copper chelation and that trientine is stable as a chelator while in solution.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, those skilled in the art will recognize that the invention is also thereby described in terms of any individual member or subgroup of members of the Markush group.

Other embodiments are within the following claims. Under no circumstances may the patent be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention claimed is:

1. A composition comprising a pharmaceutically acceptable carrier and a therapeutically effective amount of a succinic acid addition salt of triethylenetetramine.

2. The composition of claim 1 comprising from 50 mg to 500 mg of the succinic acid addition salt of triethylenetetramine.

3. The composition of claim 1 comprising from 110 to 290 mg of the succinic acid addition salt of triethylenetetramine.

4. The composition of claim 1 comprising from 130 to 270 mg of the succinic acid addition salt of triethylenetetramine.

5. The composition of claim 1 comprising from 140 to 260 mg of the succinic acid addition salt of triethylenetetramine.

6. The composition of claim 1 comprising from 180 to 220 mg of the succinic acid addition salt of triethylenetetramine.

7. The composition of claim 1 comprising from 50 mg to 100 mg of the succinic acid addition salt of triethylenetetramine.

8. The composition of claim 1 wherein the amount of the succinic acid addition salt of triethylenetetramine is selected from the group consisting of 50 mg, 110 mg, about 130 mg, 140 mg, and 150 mg.

9. The composition of claim 1 wherein the amount of the succinic acid addition salt of triethylenetetramine is selected from the group consisting of 1.2 mg, 10 mg, 12 mg, 20 mg, 30 mg, and 40 mg.

10. The composition of claim 1, wherein the succinic acid addition salt of triethylenetetramine is prepared using an acid which yields a physiologically acceptable salt.

11. The composition of claim 1, wherein said composition is in a form suitable for oral administration.

12. The composition of claim 11, wherein said form suitable for oral administration is a capsule.

13. The composition of claim 11, wherein said form suitable for oral administration is a tablet.

14. The composition of claim 13, wherein said tablet is an enteric-coated tablet or a layered tablet.

15. The composition of claim 11, wherein said form suitable for oral administration is a sustained release preparation, a delayed release preparation, a slow release preparation, a controlled release preparation, or an extended release preparation.

16. The composition of claim 11, wherein said composition is in a form suitable for transdermal administration.

17. The composition claim 1, wherein said composition is in a form suitable for transmucosal administration.

18. The composition of claim 1, wherein said composition is in a form suitable for administration as a suppository.

* * * * *